United States Patent [19]

Früh et al.

[11] Patent Number: 5,703,106
[45] Date of Patent: Dec. 30, 1997

[54] ANTAGONISTS OF ENDOTHELIN RECEPTORS

[75] Inventors: Thomas Früh, Magden; Thomas Pitterna, Basel, both of Switzerland; Toshiki Murata, Nara-ken, Japan; Lene D. Svensson, Lemvig, Denmark; Yoko Yuumoto; Junichi Sakaki, both of Hyogo, Japan

[73] Assignee: Japat Ltd., Basel, Switzerland

[21] Appl. No.: 718,593

[22] PCT Filed: Mar. 17, 1995

[86] PCT No.: PCT/EP95/01013

§ 371 Date: Sep. 25, 1996

§ 102(e) Date: Sep. 25, 1996

[87] PCT Pub. No.: WO95/26360

PCT Pub. Date: Oct. 5, 1995

[30] Foreign Application Priority Data

Mar. 28, 1994 [EP] European Pat. Off. ............ 94 810 191

[51] Int. Cl.[6] .................... C07D 261/06; A61K 31/42
[52] U.S. Cl. .................... 514/378; 514/383; 514/419; 548/247; 548/266.4; 548/467; 548/496; 548/497
[58] Field of Search .................... 514/419, 378, 514/383; 548/496, 497, 467, 247, 266.4

[56] References Cited

U.S. PATENT DOCUMENTS 5,284,828   2/1994   Hemmi et al. .................... 514/18

FOREIGN PATENT DOCUMENTS 457 195   11/1991   European Pat. Off. .
460 679   12/1991   European Pat. Off. .

*Primary Examiner*—Joseph McKane
*Assistant Examiner*—Richard S. Myers, Jr.
*Attorney, Agent, or Firm*—Wenderoth, Lind & Ponack

[57] ABSTRACT

The present invention provides novel compounds having pharmacological properties represented by the general formula I

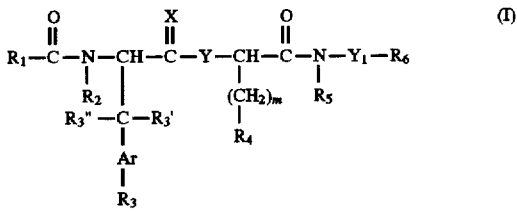

processes for the manufacture, pharmaceutical compositions and the use of the compounds of formula I and salts thereof.

18 Claims, No Drawings

ANTAGONISTS OF ENDOTHELIN RECEPTORS

This application is a filing under 35 U.S.C.371 of PCT/EP95/01013, filed Mar. 17, 1995.

BACKGROUND OF THE INVENTION

The present invention relates to novel compounds as antagonists of endothelin (ET) receptors, processes for their preparation, their use and pharmaceutical compositions.

ETs are a family of vasoactive peptides with 21 amino acid residues and two intramolecular disulfide bonds. They comprise ET-1, the original ET isolated from the culture media of porcine endothelial cells, ET-2 and ET-3.

ETs, of which biosynthesis is enhanced by many biological and pathological factors, are widely distributed in both peripheral and brain tissues of mammalians, and elicit a number of biological responses by binding to at least two distinct ET receptor subtypes, $ET_A$ and $ET_B$ receptors.

ET receptors are present in cardiovascular, renal, hepatic and neural tissues. ET receptors are also found in the respiratory, gastro-intestinal, endocrine, central nervous and genito-urinary systems, the blood and blood forming organs, the sensory organs, and other tissues in the body.

ETs are the most potent and longest acting endogeneous constrictors of blood vessels identified to date. ETs also cause contraction of various non-vascular smooth muscles including the air-way, and the cardiac muscle. In addition, ETs are ulcerogenic and pro-inflammatory. ETs have regulatory functions on hormone- or peptide-secretion, neurotransmission, ion-transport and metabolism.

SUMMARY OF THE INVENTION

The present invention provides novel compounds represented by the general formula I

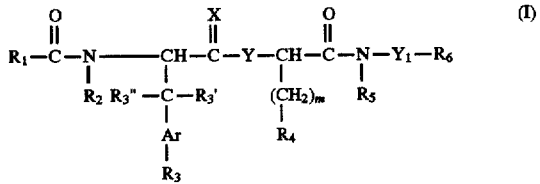

wherein Ar represents a direct bond or arylene;

m is 0, 1, 2, or 3;

$R_1$ is lower alkyl, cycloalkyl-lower alkyl, aryl-lower alkyl, cycloalkyl, aryl, aryl-cycloalkyl, lower alkoxy, or aryloxy;

$R_2$ is hydrogen, lower alkyl, aryl-lower alkyl, cycloalkyl, or cycloalkyl-lower alkyl;

$R_3$ represents hydrogen, hydroxy, amino, nitro, lower alkyl, cycloalkyl, or aryl-lower alkyl, provided that Ar is a direct bond, or represents aryl;

$R_3'$ represents hydrogen, lower alkyl, cycloalkyl, aryl-lower alkyl, or aryl; or $R_3$ and $R_3'$ together form a ring structure, provided that Ar is a direct bond;

$R_3''$ is hydrogen, lower alkyl or aryl; or $R_2$ and $R_3''$ together form the lower alkylene group —$(CH_2)_n$— wherein n is an integer of 1, 2 or 3; or $R_2$ and $R_3''$ together form a group represented by the formula: —$(CH_2)_o$—$Ar_1$— or —$Ar_1$—$(CH_2)_o$—, respectively, wherein o is zero or an integer of 1 or 2, and $Ar_1$ is arylene; C(=X) is C(=O), C(=S), C(=NH), C(=N-lower alkyl); C=NH—OH, or $CH_2$; and Y is a direct bond, —NH—,

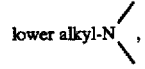

oxygen, or methylene; or

C(=X) is CHOH and Y is a direct bond or methylene;

$R_4$ is lower alkyl, lower alkenyl, cycloalkyl, aryl-lower alkyl, aryl-lower alkenyl, or aryl;

$R_5$ is hydrogen, lower alkyl, aryl-lower alkyl, cycloalkyl, or cycloalkyl-lower alkyl;

$R_6$ represents lower alkyl, halo-lower alkyl, hydroxy-lower alkyl, acyloxy-lower alkyl, lower alkoxy-lower alkyl, aryloxy-lower alkyl, aryl-lower alkyl, lower alkenyl, lower alkenyl which substituted by at least one substituent selected from the group consisting of carboxy, lower alkoxycarbonyl, hydroxy, lower alkoxy, amino, lower alkylamino and di-lower alkylamino, or represents aryl-lower alkenyl, aryl or lower alkyl which is substituted by carboxy or lower alkoxycarbonyl and also by amino, lower alkylamino or di-lower alkylamino; or $R_5$ and $R_6$ together form the lower alkylene group —$(CH_2)_p$— wherein p is an integer of 3–5, or together form a group represented by the formulae: —$(CH_2)_q$—$Ar_1$— or —$Ar_1$—$(CH_2)_q$—, wherein q is zero or an integer of 1 or 2, and $Ar_1$ is arylene; and $Y_1$ represents —$SO_2$—, —O—, —NH—, —NH—CO—, —NH—CO—O— or —NH—$SO_2$—; and wherein "aryl", it being a mono- or bivalent aryl radical or aryl moiety, respectively, represents, in each case, a corresponding carbocyclic or heterocyclic aryl radical or aryl moiety, respectively; and salts thereof;

processes for the manufacture, pharmaceutical compositions and the use of the compounds of formula I and salts thereof.

All of the compounds of the present invention possess two or more chiral centers which may exist e.g. in the R(D), S(L), S,R and/or S,S configuration. The present invention includes all essentially pure enantiomeric and diastereomeric forms as well as appropriate mixtures of corresponding enantiomers and diastereomers, e.g. racemates.

Aryl represents a corresponding carbocyclic or heterocyclic aryl radical or aryl moiety, respectively.

Carbocyclic aryl, if not defined differently, generally represents, for example, phenyl, and naphthyl such as 2-naphthyl or 3-naphthyl. Carbocyclic aryl may be unsubstituted or poly-substituted, for example, di- or tri-substituted.

Heterocyclic aryl, if not defined differently, in particular represents an appropriate 5- or 6-membered and monocyclic radical which has up to four identical or different hetero atoms, such as nitrogen, oxygen or sulfur atoms, preferably one, two, three or four nitrogen atoms, an oxygen atom or a sulfur atom, a nitrogen and an oxygen or a sulfur atom, two nitrogen atoms and an oxygen or a sulfur atom. Appropriate 5-membered heteroaryl radicals are, for example, monoaza-, diaza-, triaza-, tetraaza-, monooxa-, monothia-, oxaza-, thiaza-, oxadiaza- or thiadiaza-cyclic aryl radicals, for example, thienyl such as 2-thienyl or 3-thienyl, furanyl such as 2-furanyl or 3-furanyl, pyrrolyl such as 2- or 3-pyrrolyl, 1-lower alkyl-pyrrolyl such as 1-methyl-3-pyrrolyl, pyarzolyl such as pyrazol-1-yl, oxazolyl such as 2-, 4, or 5-oxazolyl, isoxazolyl such as 3-, 4- or 5-isoxazolyl, oxadiazolyl such as 1,2,4-oxadiazol-3-yl, thiazolyl such as 2-, 4- or 5-thiazolyl, isothiazolyl such as 3-, 4- or 5-isothiazolyl, thiadiazolyl such as 1,2,3-thiadiazol-4-yl or 1,2,4-thiadiazol-2-yl, imidazolyl such as 2-, 4- or 5-imidazolyl, 1-lower alkyl-imidazolyl such as 1-methyl-4-imidazolyl, triazolyl such as 1H-1,2,3-triazol-1-yl, 2H-1,2,3-triazol-2yl, 1H-1,2,4-triazol-1-yl, 4-H-1,2,4-triazol-3-yl, or 1H-1,3,4-triazol-1-yl, tetrazolyl such as 1H-tetrazol-5-yl, while suitable appropriate 6-membered radicals are in particular azaaryl or oxaaryl radicals such as pyrimidyl such as 2-pyrimidyl, pyranyl such as 2-pyranyl or 3-pyranyl, or pyridyl such as 4-pyridyl. Heterocyclic aryl likewise represents bicyclic heterocyclic aryl, in particular benzo-fused 5- or 6-membered heteroaryl radicals, for example, indolyl such as 2- or especially 3-indolyl, 1-lower alkyl-indolyl such as 1-methyl-3-indolyl, benzothiophenyl such as 2- or especially 3-benzothiophenyl, methylenedioxy-phenyl such as 3,4-methylenedioxy-phenyl, benzofuranyl such as 2- or 3-benzofuranyl, quinolinyl such 2-, 3- or especially 4-quinolinyl, and isoquinolinyl such as 1-, 3- or 4-isoquinolinyl. Heterocyclic aryl may be unsubstituted or mono- or poly-, for example, di- or tri-substituted.

The substituents of a corresponding carbocyclic or heterocyclic aryl radical or aryl/arylene moiety, respectively, are selected from the group consisting of, for example, halogen such as fluorine, chlorine, bromine or iodine, lower alkyl such as methyl or ethyl, lower alkoxy such as methoxy or ethoxy, substituted lower alkyl such as halo-lower alkyl, for example, trifluoromethyl, cyano, amino, hydroxy, aryl-substituted lower alkoxy such as a phenyl-lower alkoxy, for example, benzyloxy, carboxy, lower alkoxycarbonyl, and nitro. Where the aryl such as phenyl is polysubstituted, the substituents may be different or same.

Arylene a corresponding carbocyclic or heterocyclic arylene radical or arylene moiety, respectively.

Carbocyclic arylene is, for example, phenylene such as 1,2-phenylene, 1,3-phenylene or 1,4-phenylene, furthermore naphthylene such as 1,2-naphthylene.

Heterocyclic arylene is, for example, pyridylene such as 2,3-pyridylene or 2,6-pydridylene.

The substituents for carbocyclic or heterocyclic arylene are for example, those described for the aryl group above.

The preferred carbocyclic arylene is in case of Ar, for example, 1,4-phenylene, whereas the preferred heterocyclic arylene is in case of Ar, for example, 2,5-pyridylene. The preferred carbocyclic arylene is in case of $Ar_1$, for example, 1,2-phenylene, whereas the preferred heterocyclic arylene is in case of $Ar_1$, for example, 2,3-pyridylene.

In aryl-lower alkyl, the aryl moiety has the same meaning as described for the aryl; and the lower alkyl moiety has the same meaning as described for the lower alkyl. Aryl in aryl-lower alkyl preferably is unsubstituted or furthermore substituted phenyl. Preferred is phenyl-$C_1$–$C_4$-alkyl.

In aryl-lower alkenyl, the aryl moiety has the same meaning as described for the aryl; and the lower alkenyl moiety has the same meaning as described for the lower alkenyl. Aryl in aryl-lower alkenyl preferably is unsubstituted or furthermore substituted phenyl. Preferred is phenyl-$C_2$–$C_7$-alkenyl, especially phenyl-$C_2$–$C_5$-alkenyl.

In aryl-cycloalkyl, the aryl moiety has the same meaning as described for the aryl group; and the cycloalkyl moiety has the same meaning as described for the cycloalkyl group. The aryl-cycloalkyl is, for example, phenyl-$C_3$–$C_8$-cycloalkyl such as phenyl-cyclopropyl. Aryl in aryl-cycloalkyl preferably is unsubstituted or furthermore substituted phenyl.

In aryl in aryloxy-lower alkyl, has the meaning as described for the aryl group. Preferably, aryloxy in aryloxy-lower alkyl is phenoxy.

The ring structure formed by $R_3$ and $R_3'$ is fluorenyl such as 9-fluorenyl, anthryl such as 9-anthryl, or preferably a dibenzosuberyl such as 5-dibenzosuberyl.

In acyloxy-lower alkyl, the acyl moiety represents, for example, lower alkanoyl, phenyl-lower alkanoyl, benzoyl, lower alkanesulfonyl or benzenesulfonyl.

Preferred Ar is 1,4-phenylene.

Preferred $R_1$ is 3,5-di-lower alkyl phenyl such as 3,5-dimethyl-phenyl.

Preferred $R_2$ is lower alkyl such as methyl.

Preferred $R_3$ is phenyl or thienyl such as 3-thienyl or isoxazolyl such as 5-isoxazolyl.

Preferred $R_3'$ is hydrogen.

Preferred $R_3''$ is hydrogen.

Preferred $R_4$ is 1-H-indol-3-yl, if m represents one.

Preferred $R_4$ is lower alkyl, if m represents zero.

Preferred $R_5$ is hydrogen.

Preferred $R_6$ is phenyl, thienyl, lower alkyl, or lower alkenyl.

Preferred X is oxygen.

Preferred Y is nitrogen.

Preferred $Y_1$ is —$SO_2$—.

The compounds represented by the formula (I) are capable of forming pharmaceutically acceptable acid addition salts and/or base addition salts. Pharmaceutically acceptable acid addition salts of the compounds (I) include those of inorganic acids, for example, hydrohalic acids such as hydrochloric acid, hydrodromic acid or hydroiodic acid, nitric acid, sulfuric acid, phosphoric acid; organic acids, for example, lower alkanoic acids such as formic acid, acetic acid, propionic acid, butylic acid, hydroxy acids such as lactic acid, citric acid or malic acid, dicarboxylic acids such as maleic acid or succinic acid, sulfonic acids, for example, lower alkanesulfonic acids such as methanesulfonic acid, or benzenesulfonic acid.

Salts of the present compounds (I) with bases are, for example, those with bases, for example, inorganic bases such as ammonium hydroxide or metal hydroxide, such as lithium hydroxide, such as alkaline metal hydroxide such as sodium hydroxide, potassium hydroxide, alkaline earth metal hydroxide, such as calcium hydroxide; or those with organic bases, for example, amines, for example, mono-, di- or tri-lower alkylamines, such as mono-, di- or tri-methyl-amine or -ethyl-amine.

The general definitions used above and below, unless defined differently, have the following meanings:

The expression "lower" means that corresponding groups and compounds in each case in particular comprise not more than 7, preferably not more than 4, carbon atoms.

The term "lower alkyl" means an alkyl having 1 up to and including 7 carbon atoms, preferably 1 up to and including 4 carbon atoms, and for example, is methyl, ethyl, n-propyl, isopropyl, n-butyl, isobutyl, tert-butyl, straight or branched pentyl, straight or branched hexyl, or straight or branched heptyl.

The cycloalkyl has preferably 3 up to and including 8 carbon atoms, and is cyclopropyl, cyclobutyl, cyclopentyl, cyclohexyl, cyclopentyl, or cycloheptyl, or cyclooctyl. The cycloalkyl is preferably $C_5$–$C_6$-cycloalkyl. The cycloalkyl may be substituted. Substituent for the cyclohexyl is, for example, a lower alkyl such as methyl or ethyl.

In the cycloalkyl-lower alkyl, the cycloalkyl moiety has the same meanings as described above for the cycloalkyl;

and the lower alkyl moiety has the same meaning as described for the lower alkyl.

Lower alkenyl is in particular $C_2$–$C_7$-alkenyl and is, for example, vinyl, allyl, or methallyl, preferred is $C_3$–$C_5$-alkenyl, especially allyl is preferred.

Lower alkoxy is in particular $C_1$–$C_7$alkoxy and is, for example, methoxy, ethoxy, n-propyloxy, isopropyloxy, n-butyloxy, isobutyloxy, sec-butyloxy, tert-butyloxy and also includes corresponding pentyloxy, hexyloxy and heptyloxy radicals. $C_1$–$C_4$alkoxy is preferred.

Lower alkylene is, for example, $C_1$–$C_7$alkylene, and is straight-chain or branched and is in particular methylene, ethylene, propylene and butylene and also 1,2-propylene, 2-methyl-1,3-propylene and 2,2-dimethyl-1,3-propylene. $C_1$–$C_5$alkylene is preferred.

Halogen is in particular halogen of atomic number not more than 35, such as fluorine, chlorine or bromine, and also includes iodine.

Halo-lower alkyl is preferably halo-$C_1$–$C_4$alkyl such as trifluoromethyl, 1,1,2-trifluoro-2-chloroethyl or chloromethyl.

Hydroxy-lower alkyl is in particular hydroxy-$C_1$–$C_7$-alkyl such as hydroxymethyl, 2-hydroxyethyl, 2- or 3-hydroxpropyl. Hydroxy-$C_1$–$C_4$-alkyl is preferred.

Lower alkoxy-lower alkyl is in particular $C_1$–$C_4$-alkoxy-$C_1$–$C_7$-alkyl such as methoxymethyl, 2-methoxy-ethyl, 2-ethoxyethyl, 2-methoxy- or 3-methoxy-propyl. $C_1$–$C_4$-Alkoxy-$C_1$–$C_4$alkyl is preferred.

Phenyl-lower alkoxy is in particular phenyl-$C_1$–$C_4$alkoxy such as benzyloxy, 1- or 2-phenylethoxy, 3-phenylpropyloxy or 4-phenylbutyloxy.

Lower alkoxycarbonyl is in particular $C_2$–$C_8$alkoxycarbonyl and is, for example, methoxy-, ethoxy-, propyloxy- or pivaloyloxy-carbonyl. $C_2$–$C_5$alkoxycarbonyl is preferred.

Lower alkylamino is in particular $C_1$–$C_7$alkylamino and is, for example, methyl-, ethyl-, n-propyl- and isopropyl-amino. $C_1$–$C_4$alkylamino is preferred.

Di-lower alkylamino is in particular di-$C_1$–$C_4$alkylamino, such as dimethyl-, diethyl-, di-n-propyl-, methylpropyl-, methylethyl-, methylbutyl-amino and dibutylamino. Lower alkanoyl is in particular $C_1$–$C_7$-alkanoyl and is, for example, formyl, acetyl, propionyl, butyryl or pivaloyl. $C_2$–$C_5$-Alkanoyl is preferred.

Phenyl-lower alkanoyl is in particluar phenyl-$C_2$–$C_5$-alkanoyl and is, for example, phenylacetyl or phenylpropionyl.

Lower alkanesulfonyl is in particular $C_1$–$C_7$-alkanesulfonyl and is, for example, methan-, ethan-, propan- or butan-sulfonyl.

Phenoxy-lower alkyl is in particular phenoxy-$C_1$–$C_4$-alkyl and is, for example, phenoxymethyl or 2-phenoxyethyl.

Preferred substituted phenyl $R_1$ is, for example, 3-methylphenyl, 4-methylphenyl, 3,5-dimethylphenyl, 3,5-difluorophenyl, 3,5-dichlorophenyl, 3,5-dibromophenyl, 3,5-di-trifluoromethyl-phenyl, 3,5-dihydroxyphenyl, 2,5-dihydroxyphenyl, 2-, 3- or 4-methoxyphenyl, 3,5-dimethoxyphenyl, 3,5-dinitrophenyl.

In the definition for $R_2$, $R_3$ and $R_3'$ lower alkyl, cycloalkyl, cycloalkyl-lower alkyl, aryl and heteroaryl have the same meanings as defined for corresponding substituent groups for $R_1$.

Extensive pharmacological investigations have shown that the compounds I and their pharmaceutically acceptable salts, for example, have pronounced pharmaceutical, for example, endothelin receptor antagonistic, properties and a beneficial pharmacological profile. The compounds of the present invention bind to both the $ET_A$ and $ET_B$ receptors. Compared to prior art endothelin receptor antagonists, the compounds according to the present invention comprise at most two peptidic bonds. Furthermore, they are distinguished from prior art compounds not only by their unexpected and favorable stability as well as by the pharmacological profile.

The ET receptor antagonists of the present invention are useful for various human diseases caused by ETs, either directly or in concert with other factors. In particular, they are useful for various cardiovascular diseases such as cerebral and coronary vasospasm, cerebral and coronary ischemia, subarachnoidal haemorrhage, various types of hypertension, pulmonary hypertention, cardiac failure, Raynand-syndrome, diabetes, benign prostatic hyperplasia, atherosclerosis or restenosis due to denudation following angioplasty.

The compounds of the present invention also provide a new therapeutic potential for asthma, renal failure, dialysis, glomerular injury, hepatic failure, stomach and duodenal ulcer, ulcus cruris, various brain dysfunctions including migraine, benign prostatic hyperblasia, and occular diseases, glaucoma in particular.

They are also useful to overcome the adverse effects of cyclosporin and can be used for endotoxin shock, or disseminated intravascular coagulation.

The compounds of the formula I and their pharmaceutically acceptable salts can therefore be used, for example, as pharmaceutical active ingredients which are employed, for example, for the treatment of various cardiovascular diseases such as cerebral and coronary vasospasm, cerebral and coronary ischemia, subarachnoidal haemorrhage, various types of hypertension, pulmonary hypertention, cardiac failure, Raynand-syndrome, diabetes, benign prostatic hyperplasia, atherosclerosis or restenosis due to denudation following angioplasty and also for the treatment of asthma, renal failure, dialysis, glomerular injury, hepatic failure, stomach and duodenal ulcer, ulcus cruris, various brain dysfunctions including migraine, benign prostatic hyperblasia, and occular diseases, glaucoma in particular. The invention thus relates to the use of the compounds according to the invention and their pharmaceutically acceptable salts for the production of appropriate medicaments and to the therapeutic treatment of various cardiovascular diseases such as cerebral and coronary vasospasm, cerebral and coronary ischemia, subamchnoidal haemorrhage, various types of hypertension, pulmonary hypertention, cardiac failure, Raynand-syndrome, diabetes, benign prostatic hyperplasia, atherosclerosis or restenosis due to denudation following angioplastyalso for the treatment of asthma, renal failure, dialysis, glomerular injury, hepatic failure, stomach and duodenal ulcer, ulcus cruris, various brain dysfunctions including migraine, benign prostatic hyperblasia, and occular diseases, glaucoma in particular. The industrial production of the active substances is also included in the production of the pharmaceuticals.

The invention relates especially to a compound of formula I wherein

Ar represents a direct bond or arylene;

m is 0, 1,2, or 3;

$R_1$ is lower alkyl, $C_3$–$C_8$-cycloalkyl-lower alkyl, aryl-lower alkyl, $C_3$–$C_8$-cycloalkyl, aryl, aryl-$C_3$–$C_8$-cycloalkyl, lower alkoxy, or aryloxy;

$R_2$ is hydrogen, lower alkyl, aryl-lower alkyl, $C_3$–$C_8$-cycloalkyl, or $C_3$–$C_8$-cycloalkyl-lower alkyl;

$R_3$ represents hydrogen, hydroxy, amino, nitro, lower alkyl, $C_3$–$C_8$-cycloalkyl, or aryl-lower alkyl, provided that Ar is a direct bond, or represents aryl;

$R_3'$ represents hydrogen, lower alkyl, $C_3$–$C_8$-cycloalkyl, aryl-lower alkyl, or aryl; or $R_3$ and $R_3'$ together form fluorenyl, anthryl, or dibenzosuberyl, provided that Ar is a direct bond;

$R_3''$ is hydrogen, lower alkyl or aryl; or $R_2$ and $R_3''$ together form the lower alkylene group —$(CH_2)_n$— wherein n is an integer of 1, 2 or 3; or $R_2$ and $R_3''$ together form a group represented by the formula: —$(CH_2)_o$—$Ar_1$— or —$Ar_1$—$(CH_2)_o$—, respectively, wherein o is zero or an integer of 1 or 2, and $Ar_1$ is arylene;

$C(=X)$ is $C(=O)$, $C(=S)$, $C(=NH)$, $C(=N$-lower alkyl); $C=NH$—OH, or $CH_2$; and Y is a direct bond, —NH—, $$\text{lower alkyl-N} \diagup_{\diagdown}$$

oxygen, or methylene; or $C(=X)$ is CHOH and Y is a direct bond or methylene;

$R_4$ is lower alkyl, lower alkenyl, $C_3$–$C_8$-cycloalkyl, aryl-lower alkyl, aryl-lower alkenyl, or aryl; and $R_5$ is hydrogen, lower alkyl, aryl-lower alkyl, $C_3$–$C_8$-cycloalkyl, or $C_3$–$C_8$-cycloalkyl-lower alkyl; and $R_6$ represents lower alkyl, lower alkenyl, lower alkenyl which substituted by at least one substituent selected from the group consisting of carboxy, lower alkoxycarbonyl, hydroxy, lower alkoxy, amino, lower alkylamino and di-lower alkylamino, halo-lower alkyl, hydroxy-lower alkyl, lower alkanoyl-lower alkyl, phenyl-lower alkanoyl-lower alkyl, benzoyl-lower alkyl, lower alkanesulfonyl-lower alkyl, benzenesulfonyl-lower alkyl, lower alkoxyl-lower alkyl, aryloxy-lower alkyl, aryl-lower alkyl, aryl-lower alkenyl, aryl or lower alkyl which is substituted by carboxy or lower alkoxycarbonyl and also by amino, lower alkylamino or di-lower alkylamino; or $R_5$ and $R_6$ together form the lower alkylene group —$(CH_2)_p$— wherein p is an integer of 3–5, or together form a group represented by the formulae: —$(CH_2)_q$—$Ar_1$— or —$Ar_1$—$(CH_2)_q$—, wherein q is zero or an integer of 1 or 2, and $Ar_1$ is arylene; and $Y_1$ represents —$SO_2$—, —O—, —NH—, —NH—CO—, —NH—CO—O—, or —NH—$SO_2$—; and wherein "arylene", in each case, comprises phenylene, naphthylene or pyridylene; wherein "aryl", in each case, comprises phenyl or naphthyl, thienyl, furanyl, pyrrolyl, 1-lower alkyl-pyrrolyl, pyrazolyl, oxazolyl, isoxazolyl, oxadiazolyl, thiazolyl, isothiazolyl, thiadiazolyl, imidazolyl, 1-lower alkyl-imidazolyl, triazolyl, tetrazolyl, pyrimidyl, pyranyl, pyridyl, indolyl, 1-lower alkyl-indolyl, benzothiophenyl, methylenedioxy-phenyl, benzofuranyl, quinolinyl, or isoquinolinyl; and wherein aryl/arylene radicals or moieties, respectively, are, in each case, unsubstituted or substituted by a radical selected from the group consisting of: halogen, lower alkyl, lower alkoxy, halo-lower alkyl, cyano, amino, hydroxy, phenyl-lower alkoxy, carboxy, lower alkoxycarbonyl, and nitro; or a salt thereof, especially a pharmaceutically acceptable salt thereof.

The invention relates especially to a compound of formula I wherein

Ar represents a direct bond or arylene;

m is 0, 1, 2, or 3

$R_1$ is lower alkyl, $C_3$–$C_8$-cycloalkyl-lower alkyl, aryl-lower alkyl, $C_3$–$C_8$-cycloalkyl, aryl, aryl-$C_3$–$C_8$-cycloalkyl, lower alkoxy, or aryloxy;

$R_2$ is hydrogen, lower alkyl, aryl-lower alkyl, $C_3$–$C_8$-cycloalkyl, or $C_3$–$C_8$-cycloalkyl-lower alkyl;

$R_3$ represents hydrogen, lower alkyl, $C_3$–$C_8$-cycloalkyl, or aryl-lower alkyl, provided that Ar is a direct bond, or represents aryl;

$R_3'$ represents hydrogen, lower alkyl, $C_3$–$C_8$-cycloalkyl, aryl-lower alkyl, or aryl; or $R_3$ and $R_3'$ together form fluorenyl, anthryl, or dibenzosuberyl, provided that Ar is a direct bond;

$R_3''$ is hydrogen, lower alkyl or aryl; or $R_2$ and $R_3''$ together form the lower alkylene group —$(CH_2)_n$— wherein n is an integer of 1, 2 or 3; or $R_2$ and $R_3''$ together form a group represented by the formula: —$(CH_2)_o$—$Ar_1$— or —$Ar_1$—$(CH_2)_o$—, respectively, wherein o is zero or an integer of 1 or 2, and $Ar_1$ is arylene; $C(=X)$ is $C(=O)$, $C(=S)$, $C(=NH)$, $C(=N$-lower alkyl); $C=NH$—OH, or $CH_2$; and Y is a direct bond, —NH—, $$\text{lower alkyl-N} \diagup_{\diagdown}$$

oxygen, or methylene; or $C(=X)$ is CHOH and Y is a direct bond or methylene;

$R_4$ is aryl; and $R_5$ is hydrogen, lower alkyl, aryl-lower alkyl, $C_3$–$C_8$-cycloalkyl, or $C_3$–$C_8$-cycloalkyl-lower alkyl; and $R_6$ represents lower alkyl, halo-lower alkyl, hydroxy-lower alkyl, lower alkanoyl-lower alkyl, phenyl-lower alkanoyl-lower alkyl, benzoyl-lower alkyl, lower alkanesulfonyl-lower alkyl, benzenesulfonyl-lower alkyl, lower alkoxyl-lower alkyl, aryloxy-lower alkyl, aryl-lower alkyl, aryl or lower alkyl which is substituted by carboxy or lower alkoxycarbonyl and also by amino, lower alkylamino or di-lower alkylamino; or $R_5$ and $R_6$ together form the lower alkylene group of —$(CH_2)_p$— wherein p is an integer of 3–5, or together form a group represented by the formulae: —$(CH_2)_q$—$Ar_1$— or —$Ar_1$—$(CH_2)_q$—, wherein q is zero or an integer of 1 or 2, and $Ar_1$ is arylene; and $Y_1$ represents —$SO_2$—, —O—, —NH—, —NH—CO—, —NH—CO—O—, or —NH—$SO_2$—; and wherein "arylene", in each case, comprises phenylene, naphthylene or pyridylene; wherein "aryl", in each case, comprises phenyl or naphthyl, thienyl, furanyl, pyrrolyl, 1-lower alkyl-pyrrolyl, oxazolyl, isoxazolyl, oxadiazolyl, thiazolyl, thiadiazolyl, imidazolyl, 1-lower alkyl-imidazolyl, triazolyl, pyrimidyl, pyranyl, pyridyl, indolyl, 1-lower alkyl-indolyl, benzothiophenyl, benzofuranyl, quinolinyl, or isoquinolinyl; and wherein aryl/arylene radicals or moieties, respectively, are, in each case, unsubstituted or substituted by a radical selected from the group consisting of: halogen, lower alkyl, lower alkoxy, halo-lower alkyl, cyano, amino, hydroxy, phenyl-lower alkoxy, carboxy, lower alkoxycarbonyl, and nitro; or a salt thereof, especially a pharmaceutically acceptable salt thereof.

The invention relates especially to a compound of formula I wherein

Ar represents a direct bond or phenylene;

$R_1$ is mono- or di-substituted phenyl

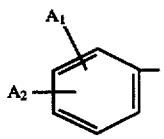

in which one of $A_1$ and $A_2$ is or in which $A_1$ and $A_2$, independently of one another, are halogen, lower alkyl, lower alkoxy, trifluoromethyl, hydroxy, phenyl lower alkoxy, or nitro; or $A_1$ and $A_2$ together form —O—CH$_2$—O—;

$R_2$ is hydrogen or lower alkyl;

$R_3$ represents hydrogen, hydroxy, amino, nitro, phenyl, thienyl, furanyl, pyrrolyl, pyrazolyl, oxazolyl, isoxazolyl, thiazolyl, isothiazolyl, oxadiazolyl, thiadiazolyl, imidazolyl, triazolyl, or pyridyl, each of which is unsubstituted or substituted by halogen, lower alkyl, lower alkoxy, trifluoromethyl, cyano, amino, hydroxy or nitro;

$R_3'$ and $R_3''$, independently of one another, represent hydrogen or phenyl which is unsubstituted or substituted by halogen, lower alkyl, lower alkoxy, trifluoromethyl, cyano, amino, hydroxy, or nitro; or $R_3$ and $R_3'$ together form fluorenyl, anthryl, or dibenzosuberyl, provided that Ar is a direct bond; or $R_2$ and $R_3''$ together form the lower alkylene group —(CH$_2$)$_n$— wherein n is an integer of 1, 2 or 3;

C(=X) is C(=O), C(=NH), C(=N-lower alkyl); and Y is a direct bond, —NH—,

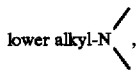

oxygen, or methylene;

$R_4$ represents naphthyl, thienyl, 3,4-methylenedioxyphenyl, indolyl or 1-lower alkyl-indolyl each of which is unsubstituted or substituted by halogen, lower alkyl, lower alkoxy, trifluoromethyl, or hydroxy, and m is 1, 2, or 3; or $R_4$ is lower alkyl, lower alkenyl, C$_3$-C$_8$-cycloalkyl, phenyl-lower alkyl, phenyl-lower alkenyl, or phenyl, and m is 0;

$R_5$ is hydrogen or lower alkyl; and $R_6$ represents lower alkyl, halo-lower alkyl, hydroxy-lower alkyl, lower alkoxy-lower alkyl, phenyl-lower alkyl in which phenyl is unsubstituted or substituted by halogen, lower alkyl, lower alkoxy, trifluoromethyl, or hydroxy; lower alkenyl, lower alkenyl which substituted by at least one substituent selected from the group consisting of carboxy, lower alkoxycarbonyl, hydroxy, lower alkoxy, amino, lower alkylamino and di-lower alkylamino, or represents phenyl-lower alkenyl, phenyl, thienyl, furyl, thiadiazolyl, pyrimidyl or pyridyl, each of which is unsubstituted or substituted by halogen, lower alkyl, lower alkoxy, trifluoromethyl, hydroxy, nitro, carboxy, or lower alkoxycarbonyl; or $R_5$ and $R_6$ together form the lower alkylene group —(CH$_2$)$_p$— wherein p is an integer of 3–5; and $Y_1$ is —SO$_2$—, —O—, —NH—, —NH—CO—, —NH—CO—O—, or —NH—SO$_2$—;

or a salt thereof, especially a pharmaceutically acceptable salt thereof.

The invention relates especially to a compound of formula I wherein

Ar represents a direct bond or phenylene;

$R_1$ is mono- or di-substituted phenyl

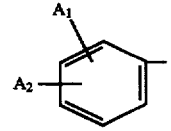

in which one of $A_1$ and $A_2$ is or in which $A_1$ and $A_2$, independently of one another, are halogen, lower alkyl, lower alkoxy, trifluoromethyl, hydroxy, phenyl-lower alkoxy, or nitro;

$R_2$ is hydrogen or lower alkyl;

$R_3$ represents phenyl, thienyl, furanyl, pyrrolyl, isoxazolyl, oxadiazolyl, thiadiazolyl, imidazolyl, or pyridyl, each of which is unsubstituted or substituted by halogen, lower alkyl, lower alkoxy, trifluoromethyl, cyano, amino, hydroxy or nitro;

$R_3'$ and $R_3''$, independently of one another, represent hydrogen or phenyl which is unsubstituted or substituted by halogen, lower alkyl, lower alkoxy, trifluoromethyl, cyano, amino, hydroxy, or nitro; or $R_3$ and $R_3'$ together form fluorenyl, anthryl, or dibenzosuberyl, provided that Ar is a direct bond; or $R_2$ and $R_3''$ together form the lower alkylene group —(CH$_2$)$_n$— wherein n is an integer of 1, 2 or 3;

C(=X) is C(=O), C(=NH), C(=N-lower alkyl); and Y is a direct bond, —NH—,

oxygen, or methylene;

$R_4$ represents indolyl or 1-lower alkyl-indolyl each of which is unsubstituted or substituted by halogen, lower alkyl, lower alkoxy, trifluoromethyl, or hydroxy, and m is 1, 2, or 3

$R_5$ is hydrogen or lower alkyl; and $R_6$ represents lower alkyl, halo-lower alkyl, hydroxy-lower alkyl, lower alkoxy-lower alkyl, phenyl-lower alkyl in which phenyl is unsubstituted or substituted by halogen, lower alkyl, lower alkoxy, trifluoromethyl, or hydroxy; phenyl, thienyl, furyl, thiadiazolyl, pyrimidyl or pyridyl, each of which is unsubstituted or substituted by halogen, lower alkyl, lower alkoxy, trifluoromethyl, hydroxy, carboxy, or lower alkoxycarbonyl; or $R_5$ and $R_6$ together form the lower alkylene group of —(CH$_2$)$_p$— wherein p is an integer of 3–5; and $Y_1$ is —SO$_2$—, —O—, —NH—, —NH—CO—, —NH—CO—O—, or —NH—SO$_2$—;

or a salt thereof, especially a pharmaceutically acceptable salt thereof.

The invention relates especially to a compound of formula I wherein

Ar represents a direct bond or phenylene;

$R_1$ is di-substituted phenyl

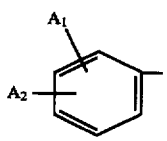

in which $A_1$ and $A_2$, independently of one another, are halogen, lower alkyl, lower alkoxy, trifluoromethyl, hydroxy, phenyl-lower alkoxy, or nitro; or $A_1$ and $A_2$ together form —O—$CH_2$—O—;

$R_2$ is lower alkyl;

$R_3$ represents hydrogen, hydroxy, amino, nitro, phenyl, thienyl, pyridyl, pyrazolyl, isoxazolyl, oxadiazolyl, isothiazolyl, triazolyl, or thiadiazolyl, each of which is unsubstituted or substituted by halogen, lower alkyl, lower alkoxy, trifluoromethyl, cyano, amino, hydroxy, or nitro;

$R_3'$ and $R_3''$, independently of one another, represent hydrogen or phenyl which is unsubstituted or substituted by halogen, lower alkyl, lower alkoxy, trifluoromethyl, cyano, amino, hydroxy, or nitro;

C(=X) is C(=O), C(=NH), C(=N-lower alkyl); and Y is a direct bond, —NH—,

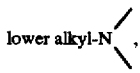

oxygen, or methylene;

$R_4$ represents naphthyl, thienyl, 3,4-methylenedioxyphenyl, indolyl or 1-lower alkyl-indolyl each of which is unsubstituted or substituted by halogen, lower alkyl, trifluoromethyl, lower alkoxy, or hydroxy, and m is 1 or 2; or $R_4$ is lower alkyl, lower alkenyl, phenyl-lower alkyl, $C_5$-$C_6$-cycloalkyl, or phenyl and m is zero;

$R_5$ is hydrogen; and $R_6$ represents lower alkyl, lower alkenyl, halo-lower alkyl, lower alkoxy-lower alkyl, phenyl-lower alkyl or phenyl-lower alkenyl in which phenyl is unsubstituted or substituted by halogen, lower alkyl, trifluoromethyl, lower alkoxy, or hydroxy; lower alkenyl, phenyl or thienyl, each of which is unsubstituted or substituted by halogen, lower alkyl, lower alkoxy, trifluoromethyl, hydroxy, nitro, carboxy, or lower alkoxycarbonyl; and $Y_1$ is —$SO_2$—, —O—, —NH—, —NH—CO—, or —NH—CO—O—;

or a salt thereof, especially a pharmaceutically acceptable salt thereof.

The invention relates especially to a compound of formula I wherein

Ar represents a direct bond or phenylene;

$R_1$ is di-substituted phenyl

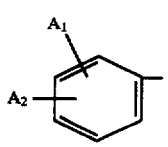

in which $A_1$ and $A_2$, independently of one another, are halogen, lower alkyl, lower alkoxy, trifluoromethyl, hydroxy, phenyl-lower alkoxy, or nitro;

$R_2$ is lower alkyl;

$R_3$ represents phenyl, thienyl, isoxazolyl, oxadiazolyl, or thiadiazolyl, each of which is unsubstituted or substituted by halogen, lower alkyl, lower alkoxy, trifluoromethyl, cyano, amino, hydroxy, or nitro;

$R_3'$ and $R_3''$, independently of one another, represent hydrogen or phenyl which is unsubstituted or substituted by halogen, lower alkyl, lower alkoxy, trifluoromethyl, cyano, amino, hydroxy, or nitro;

C(=X) is C(=O), C(=NH), C(=N-lower alkyl); and Y is a direct bond, —NH—,

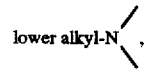

oxygen, or methylene;

$R_4$ represents indolyl or 1-lower alkyl-indolyl each of which is unsubstituted or substituted by halogen, lower alkyl, trifluoromethyl, lower alkoxy, or hydroxy, and m is 1 or 2;

$R_5$ is hydrogen; and $R_6$ represents lower alkyl, halo-lower alkyl, lower alkoxy-lower alkyl, phenyl-lower alkyl in which phenyl is unsubstituted or substituted by halogen, lower alkyl, trifluoromethyl, lower alkoxy, or hydroxy; or represents phenyl or thienyl, each of which is unsubstituted or substituted by halogen, lower alkyl, lower alkoxy, trifluoromethyl, hydroxy, carboxy, or lower alkoxycarbonyl; and $Y_1$ is —$SO_2$—, —O—, —NH—, —NH—CO—, or —NH—CO—O—;

or a salt thereof, especially a pharmaceutically acceptable salt thereof.

The invention relates especially to a compound of formula (Ia)

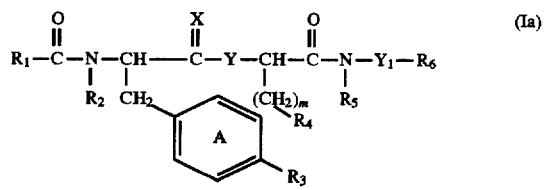

wherein ring A is unsubstituted or substituted by halogen, lower alkyl, lower alkoxy, trifluoromethyl, or hydroxy;

$R_1$ is di-substituted phenyl

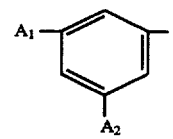

in which $A_1$ and $A_2$, independently of one another, are lower alkyl, trifluoromethyl, lower alkoxy, hydroxy, phenyl-lower alkoxy, or halogen;

$R_2$ is lower alkyl;

$R_3$ represents (i) hydrogen, hydroxy, amino or nitro or (ii) phenyl, thienyl, pyridyl, pyrazolyl, triazolyl, isoxazolyl, or isothiazolyl each of which is unsubstituted or substituted by halogen, lower alkyl, lower alkoxy, trifluoromethyl, cyano, amino, hydroxy, or nitro;

C(=X) is C(=O) or C(=NH), and Y is —NH— or methylene;

R$_4$ represents naphthyl, thienyl, 3,4-methylenedioxyphenyl, or indolyl each of which is unsubstituted or substituted by halogen, lower alkyl, lower alkoxy, trifluoromethyl, or hydroxy, and m is 1 or 2; or R$_4$ is lower alkyl, lower alkenyl, phenyl-lower alkenyl, C$_5$-C$_6$-cycloalkyl, or phenyl, and m is zero;

R$_5$ is hydrogen or lower alkyl;

R$_6$ represents lower alkyl, halo-lower alkyl, lower alkoxy-lower alkyl, lower alkenyl, or phenyl-lower alkenyl, or represents phenyl, or thienyl each of which is unsubstituted or substituted by halogen, lower alkyl, lower alkoxy, trifluoromethyl, hydroxy, nitro, carboxy or lower alkoxycarbonyl; and Y$_1$ is —SO$_2$—, —O—, —NH—, or —NH—CO—;

or a salt thereof, especially a pharmaceutically acceptable salt thereof.

The invention relates especially to a compound of formula (Ia) wherein ring A is unsubstituted or substituted by halogen, lower alkyl, lower alkoxy, trifluoromethyl, or hydroxy;

R$_1$ is di-substituted phenyl

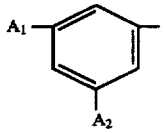

in which A$_1$ and A$_2$, independently of one another, are lower alkyl, trifluoromethyl, lower alkoxy, hydroxy, phenyl-lower alkoxy, or halogen;

R$_2$ is lower alkyl;

R$_3$ represents phenyl, thienyl, or isoxazolyl, each of which is unsubstituted or substituted by halogen, lower alkyl, lower alkoxy, trifluoromethyl, cyano, amino, hydroxy, or nitro;

C(=X) is C(=O) or C(=NH), and Y is —NH— or methylene;

R$_4$ represents indolyl which is unsubstituted or substituted by halogen, lower alkyl, lower alkoxy, trifluoromethyl, or hydroxy, and m is 1 or 2; or R$_5$ is hydrogen or lower alkyl;

R$_6$ represents lower alkyl, halo-lower alkyl or lower alkoxy-lower alkyl, or represents phenyl or thienyl each of which is unsubstituted or substituted by halogen, lower alkyl, lower alkoxy, trifluoromethyl, hydroxy, carboxy or lower alkoxycarbonyl; and Y$_1$ is —SO$_2$—, —O— or —NH—;

or a salt thereof, especially a pharmaceutically acceptable salt thereof.

The invention relates especially to a compound of formula (Ia), wherein ring A is unsubstituted;

R$_1$ is 3,5-di-lower alkyl-phenyl, preferably 3,5-dimethylphenyl;

R$_2$ is C$_1$-C$_4$-alkyl;

R$_3$ represents phenyl, isoxazolyl, preferably 5-isoxazolyl, or thienyl, preferably 3-thienyl, furthermore hydrogen or hydroxy;

C(=X) is C(=O); and Y is —NH—;

R$_4$ represents indolyl, preferably 3-indolyl, and m is 1; or

R$_4$ represents C$_1$-C$_4$-alkyl, preferably methyl, 2-propyl, 2-methyl-1-propyl, or 2-butyl, or C$_2$-C$_4$-alkenyl, preferably, allyl or methallyl, and m is 0;

R$_5$ is hydrogen;

R$_6$ represents C$_1$-C$_4$-alkyl, halo-C$_1$-C$_4$-alkyl, C$_1$-C$_4$-alkoxy-C$_1$-C$_4$-alkyl, phenyl-C$_1$-C$_4$-alkyl, or phenyl or thienyl, preferably 2-thienyl each of which is unsubstituted or substituted by halogen, trifluoromethyl, C$_1$-C$_4$-alkyl, C$_1$-C$_4$-alkoxy, hydroxy, carboxy or C$_2$-C$_5$-alkoxycarbonyl, or represents C$_3$-C$_5$-alkenyl, preferably allyl;

Y$_1$ is —SO$_2$—;

or a salt thereof, especially a pharmaceutically acceptable salt thereof.

The invention relates especially to a compound of formula (Ia), wherein ring A is unsubstituted or substituted by halogen, C$_1$-C$_4$-alkyl, C$_1$-C$_4$-alkoxy, trifluoromethyl, or hydroxy;

m is 1;

R$_1$ is 3,5-di-lower alkyl-phenyl, preferably 3,5-dimethylphenyl;

R$_2$ is C$_1$-C$_4$-alkyl;

R$_3$ represents phenyl, isoxazolyl, preferably 5-isoxazolyl, or thienyl, preferably 3-thienyl;

C(=X) is C(=O); and Y is —NH— or methylene;

R$_4$ represents indolyl, preferably 3-indolyl;

R$_5$ is hydrogen;

R$_6$ represents C$_1$-C$_4$-alkyl, C$_1$-C$_4$-alkoxy-C$_1$-C$_4$-alkyl, or phenyl or thienyl, preferably 2-thienyl each of which is unsubstituted or substituted by halogen, trifluoromethyl, C$_1$-C$_4$-alkyl, C$_1$-C$_4$-alkoxy, hydroxy, carboxy or C$_2$-C$_5$-alkoxycarbonyl; and Y$_1$ is —SO$_2$—;

or a salt thereof, especially a pharmaceutically acceptable salt thereof.

The invention relates especially to a compound of formula (Ia), wherein ring A is unsubstituted;

R$_1$ is 3,5-dimethyl-phenyl;

R$_2$ is C$_1$-C$_4$-alkyl such as methyl or ethyl;

R$_3$ represents 5-isoxazolyl, 3-thienyl or phenyl;

C(=X) is C(=O); and Y is —NH—;

R$_4$ represents 3-indolyl and m is 1; or

R$_4$ represents C$_1$-C$_4$-alkyl, especially 2-propyl or 2-butyl, or C$_2$-C$_4$-alkenyl, preferably, allyl or methallyl, and m is 0;

R$_5$ is hydrogen;

R$_6$ represents C$_1$-C$_4$-alkyl, phenyl or 2-thienyl each of which is unsubstituted or substituted by C$_1$-C$_4$-alkyl, or represents C$_3$-C$_5$alkenyl, especially allyl; and Y$_1$ is —SO$_2$—;

or a salt thereof, especially a pharmaceutically acceptable salt thereof.

The invention relates especially to a compound of formula (Ia), wherein ring A is unsubstituted or substituted by halogen, C$_1$-C$_4$-alkyl, C$_1$-C$_4$-alkoxy, trifluoromethyl, or hydroxy;

m is 1;

R$_1$ is 3,5-dimethyl-phenyl;

R$_2$ is C$_1$-C$_4$-alkyl such as methyl or ethyl;

R$_3$ represents 5-isoxazolyl, 3-thienyl or phenyl;

C(=X) is C(=O); and Y is —NH—;

R$_4$ represents 3-indolyl;

$R_5$ is hydrogen;

$R_6$ represents $C_1$–$C_4$-alkyl, $C_1$–$C_4$-alkoxy-$C_1$–$C_4$-alkyl, or phenyl or 2-thienyl each of which is unsubstituted or substituted by $C_1$–$C_4$-alkyl; and $Y_1$ is —$SO_2$—;

or a salt thereof, especially a pharmaceutically acceptable salt thereof.

The invention relates especially to a compound of formula (Ia), wherein ring A is unsubstituted;

$R_1$ is 3,5-dimethyl-phenyl;

$R_2$ is methyl;

$R_3$ represents 5-isoxazolyl or 3-thienyl;

C(=X) is C(=O); and Y is —NH—;

$R_4$ represents 2-propyl or 2-butyl and m is 0;

$R_5$ is hydrogen;

$R_6$ represents $C_1$–$C_4$-alkyl, preferably n- propyl or n-butyl, allyl, phenyl or 2-thienyl; and $Y_1$ is —$SO_2$—;

or a salt thereof, especially a pharmaceutically acceptable salt thereof.

The invention relates especially to a compound of formula (Ia), wherein ring A is unsubstituted;

$R_1$ is 3,5-dimethyl-phenyl;

$R_2$ is methyl;

$R_3$ represents 5-isoxazolyl or 3-thienyl;

C(=X) is C(=O); and Y is —NH—;

$R_4$ represents 3-indolyl and m is 1;

$R_5$ is hydrogen;

$R_6$ represents n-propyl, n-butyl, allyl, phenyl or 2-thienyl; and $Y_1$ is —$SO_2$—;

or a salt thereof, especially a pharmaceutically acceptable salt thereof.

The invention relates in particular to the novel compounds shown in the examples and to the methods for their preparation described therein.

Preferred stereochemistry is (I')

(Ia')

R/S, if Y is different from —$CH_2$—;
R/R, if Y is —$CH_2$—.

The invention relates to processes for the preparation of the compounds according to the invention. The preparation of compounds of the formula I or Ia, respectively, and their salts comprises, for example, a) reacting a compound of formula (IIa)

or a salt or a reactive acid derivative thereof with a compound of formula HN($R_5$)—$Y_1$—$R_6$ (IIb) or a salt thereof; or b) reacting a compound of formula (IIIa)

with a compound of formula $Z_1$—$Y_1$—$R_6$ (IIIb) in which $Z_1$ represents reactive esterified hydroxy; or, c) for the manufacture of a compound of formula I in which C(=X) is different from methylene or CHOH and in which Y is different from a direct bond or methylene, reacting a compound of formula (IVa)

or a salt or a reactive acid derivative thereof with a compound of formula (IVb)

d) reacting a compound of formula $R_1$—COOH (Va) or a salt or a reactive acid derivative thereof with a compound of formula (Vb)

(Vb)

and, if desired, free functional groups in starting material of each variant, with the exception of those participating in the reaction, being optionally in protected form, and any protecting groups present are removed;

and, if desired, converting a compound I obtainable according to the process or in another manner, in free form or in salt form, into another compound I, separating a mixture of isomers obtainable according to the process and isolating the desired isomer and/or converting a free compound I obtainable according to the process into a salt or converting a salt of a compound I obtainable according to the process into the free compound I or into another salt.

The reactions described above and below in the variants are carried out, for example in the absence or, customarily, in the presence of a suitable solvent or diluent or a mixture thereof, the reaction, as required, being carried out with cooling, at room temperature or with warming, for example in a temperature range from about −80° C. up to the boiling point of the reaction medium, preferably from about −10° to about +200° C., and, if necessary, in a closed vessel, under pressure, in an inert gas atmosphere and/or under anhydrous conditions.

Reactive acid derivatives of compounds of formula IIa or IVa or Va, respectively, are for example derived activated esters or reactive anhydrides, and also reactive cyclic amides. The reactive acid derivatives can be formed in situ.

Activated esters of compounds of formula IIa or IVa or Va, respectively, having a carboxy group are especially esters unsaturated at the linking carbon atom of the esterifying radical, for example of the vinyl ester type, such as vinyl esters (obtainable, for example, by transesterification of a corresponding ester with vinyl acetate; activated vinyl ester method), carbamoyl esters (obtainable, for example, by treatment of the corresponding acid with an isoxazolium reagent; 1,2-oxazolium or Woodward method), or 1-lower alkoxyvinyl esters (obtainable, for example, by treatment of the corresponding acid with a lower alkoxyacetylene; ethoxyacetylene method), or esters of the amidino type, such as N,N'-disubstituted amidino esters (obtainable, for example, by treatment of the corresponding acid with a suitable N,N'-disubstituted carbodiimide, for example N,N'-dicyclohexylcarbodiimide; carbodiimide method), or N,N-disubstituted amidino esters (obtainable, for example, by treatment of the corresponding acid with an N,N-disubstituted cyanamide; cyanamide method), suitable aryl esters, especially phenyl esters suitably substituted by electron-attracting substituents (obtainable, for example, by treatment of the corresponding acid with a suitably substituted phenol, for example 4-nitrophenol, 4-methylsulfonylphenol, 2,4,5-trichlorophenol, 2,3,4,5,6-pentachlorophenol or 4-phenyldiazophenol, in the presence of a condensation agent, such as N,N'-dicyclohexylcarbodiimide; activated aryl esters method), cyanomethyl esters (obtainable, for example, by treatment of the corresponding acid with chloroacetonitrile in the presence of a base; cyanomethyl esters method), thioesters, especially unsubstituted or substituted, for example nitro-substituted, phenylthio esters (obtainable, for example, by treatment of the corresponding acid with unsubstituted or substituted, for example nitro-substituted, thiophenols, inter alia by the anhydride or carbodiimide method; activated thiol esters method), or especially amino or amido esters (obtainable, for example, by treatment of the corresponding acid with an N-hydroxyamino or N-hydroxyamido compound, for example N-hydroxysuccinimide, N-hydroxypiperidine, N-hydroxyphthalimide, N-hydroxy-5-nor-bornene-2,3-dicarboxylic acid imide, 1-hydroxybenzotriazole or 3-hydroxy-3,4-dihydro-1,2,3-benzotriazin-4-one, for example by the anhydride or carbodiimide method; activated N-hydroxy esters method). Internal esters, for example γ-lactones, can also be used.

Anhydrides of acids may be symmetric or preferably mixed anhydrides of those acids, for example anhydrides with inorganic acids, such as acid halides, especially acid fluorides (obtainable, for example by treatment of the corresponding acid with suitable fluorinating agents such as 1,1-difluoro-3-trifluoro-propyleneoxide, 2-fluoro-1,3-dimethyl-pyridinium benzenesulfonate, dimethyldifluoromethyl-amine, benzoylfluoride, perfluoro-2methyldifluoromethyl-amine, hexafluoropropane, trifluorotuoluene/BF$_3$ and pentene, hexafluoropropane, trifluorotuoluene/BF$_3$ and especially cyanuric fluioride), acid chlorides (obtainable, for example, by treatment of the corresponding acid with thionyl chloride, phosphorus pentachloride, phosgene or oxalyl chloride; acid chloride method), azides (obtainable, for example, from a corresponding acid ester via the corresponding hydrazide by treatment thereof with nitrous acid; azide method), anhydrides with carbonic acid semi-esters, for example carbonic acid lower alkyl semi-esters (obtainable, for example, by treatment of the corresponding acid with chloroformic acid lower alkyl esters such as isopropylchlorformate or with a 1-lower alkoxycarbonyl-2-lower alkoxy-1,2-dihydroquinoline; mixed O-alkylcarbonic acid anhydrides method), or anhydrides with dihalogenated, especially dichlorinated, phosphoric acid (obtainable, for example, by treatment of the corresponding acid with phosphorus oxychloride; phosphorus oxychloride method), anhydrides with other phosphoric acid derivatives (for example those obtainable with phenyl-N-phenylphosphoramidochloridate or by reaction of alkylphosphoric acid amides in the presence of sulfonic acid anhydrides and/or racemisation-reducing additives, such as N-hydroxybenzotriazole, or in the presence of cyanophosphonic acid diethyl ester) or with phosphorous acid derivatives, or anhydrides with organic acids, such as mixed anhydrides with organic acids, such as mixed anhydrides with organic carboxylic acids (obtainable, for example, by treatment of the corresponding acid with an unsubstituted or substituted lower alkane- or phenyl-lower alkane-carboxylic acid halide, for example phenylacetic acid chloride, pivalic acid chloride or trifluoroacetic acid chloride; mixed carboxylic acid anhydrides method) or with organic sulfonic acids (obtainable, for example, by treatment of a salt, such as an alkali metal salt, of the corresponding acid with a suitable organic sulfonic acid halide, such as lower alkane- or aryl-, for example methane- or p-toluene-sulfonic acid chloride; mixed sulfonic acid anhydrides method) and symmetric anhydrides (obtainable, for example, by condensation of the corresponding acid in the presence of a carbodiimide or 1-diethylaminopropyne; symmetric anhydrides method).

Suitable cyclic amides are especially amides having five-membered diazacycles of aromatic character, such as amides with imidazoles, for example imidazole (obtainable, for example, by treatment of the corresponding acid with N,N'-carbonyldiimidazole; imidazole method), or pyrazole, for example 3,5-dimethylpyrazole (obtainable, for example, via the acid hydrazide by treatment with acetylacetone; pyrazolide method).

Reactive esterified hydroxy ($Z_1$) is in particular hydroxy esterified with a strong inorganic acid or organic sulfonic acid, for example halogen, such as chlorine, bromine or iodine, sulfonyloxy, such as hydroxysulfonyloxy, halosulfonyloxy, for example fluorosulfonyloxy, lower alkanesulfonyloxy which is unsubstituted or substituted, for example by halogen, for example methane- or trifluoromethanesulfonyloxy, $C_3$–$C_7$-cycloalkanesulfonyloxy, for example cyclohexanesulfonyloxy, or benzenesulfonyloxy which is unsubstituted or substituted, for example by lower alkyl or halogen, for example p-bromobenzene- or p-toluenesulfonyloxy.

Process Variants a), c) and d)

The condensation for forming an amide bond can be carried out in a manner known per se, for example, as described in:

"Houben-Weyl, Methoden der organischen Chemie", 4.ed., Vol. 15/II (1974), Vol. IX (1955), Vol. E11 (1985), Georg Thieme Verlag, Stuttgart;

"The Peptides" (E. Gross and J. Meienhofer, Ed.) Vol. 1 and 2, Academic Press, London and New York, 1979/1980; or "Principles of Peptide Synthesis", M. Bodansky, Springer-Verlag, Berlin, 1984.

For example, the condensation of a free carboxylic acid (IIa, IVa or Va, respectively) with the corresponding amine can be carded out preferably in the presence of one of the customary condensation agents, or using as a corresponding reactive acid derivative carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, 1-(3-dimetylaminopropyl)-3-ethyl-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base is added, preferably a tertiary amine, for example a tri-lower alkylamine having bulky radicals, for example ethyl diisopropylamine or triethylamine, and/or a heterocyclic base, for example 4-dimethylaminopyridine or preferably N-methylmorpholine or pyridine.

The condensation of activated esters, reactive anhydrides or reactive cyclic amides with the corresponding amines is customarily carried out in the presence of an organic base, for example simple tri-lower alkylamines, for example triethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives, derived from the acid of formula IIa, IVa or Va, respectively. The condensation of a free carboxylic acid with the corresponding amine can be carried out preferably in the presence of one of the customary condensation agents, or using carboxylic acid anhydrides or carboxylic acid halides, such as chlorides, or activated carboxylic acid esters, such as p-nitrophenyl esters. Customary condensation agents are, for example, carbodiimides, for example diethyl-, dipropyl-, 1-(3-dimethylaminopropyl)-3-ethyl-carbodiimide or especially dicyclohexylcarbodiimide, also suitable carbonyl compounds, for example carbonylimidazole, 1,2-oxazolium compounds, for example 2-ethyl-5-phenyl-1,2-oxazolium 3'-sulfonate and 2-tert-butyl-5-methylisoxazolium perchlorate, or a suitable acylamino compound, for example 2-ethoxy-1-ethoxycarbonyl-1,2-dihydroquinoline, N,N,N',N'-tetraalkyluronium compounds, such as O-benzotriazol-1-yl-N,N,N',N'-tetramethyluronium hexafluorophosphate, also activated phosphoric acid derivatives, for example diphenylphosphoryl azide, diethylphosphoryl cyanide, phenyl-N-phenylphosphoroamidochloridate, bis(2-oxo-3-oxazolidinyl)phosphinic acid chloride or 1-benzotriazolyloxy-tris(dimethylamino)phosphonium hexafluorophosphate.

If desired, an organic base is added, preferably a tertiary amine, for example a tri-lower alkylamine having bulky radicals, for example ethyl diisopropylamine or triethylamine, and/or a heterocyclic base, for example 4-dimethylaminopyridine or preferably N-methylmorpholine or pyridine.

The condensation reactions when starting from an essentially pure isomeric carboxylic acid fluoride surprisingly result in essentially pure isomeric condensation products without inversion of the optical center.

The condensation of activated esters, reactive anhydrides or reactive cyclic amides with the corresponding amines is customarily carried out in the presence of an organic base, for example simple tri-lower alkylamines, for example ethylamine or tributylamine, or one of the above-mentioned organic bases. If desired, a condensation agent is additionally used, for example as described for free carboxylic acids.

The condensation of acid anhydrides with amines can be effected, for example, in the presence of inorganic carbonates, for example ammonium or alkali metal carbonates or hydrogen carbonates, such as sodium or potassium carbonate or hydrogen carbonate (if desired together with a sulfate).

Carboxylic acid chlorides, for example the chlorocarbonic acid derivatives derived from the acid of formula IIa, IVa or Va, respectively, are condensed with the corresponding amines preferably in the presence of an organic amine, for example the above-mentioned tri-lower alkylamines or heterocyclic bases, where appropriate in the presence of a hydrogen sulfate.

The condensation is preferably carried out in an inert, aprotic, preferably anhydrous, solvent or solvent mixture, for example in a carboxylic acid amide, for example formamide or dimethylformamide, a halogenated hydrocarbon, for example methylene chloride, carbon tetrachloride or chlorobenzene, a ketone, for example acetone, a cyclic ether, for example tetrahydrofuran, an ester, for example ethyl acetate, or a nitrile, for example acetonitrile, or in a mixture thereof, as appropriate at reduced or elevated temperature, for example in a temperature range of from approximately −40° C. to approximately +100° C., preferably from approximately −10° C. to approximately +50° C., and in the case where arylsulfonyl esters are used also at approximately from +100° C. to +200° C., and where appropriate under an inert gas atmosphere, for example a nitrogen or argon atmosphere.

Aqueous, for example alcoholic, solvents, for example ethanol, or aromatic solvents, for example benzene or toluene, may also be used. When alkali metal hydroxides are present as bases, acetone can also be added where appropriate.

The condensation can also be carried out in accordance with the technique known as solid phase synthesis which originates from R. Merrifield and is described, for example, in Angew. Chem. 97, 801-812 (1985), Naturwissenschaften 71, 252-258 (1984) or in R. A. Houghten, Proc. Natl. Acad. Sci. U.S.A. 82, 5131–5135 (1985).

Reactive acid derivatives can also be formed in situ.

Process Variant a)

Dependend on the acidic or basic nature of the starting material of formula (IIb) it may be used in form of an acid addition salt or in form of a salt with a base, for example, as mentioned above. E.g. sulfonamides may be used in form of an alkali metal salt such as a sodium or potassium salt, whereas if an hydoxylamine derivative is used it may be used as hydrohalide such as hydrochloride.

Starting material of formula IIa, especially when Y is =O, =NH or =N-lower alkyl, is accessible, for example, by reacting a compound of formula (IIc)

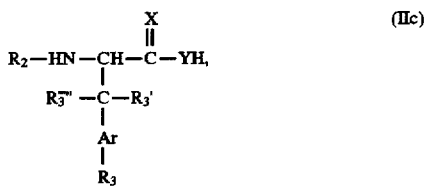

in which the group —C(=X)—YH is preferably protected, e.g. as lower alkyl ester, in a manner as described above, with a compound of formula $R_1$—COOH (IId) or a salt or a reactive acid derivative thereof, e.g. a carboxylic halide thereof, preferably in the presence of a base and/or additionally in the presence of a condensating agent e.g. 1-(3-dimethylaminopropyl)3-ethylcarbodiimide and N-hydroxysuccinimide. In the resulting compounds the carboxy-protecting group is removed in manner known per se, e.g. by hydrolysis with lithium hydroxid.

The resulting compounds of formula

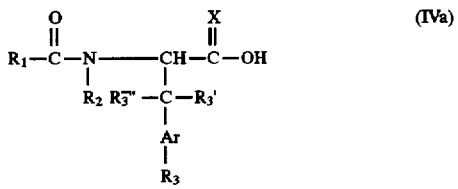

is coupled in a manner known per se, e.g. as described in process variants a), c) and d), with a compound of formula

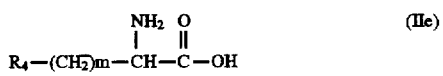

in which the carboxy group may be protected, e.g. as lower alkyl ester, and subsequent removal of the protecting group in the resulting compounds, e.g. by hydrolysis with lithium hydroxid.

A compound of formula IIc in which $R_2$ is hydrogen may optionally be N-alkylated in a manner known per se, e.g. by treating with a compound $R_2$—$Z_1$ in which $Z_1$ represents reactive esterified hydroxy as indicated above, preferably halogen such as bromo, e.g. in the presence of a base, or it may be N-alkylated by reaction with an aldehyde or ketone, for example the N-methylation may be carried out by treatment with formalin in the presence of cyclopentadiene and subsequent treatment with a silane, e.g. triethylsilane, in the presence of a strong acid, e.g. trifluoroacetic acid.

Especially corresponding compounds of formula IIa are obtained in which X and Y are oxygen.

Compounds of formula IIc are either known or may be manufactured in a manner known per se. For example, corresponding compounds in which $R_3$ represents an heterocyclic aryl radical, may be prepared by reacting a compound of formula (IIf)

with glycine in which preferably both the amino and the carboxy group are protected, e.g. in a biphasic system and in the presence of a phase transfer catalyst such as tetrabutylammonium hydrogensulfate, and subsequent removal of the protecting groups.

An alternative method of preparing a compound of formula IIa comprises reacting a compound of formula (IIc)

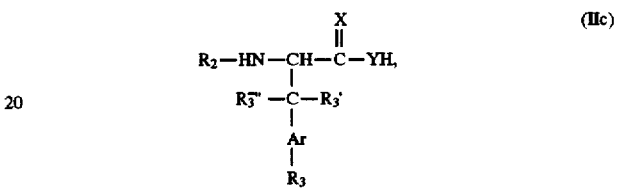

in which Y preferably is =O, =NH or =N-lower alkyl, with a methyl phosphonate, e.g. a di-lower alkyl methyl phosphonate in the presence of a strong basic agent, e.g. 1,8-diazabicyclo[5.4.0]undec-7-ene (DBU), resulting in a compound of formula (IIg)

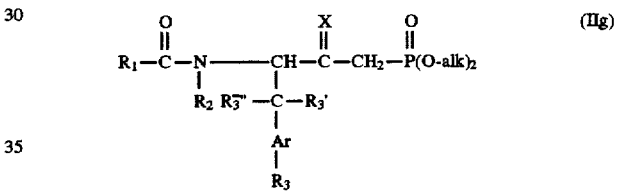

in which alk represents e.g. lower alkyl. Reaction of compounds of the formula (IIg) with a compound of formula (IIe)

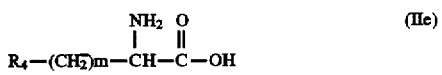

in which the carboxy group preferably is protected, e.g. as lower alkyl ester, under the conditions of the Horner-Emmons reaction results in compounds of formula (IIh)

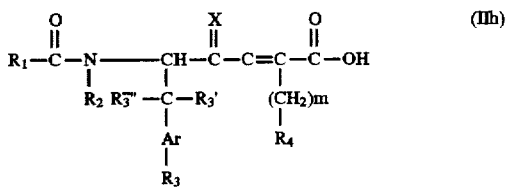

in which the carboxy group preferably is protected. Catalytic hydrogenation, e.g. using Pd or Pt as hydrogenation catalyst, and subsequent removal of the protecting group results in corresponding compounds of formula (IIa).

Starting material of formula (IIb) is either known or can be manufactured in a manner known per se.

Process Variant b).

The reacting is carried out preferably in the presence of a base.

Suitable bases are, for example, alkali metal hydroxides, hydrides, amides, alkanolates, carbonates, triphenylmethylides, di-lower alkylamides, aminoalkylamides or lower alkylsilylamides, naphthaleneamines, lower alkylamines, basic heterocycles, ammonium hydroxides, and carbocyclic amines. Examples which may be mentioned are sodium hydroxide, sodium hydride, sodium amide, sodium methoxide, sodium ethoxide, potassium tert-butoxide, potassium carbonate, lithium triphenylmethylide, lithium diisopropylamide, potassium 3-(aminopropyl) amide, potassium bis(trimethylsilyl)amide, dimethylaminonaphthalene, di- or triethylamine, or ethyldiisopropylamine, N-methylpiperidine, pyridine, benzyltrimethylammonium hydroxide, 1,5-diazabicyclo[4.3.0]non-5-ene (DBN) and 1,8-diaza-bicyclo[5.4.0]undec-7-ene (DBU).

Starting material of formula (IIIa) may be obtained by conventionally forming a carboxylic acid amide with ammonia starting from a compound of formula (IIa)

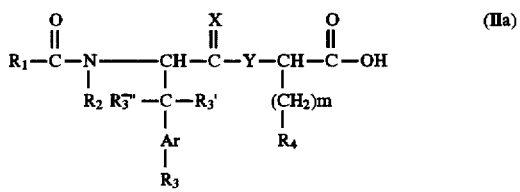

(IIa)

or a salt or a reactive acid derivative thereof.

Starting material of formula (IIIb) is either known or can be manufactured in a manner known per se.

Process Variant c).

Starting material of formula (IVa) may be obtained, for example, in the manner described in process variant a).

The starting material of formula (IVb) may be obtained by reacting a compound of formula (IVc)

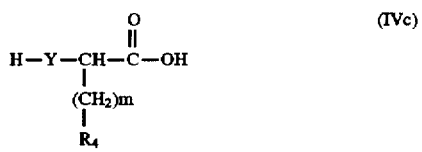

(IVc)

or a salt or reactive acid derivative thereof following the method as described in process variant a) with a compound of formula $HN(R_5)$—$Y_1$—$R_6$ (IIb), e.g. according to the method as described in process variant a). The —YH group in compound (IVc), if Y is nitrogen or oxygen, may be protected and subsequently deprotected in a manner known per se.

The starting material of formula (IVb) wherein Y represents —NH—, especially in form of essentially pure isomers, may be obtained by conversion of a corresponding N-protected compound of formula (IVc) into the corresponding carboxylic acid fluoride, e.g. by treatment with cyanuric fluoride, and subsequent condensation with a N-silylated compound of the formula $(Z_2)(Z_3)(Z_4)N(R_5)$—$Y_1$—$R_6$ (IIb), wherein $Z_2$, $Z_3$ and $Z_4$ independently of one another e.g. represent lower alkyl such as methyl or ethyl. The N-protecting group is removed in conventional manner (BOC by treatment with an acid) resulting in a corresponding compound of formula (IVb).

Process Variant d).

Starting material of formula (Va) is either known or can be manufactured in a manner known per se.

Starting material of formula (Vb) is accessible, for example, by reacting a compound of formula (IVb)

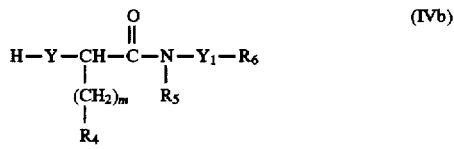

(IVb)

or a salt thereof with a compound of formula (IIc)

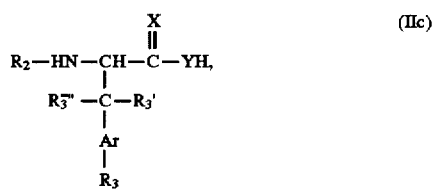

(IIc)

e.g. following the methodology as described in process variant a); the amino group of compound (IIc) may be protected and subsequently be removed in a manner known per se.

Functional groups in starting materials that are not to participate in the reaction, especially carboxy, can be protected by suitable protecting groups (conventional protecting groups) which are customarily used in the synthesis of peptide compounds.

Those protecting groups may already be present in the precursors and are intended to protect the relevant functional groups against undesired secondary reactions, such as acylation, esterification, or solvolysis, etc. In certain cases the protecting groups can additionally cause the reactions to proceed selectively, for example stereoselectively. It is a characteristic of protecting groups that they can be removed easily, i.e. without undesired secondary reactions, for example by solvolysis, reduction, photolysis, and also enzymatically, for example also under physiological conditions. Radicals analogous to protecting groups may, however, also be present in the end products. Hereinbefore and hereinafter, it is protecting groups in the narrower sense that are referred to unless the relevant radicals are present in the end products.

The protection of functional groups by such protecting groups, the protecting groups themselves and the reactions for their removal are described, for example, in standard works such as J. F. W. McOmie, "Protective Groups in Organic Chemistry", Plenum Press, London and New York 1973, in Th. W. Greene, "Protective Groups in Organic Synthesis", Wiley, N.Y. 1981, in "The Peptides"; Volume 3 (E. Gross and J. Meienhofer, eds.), Academic Press, London and New York 1981, in "Methoden der organischen Chemie", Houben-Weyl, 4th edition, Volume 15/I, Georg Thieme Verlag, Stuttgart 1974, in H.-D. Jakubke and H. Jescheit, "Aminosäuren, Peptide, Promine" ("Amino acids, peptides, proteins"), Verlag Chemie, Weinheim, Deerfield Beach and Basel 1982, and in Jochen Lehmann, "Chemie der Kohlenhydrate: Monosaccharide und Derirate" ("The Chemistry of Carbohydrates: monosaccharides and derivatives"), Georg Thieme Verlag, Stuttgart 1974.

A carboxy group is protected, for example, in the form of an ester group which can be removed selectively under mild conditions. A carboxy group protected in esterified form is esterified especially by a lower alkyl group that is preferably branched in the 1-position of the lower alkyl group or substituted in the 1- or 2-position of the lower alkyl group by suitable substituents.

A protected carboxy group esterified by a lower alkyl group is, for example, methoxycarbonyl or ethoxycarbonyl.

A protected carboxy group esterified by a lower alkyl group that is branched in the 1-position of the lower alkyl group is, for example, tert-lower alkoxycarbonyl, for example tert-butoxycarbonyl.

A protected carboxy group esterified by a lower alkyl group that is substituted in the 1- or 2-position of the lower alkyl group by suitable substituents is, for example, arylmethoxycarbonyl having one or two aryl radicals, wherein aryl is phenyl that is unsubstituted or mono-, di- or trisubstituted, for example, by lower alkyl, for example tert-lower alkyl, such as tert-butyl, lower alkoxy, for example methoxy, hydroxy, halogen, for example chlorine, and/or by nitro, for example benzyloxycarbonyl, benzyloxycarbonyl substituted by the mentioned substituents, for example 4-nitrobenzyloxycarbonyl or 4-methoxybenzyloxycarbonyl, diphenylmethoxycarbonyl or diphenylmethoxycarbonyl substituted by the mentioned substituents, for example di(4-methoxyphenyl)methoxycarbonyl, and also carboxy esterified by a lower alkyl group, the lower alkyl group being substituted in the 1- or 2-position by suitable substituents, such as 1-lower alkoxy-lower alkoxycarbonyl, for example methoxymethoxycarbonyl, 1-methoxyethoxycarbonyl or 1-ethoxyethoxycarbonyl, 1-lower alkylthio-lower alkoxycarbonyl, for example 1-methylthiomethoxycarbonyl or 1-ethylthioethoxycarbonyl, aroylmethoxycarbonyl wherein the aroyl group is benzoyl that is unsubstituted or substituted, for example, by halogen, such as bromine, for example phenacyloxycarbonyl, 2-halo-lower alkoxycarbonyl, for example 2,2,2-trichloroethoxycarbonyl, 2-bromoethoxycarbonyl or 2-iodoethoxycarbonyl, as well as 2-(tri-substituted silyl)-lower alkoxycarbonyl wherein the substituents are each independently of the others an aliphatic, araliphatic, cycloaliphatic or aromatic hydrocarbon radical that is unsubstituted or substituted, for example, by lower alkyl, lower alkoxy, aryl, halogen and/or by nitro, for example lower alkyl, phenyl-lower alkyl, cycloalkyl or phenyl each of which is unsubstituted or substituted as above, for example 2-tri-lower alkylsilyl-lower alkoxycarbonyl, such as 2-tri-lower alkylsilylethoxycarbonyl, for example 2-trimethylsilylethoxycarbonyl or 2-(di-n-butyl-methylsilyl)-ethoxycarbonyl, or 2-triarylsilylethoxycarbonyl, such as triphenylsilylethoxycarbonyl.

A carboxy group can also be protected in the form of an organic silyloxycarbonyl group. An organic silyloxycarbonyl group is, for example, a tri-lower alkylsilyloxycarbonyl group, for example trimethylsilyloxycarbonyl. The silicon atom of the silyloxycarbonyl group can also be substituted by two lower alkyl groups, for example methyl groups, and the amino group or the carboxy group of a second molecule of formula I. Compounds having such protecting groups can be prepared, for example, using dimethylchlorosilane as silylating agent.

A protected carboxy group is preferably lower alkoxycarbonyl, for example methoxy-, ethoxy- or tert-butoxycarbonyl, benzyloxycarbonyl, 4-nitrobenzyloxycarbonyl, 9-fluorenylmethoxycarbonyl or diphenylmethoxycarbonyl.

The removal of protecting groups that are not constituents of the desired end product of formula I, for example the carboxy-protecting groups, is effected in a manner known per se, for example by means of solvolysis, especially hydrolysis, alcoholysis or acidolysis, or by means of reduction, especially hydrogenolysis or chemical reduction, as well as by photolysis, as appropriate stepwise or simultaneously, it being possible also to use enzymatic methods. The removal of the protecting groups is described, for example, in the standard works mentioned above in the section relating to "Protecting groups".

For example, protected carboxy, for example lower alkoxycarbonyl, tert-lower alkoxycarbonyl, lower alkoxycarbonyl substituted in the 2-position by a trisubstituted silyl group or in the 1-position by lower alkoxy or lower alkylthio, or unsubstituted or substituted diphenylmethoxycarbonyl can be converted into free carboxy by treatment with a suitable acid, such as formic acid, hydrogen chloride or trifluoroacetic acid, where appropriate with the addition of a nucleophilic compound, such as phenol or anisole. Carboxy can also be freed from lower alkoxycarbonyl by means of bases, such as hydroxides, for example alkali metal hydroxides, such as lithium hydroxide, sodium hydroxide or potassium hydroxide. Unsubstituted or substituted benzyloxycarbonyl can be freed, for example, by means of hydrogenolysis, i.e. by treatment with hydrogen in the presence of a metal hydrogenation catalyst, such as a palladium catalyst. In addition, suitably substituted benzyloxycarbonyl, such as 4-nitrobenzyloxycarbonyl, can also be converted into free carboxy by reduction, for example by treatment with an alkali metal dithionate, such as sodium dithionate, or with a reducing metal, for example zinc, or a reducing metal salt, such as a chromium(II) salt, for example chromium(II) chloride, customarily in the presence of a hydrogen-yielding agent that, together with the metal, is capable of producing nascent hydrogen, such as an acid, especially a suitable carboxylic acid, such as an unsubstituted or substituted, for example hydroxy-substituted, lower alkanecarboxylic acid, for example acetic acid, formic acid, glycolic acid, diphenylglycolic acid, lactic acid, mandelic acid, 4-chloromandelic acid or tartaric acid, or in the presence of an alcohol or thiol, water preferably being added. By treatment with a reducing metal or metal salt, as described above, 2-halo-lower alkoxycarbonyl (where appropriate after conversion of a 2-bromo-lower alkoxycarbonyl group into a corresponding 2-iodo-lower alkoxycarbonyl group) or aroylmethoxycarbonyl can also be converted into free carboxy. Aroylmethoxycarbonyl can also be cleaved by treatment with a nucleophilic, preferably salt-forming, reagent, such as sodium thiophenolate or sodium iodide. 2-(tri-substituted silyl)-lower alkoxycarbonyl, such as 2-tri-lower alkylsilyl-lower alkoxycarbonyl, can also be converted into free carboxy by treatment with a salt of hydrofluoric acid that yields the fluoride anion, such as an alkali metal fluoride, for example sodium or potassium fluoride, where appropriate in the presence of a macrocyclic polyether ("Crown ether"), or with a fluoride of an organic quaternary base, such as tetra-lower alkylammonium fluoride or tri-lower alkylaryl-lower alkylammonium fluoride, for example tetraethylammonium fluoride or tetrabutylammonium fluoride, in the presence of an aprotic, polar solvent, such as dimethyl sulfoxide or N,N-dimethylacetamide. Carboxy protected in the form of organic silyloxycarbonyl, such as tri-lower alkylsilyloxycarbonyl, for example trimethylsilyloxycarbonyl, can be freed in customary manner by solvolysis, for example by treatment with water, an alcohol or an acid, or, furthermore, a fluoride, as described above. Esterified carboxy can also be freed enzymatically, for example by means of esterases or suitable peptidases, for example esterified arginine or lysine, such as lysine methyl ester, using trypsin.

The invention relates in particular to the processes described in the examples.

A compound according to the invention which is obtainable by the process can be converted into another compound according to the invention in a manner known per se.

A compound according to the invention containing hydroxyl can be etherified by methods known per se. The etherification can be carried out, for example, using an alcohol, such as a substituted or unsubstituted lower alkanol, or a reactive ester thereof. Suitable reactive esters of the desired alcohols are, for example, those with strong inorganic or organic acids, such as corresponding halides, sulfates, lower alkanesulfonates or substituted or unsubstituted benzenesulfonates, for example chlorides, bromides, iodides, methane-, benzene- or p-toluenesulfonates. The etherification can be carried out, for example, in the presence of a base, an alkali metal hydride, hydroxide or carbonate, or of an amine. Conversely, corresponding ethers, such as lower alkoxy compounds, can be cleaved, for example, by means of strong acids, such as mineral acids, for example the hydrohalic acids hydrobromic or hydriodic acid, which may advantageously be present in the form of pyridinium halides, or by means of Lewis acids, for example halides of elements of main group III or the corresponding sub-groups. These reactions can be carried out, if necessary, with cooling or warming, for example in a temperature range from about −20° to about 100° C., in the presence or absence of a solvent or diluent, under inert gas and/or under pressure and, if appropriate, in a closed vessel.

If one of the variables contains amino, corresponding compounds of the formula I, their tautomers or salts can be N-alkylated in a manner known per se; likewise, carbamoyl or radicals containing carbamoyl can be N-alkylated. The (aryl)alkylation is carried out, for example, using a reactive ester of an (aryl)$C_1$–$C_7$alkyl halide, for example a bromide or iodide, (aryl)$C_1$–$C_7$alkylsulfonate, for example methanesulfonate or p-toluenesulfonate, or a di-$C_1$–$C_7$alkyl sulfate, for example dimethyl sulfate, preferably under basic conditions, such as in the presence of sodium hydroxide solution or potassium hydroxide solution, and advantageously in the presence of a phase transfer catalyst, such as tetrabutylammonium bromide or benzyltrimethylammonium chloride, where, however, stronger basic condensing agents, such as alkali metal amides, hydrides or alkoxides, for example sodium amide, sodium hydride or sodium ethoxide, may be necessary. Amino can also be acylated in a manner known per se, for example analogously to variant a).

In compounds of the formula I which contain an esterified carboxyl group as a substituent, a group of this type can be converted into a free carboxyl group, for example by means of hydrolysis, for example in the presence of a basic agent, or of an acidic agent, such as a mineral acid. Tert-butyloxycarbonyl, for example, can furthermore be converted into carboxyl, for example in a manner known per se, such as treating with trihaloacetic acid, such as trifluoroacetic acid, and benzyloxycarbonyl can be converted into carboxyl, for example by catalytic hydrogenation in the presence of a hydrogenation catalyst, for example in the manner described below.

Salts of compounds of the formula I can be prepared in a manner known per se. Thus, for example, acid addition salts of compounds of the formula I are obtained by treating with an acid or a suitable ion exchange reagent Salts can be converted into the free compounds in a customary manner, and acid addition salts can be converted, for example, by treating with a suitable basic agent.

Depending on the procedure and reaction conditions, the compounds according to the invention having salt-forming, in particular basic properties, can be obtained in free form or preferably in the form of salts.

In view of the close relationship between the novel compound in the free form and in the form of its salts, in the preceding text and below the free compound or its salts may correspondingly and advantageously also be understood as meaning the corresponding salts or the free compound.

The novel compounds including their salts of salt-forming compounds can also be obtained in the form of their hydrates or can include other solvents used for crystallization.

Depending on the choice of the starting materials and procedures, the novel compounds can be present in the form of one of the possible isomers or as mixtures thereof, for example as pure optical isomers, such as antipodes, or as isomer mixtures, such as racemates, diastereoisomer mixtures or racemate mixtures, depending on the number of asymmetric carbon atoms.

Acid addition salts can be prepared by neutralizing a compound of the formula (I) having a basic group with an acid or an acidic ion exchanger.

Salts with a base can be prepared by neutralizing a compound of the formula (I) having an acidic group with a base compound.

Racemates and diastereomer mixtures obtained can be separated into the pure isomers or racemates in a known manner on the basis of the physicochemical differences of the components, for example by fractional crystallization. Racemates obtained may furthermore be resolved into the optical antipodes by known methods, for example by recrystallization from an optically active solvent, chromatography on chiral adsorbents, with the aid of suitable microorganisms, by cleavage with specific immobilized enzymes, via the formation of inclusion compounds, for example using chiral crown ethers, only one enantiomer being complexed, or by conversion into diastereomeric salts, for example by reaction of a basic final substance racemate with an optically active acid, such as a carboxylic acid, for example tartaric or malic acid, or sulfonic acid, for example camphorsulfonic acid, and separation of the diastereomer mixture obtained in this manner, for example on the basis of its differing solubilities, into the diastereomers from which the desired enantiomer can be liberated by the action of suitable agents. The more active enantiomer is advantageously isolated.

The invention also relates to those embodiments of the process, according to which a compound obtainable as an intermediate in any step of the process is used as a starting material and the missing steps are carried out or a starting material in the form of a derivative or salt and/or its racemates or antipodes is used or, in particular, formed under the reaction conditions.

In the process of the present invention, those starting materials are preferably used which lead to the compounds described as particularly useful at the beginning. The invention likewise relates to novel starting materials which have been specifically developed for the preparation of the compounds according to the invention, to their use and to processes for their preparation. The invention especially relates to novel starting materials of formulae IIa, IIb, IIIa, IIIb, IVa, IVb, Va, and Vb wherein the variables have the meanings as indicated hereinbefore, their manufacture and use, e.g. as starting material.

The invention likewise relates to pharmaceutical preparations which contain the compounds according to the invention or pharmaceutically acceptable salts thereof as active ingredients, and to processes for their preparation.

The pharmaceutical preparations according to the invention which contain the compound according to the invention or pharmaceutically acceptable salts thereof are those for enteral, such as oral, furthermore rectal, and parenteral administration to (a) warm-blooded animal(s), the pharmacological active ingredient being present on its own or together with a pharmaceutically acceptable carrier. The daily dose of the active ingredient depends on the age and the individual condition and also on the manner of administration. The novel pharmaceutical preparations contain, for example, from about 10% to about 80%, preferably from about 20% to about 60%, of the active ingredient.

The pharmacologically active compounds of the invention can be used in the manufacture of pharmaceutical compositions that comprise an effective amount of the same on its own or in conjunction or admixture with excipients or carriers that are suitable for enteral or parenteral administration. Preferred are tablets and gelatin capsules that comprise the active constituent together with a) diluents, for example lactose, dextrose, sucrose, mannitol, sorbitol, cellulose and/or glycine, b) glidants, for example silica, talc, stearic acid, the magnesium or calcium salt thereof and/or polyethylene glycol, for tablets also c) binders, for example magnesium aluminum silicate, starch paste, gelatin, tragacanth, methylcellulose, sodium carboxymethylcellulose and/or polyvinylpyrrolidone, if desired d) dispersing or disintegrating agents, for example Starches, agar, alginic acid or the sodium salt thereof, or foaming mixtures and/or e) absorbents, colouring agents, flavourings and sweeteners. Injectable preparations are preferably aqueous isotonic solutions or suspensions, and suppositories are advantageously produced from fatty emulsions or suspensions. These compositions may be sterilised and/or contain adjuvants, such as preservatives, stabilizers, wetting agents or emulsifiers, solubilisers, salts for regulating the osmotic pressure and/or buffers. In addition they may also contain other therapeutically valuable substances. These preparations are manufactured according to conventional mixing, granulating or coating methods and contain approximately from 0.1 to 100%, preferably approximately from 1 to 50%, of the active constituent. A unit dose for a mammal weighing approximately from 50 to 70 kg may contain between approximately 0.2 and 2000 mg, preferably between approximately 1 and 200 mg, of active constituent.

The following examples illustrate the invention described above; however, they are not intended to limit its extent in any manner. Temperatures are indicated in degrees Celsius.

WORKING EXAMPLES

Example 1

N-Benzenesulfonyl-[N -(3,5-dimethylbenzoyl)-N-methyl-3-biphenyl-4-yl)-(D)-alanyl]-(D,L)-tryptophanamide A solution of the [N-(3,5-dimethylbenzoyl)-N-methyl-3-(biphenyl-4-yl)-(D)-alanyl]-(L)-tryptophan (115 mg, 0.20 mmol) and N-hydroxysuccinimide (28 mg; 0.24 mmol) in dry N,N-dimethylformamide (2 ml) is treated with 1-(3-dimethylaminopropyl)-3-ethylcarbodiimide hydrochloride (46 mg, 0.24 mmol) and stirred at room temperature overnight. The homogeneous mixture is diluted with ethyl acetate (100 ml) and washed with three portions of water (70 ml). The organic layer is dried over magnesium sulfate, filtered and concentrated in vacuo to give the activated ester as a white foam. This material is dissolved in N,N-dimethylformamide (2 ml) at 0° and treated with a solution of potassium benzenesulfonylamide (50 mg; 0.25 mmol) in dimethyl sulfoxide (1 ml). After stirring 1 hour at 0° the reaction mixture is diluted with ethyl acetate (100 ml) and washed with three portions of water (70 ml). The organic layer is dried over magnesium sulfate, filtered and concentrated in vacuo. Chromatography on silica with ethyl acetate/hexane 1:1 (+0.1% acetic acid) gives N-benzenesulfonyl-[N-(3,5-dimethylbenzoyl)-N-methyl-3-(biphenyl-4-yl)-(D)-alanyl]-(D,L)-tryptophanamide as a white foam; FAB-MS m/e 711 (M−H)⁻; NMR (DMSO-d₆, 400 MHz) d [ppm] 7.90 (m), 7.58 (m), 7.46 (m), 7.34 (m), 7.20 (m), 7.07 (t, J=7 Hz), 6.98 (m), 6.50 (m), 4.8 (s, br), 3.4–2.4 (m), 2.19 (s).

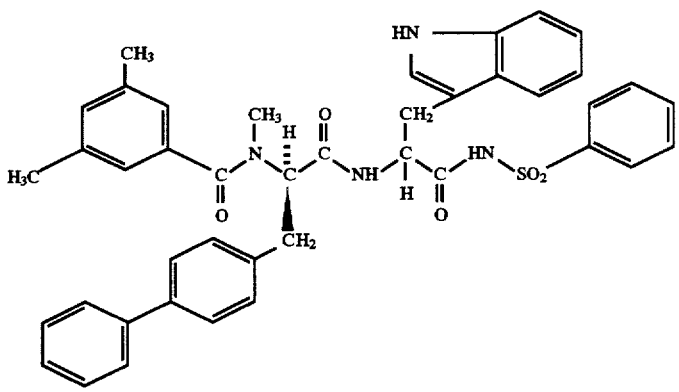

The starting material can be obtained, for example, as follows:

A solution of thionylchloride (6.5 ml) in dry methanol (280 ml) at −20° C. is treated with (D)-3-(biphenyl-4-yl)-alanine (3.7 g, 13.3 retool) (Y. Yabe et al., Chem. Pharm. Bull. 24(12), 3149 (1976)). The reaction mixture is refluxed overnight and concentrated in vacuo. Recrystallization from methanol/ether gives (D)-3-(biphenyl-4-yl)-alanine methyl ester hydrochloride; [α]_D=+13° (c=1.025, methanol).

A solution of (D)-3-(biphenyl-4-yl)-alanine methyl ester hydrochloride (3 15 mg, 0.94 mmol) in dry tetrahydrofuran (0.4 ml) is treated at room temperature with water (0.4 ml), formalin (0.15 ml, 1.88 mmol) and freshly distilled cyclopentadiene (0.3 ml, 3.63 mmol). The slightly yellow solution is stirred at room temperature for 2 hours, washed with hexane (100 ml), diluted with 4% sodium bicarbonate solution (100 ml) and extracted with chloroform (200 ml). The organic layer is dried over magnesium sulfate, filtered and concentrated in vacuo to give a bicyclic intermediate. This material is dissolved at room temperature under nitrogen atmosphere in chloroform (4.7 ml) and treated with trifluoroacetic acid (4.7 ml) and triethylsilane (0.45 ml). The solution is stirred for 20 hours and concentrated in vacuo. The crude product is dissolved in ethyl acetate (200 ml) and washed with 1M hydrochloric acid (100 ml) and saturated sodium bicarbonate solution (100 ml). The organic layer is dried over magnesium sulfate, filtered and concentrated in vacuo to give N-methyl-(D)-3-(biphenyl-4-yl)-alanine methyl ester as a white foam.

A solution of N-methyl-(D)-3-(biphenyl-4-yl)-alanine methyl ester in chloroform (5 ml) is treated with 2M sodium carbonate (0.6 ml) and 3,5-dimethylbenzoyl chloride (0.3 ml, 1.4 mmol). The reaction mixture is stirred at room temperature for 2.5 hours, diluted with ethyl acetate (200 ml) and washed with 4% sodium bicarbonate solution (100 ml), water (100 ml), 1M hydrochloric acid (100 ml) and again water (100 ml). The organic layer is dried over magnesium sulfate, filtered and concentrated in vacuo. Chromatography on silica with ethyl acetate/hexane 4:1 gives N-(3,5-dimethylbenzoyl)-N-methyl-(D)-3-(bi-phenyl-4-yl)-alanine methyl ester $[\alpha]_D=+48°$ (c=0.685, methanol); ee>98% (HPLC: Chiralcel OF).

N-(3,5-Dimethylbenzoyl)-N-methyl-(D)-3-(biphenyl-4-yl)-alanine methyl ester (110 mg, 0.27 mmol) is hydrolized at 0° C. with lithium hydroxide (13 mg, 0.31 mmol) in MeOH (0.8 ml), water (0.4 ml) and tetrahydrofuran (0.4 ml). After 2 hours the reaction mixture is diluted with ether (200 ml) and washed with three portions of water (100 ml). The combined aqueous layers are acidified to pH=2 with 1M hydrochloric acid and extracted with two portions of ethyl acetate (200 ml). The ethyl acetate extracts are dried over magnesium sulfate, filtered and concentrated in vacuo to give N-(3,5-dimethylbenzoyl)N-methyl-(D)-3-(biphenyl-4-yl)-alanine as a white foam; $[\alpha]_D=+7.5°$ (c =1.0, methanol).

A solution of N-(3,5-dimethylbenzoyl)-N-methyl-(D)-3-(biphenyl-4-yl)-alanine (103 mg, 0.27 mmol), (L)-tryptophan methyl ester hydrochloride (100 mg), 0.39 mmol) and hydroxybenztriazole (70 mg, 0.52 mmol) in dry N,N-dimethylformamide (3 ml) is treated with 1-(3-dimethylaminopropyl)-3-ethylcarbodiimide (0.07 ml, 0.38 mmol). The reaction mixture is slowly warmed to room temperature and stirring continued overnight. The homogeneous mixture is diluted with ethyl acetate (100 ml) and washed with three portions of water (70 ml). The organic layer is dried over magnesium sulfate, filtered and concentrated in vacuo. Chromatography on silica with ethyl acetate/hexane 1:1 gives [N-(3,5-dimethylbenzoyl)-N-methyl-(D)-3-(biphenyl-4-yl)-alanyl]-(L)-tryptophan methyl ester as a white foam; de>98% (HPLC: Chiralcel OD). [N-(3,5-dimethylbenzoyl)-N-methyl-(D)-3-(biphenyl-4-yl)-alanyl]-(L)-tryptophan methyl ester is hydrolized at 0° with lithium hydroxide (10 mg, 0.23 mmol) in MeOH (2 ml), tetrahydrofuran (1 ml) and water (1 ml). After 3 hours the reaction mixture is diluted with ether (100 ml) and washed with three portions of water (60 ml). The combined aqueous layers are: acidified to pH=2 with 1M hydrochloric acid and extracted with two portions of ethyl acetate (100 ml). The ethyl acetate extracts are dried over magnesium sulfate, filtered and concentrated in vacuo to give [N-(3,5-dimethylbenzoyl)-N-methyl-(D)-3-(biphenyl-4-yl)-alanyl]-(L)-tryptophan as a white foam; FAB-MS m/e 574 (M+H)$^+$; $[\alpha]_D=+2.50$ (c =1.0, ethanol); NMR (CDCl$_3$, 400 MHz) d [ppm] 8.32 (s), 8.22 (s), 7.6–6.8 (m), 6.93 (s), 6.8 (m), 6.51 (s), 5.97 (s), 5.46 (t, J=8 Hz), 4.85 (q, J=6 Hz), 4.36 (m), 3.4–2.8 (m), 2.73 (s), 2.15 (s), 1.85 (s).

Example 2

N-(2-thienyl)sulfonyl-[N-(3,5-dimethylbenzoyl)-N-methyl-(D)-3-[4-(3-thienyl)phenyl]-alanyl]-(D,L)-tryptophanamide Following the procedure of example 1, [N-(3,5-dimethylbenzoyl)-N-methyl-(D)-3-[4-(3-thienyl)phenyl]-alanyl]-(L)-tryptophan (61 mg 0.11 mmol) is coupled with N-hydroxysuccinimide (61 mg; 0.14 mmol) to give the activated ester as a white foam. Treatment of this material with 2-thienylsulfonylamide (36 mg; 0.22 mmol) in dimethyl sulfoxide/N,N-dimethylformamide in the presence of DBU (45 mg; 0.25 mmol) followed by chromatography of the crude product on silica with ethyl acetate/hexane 1:1 (+0.1% acetic acid) gives N-(2-thienyl)sulfonyl-[N-(3,5-dimethylbenzoyl)-N-methyl-(D)-3-[4-(3-thienyl)phenyl]-alanyl]-(D,L)-tryptophanamide as a white foam; FAB-MS m/e 723 (M–H)$^-$.

The starting material can be obtained, for example, as follows:

[N-(3,5-Dimethylbenzoyl)-N-methyl-(D)-3-[4-(3-thienyl)phenyl]-alanyl]-(L)-tryptophan is synthesized according to example 1 by coupling N-(3,5-dimethylbenzoyl)-N-methyl-(D,L)-3-[4-(3-thienyl)phenyl]-alanine with (L)-tryptophan methyl ester hydrochloride.

Preparative separation of the two diastereomers on HPLC (silica; hexane/isopropanol 20:1) followed by ester hydrolysis gives:

[N-(3,5-dimethylbenzoyl)-N-methyl-(D)-3-[4-(3-thienyl)phenyl]-alanyl]-(L)-tryptophan and [N-(3,5-dimethylbenzoyl)-N-methyl-(L)-3-[4-(3-thienyl)phenyl]-alanyl]-(L)-tryptophan.

N-(3,5-Dimethylbenzoyl)-N-methyl-(D,L)-3-[4-(3-thienyl)-phenyl]-alanine is synthesized from (D,L)-3-[4-(3-thienyl)phenyl]-alanine ethyl ester by coupling with 3,5-dimethylbenzoic acid and subsequent methylation (NaH, MeI, N,N-dimethylformamide).

(D,L)-3-[4-(3-Thienyl)phenyl]alanine ethyl ester is synthesized by alkylation of N-(diphenylmethylene)glycine ethyl ester with 4-(3-thienyl)benzyl bromide (Lit: G. D. Hartmann et al., *J. Org. Chem.*, 51, 142–148 (1986)) in a biphasic system (aqueous sodium hydroxide/dichloromethane) in the presence of a phase transfer catalyst (tetrabutylammonium hydrogensulfate) and subsequent removal of the protecting group (p-toluenesulfonic acid, water, acetonitrile).

Example 3

N-Phenoxy-[N-(3,5-dimethylbenzoyl)-N-methyl-(D)-3-[4-(3-thienyl)phenyl]alanyl]-(L)-tryptophanamide A solution of [N-(3,5-dimethylbenzoyl)-N-methyl-(D)-3-[4-(3-thienyl)phenyl]-alanyl]-(L)-tryptophan (50 mg; 0.09 mmol) and O-phenylhydroxylamine hydrochloride (17 mg; 0.11 mmol) in dry N,N-dimethylformamide (0.5 ml) is treated with 1-(3-dimethylaminopropyl)-3-ethylcarbodiimide (21 ml, 0.11 mmol) and stirred at room temperature overnight. The homogeneous mixture is diluted with ethyl acetate (70 ml) and washed with three portions of 1M hydrocholoric acid (40 ml). The organic layer is dried over magnesium sulfate, filtered and concentrated in vacuo. Preparative TLC on silica with 60 ethyl acetate in petroleum ether gives N-phenoxy-[N-(3,5-dimethylbenzoyl)-N-methyl-(D)-3-[4-(3-thienyl)phenyl]-alanyl]-(L)-tryptophanamide as a white foam; FAB-MS m/e 669 (M–H)$^-$.

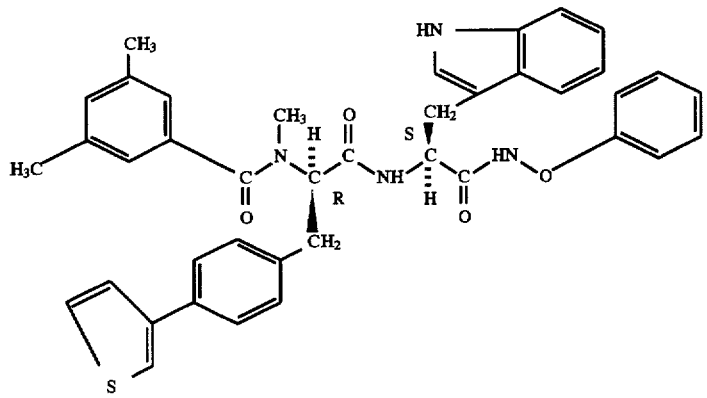

Example 4

N'-Phenyl-[N-(3,5-dimethylbenzoyl)-N-methyl-(D)-3-[4-(3-thienyl)phenyl]-alanyl]-(L)-tryptophanhydrazide Following the procedure of example 3, [N-(3,5-dimethylbenzoyl)-N-methyl-(D)-3-[4-(3-thienyl)phenyl]-alanyl]-(L)-tryptophan (50 mg; 0.09 mmol) is coupled with phenylhydrazine (12 ml; 0. 12 mmol) to give N-phenyl-[N-(3,5-dimethylbenzoyl)-N-methyl-(D)-3-[4-(3-thienyl)phenyl]-alanyl]-(L)-tryptophanhydrazide as a white foam; FAB-MS m/e 668 (M−H)⁻.

indolyl)methyl]-4-oxo-6-(biphenyl-4-yl)-hexanoic acid (50 mg, 0.08 mmol) is coupled with N-hydroxysuccinimide (15 mg; 0.13 mmol) to give 82 mg of the activated ester as a whim foam. Treatment of this matetial with potassium benzenesulfonylamide (15 mg; 0. 16 mmol) in dimethyl sulfoxide/N,N-dimethylformamide followed by chromatography of the crude product on silica with ethyl acetate/hexane 1:1 (+0.1% acetic acid) gives N-benzenesulfonyl-(R)-5-[N-(3,5-dimethylbenzoyl)-N-methyl-amino]-2-(R)-[(3-indolyl)methyl]-4-oxo-6-(biphenyl-4-yl)-hexanoylamide (19 mg, 34%) as a white foam; FAB-MS m/e 710 (M−H)⁻.

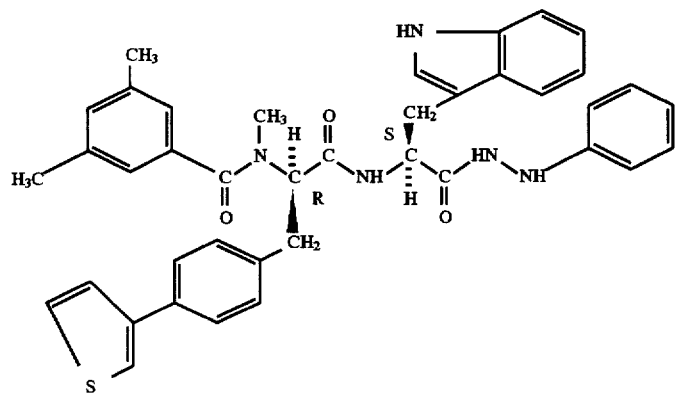

Example 5

N-Benzenesulfonyl-(R)-5-[N-(3,5-dimethylbenzoyl)-N-methyl-amino]-2-(R)-[(3-indol-yl)methyl]4-oxo-6-(biphenyl-4-yl)-hexanoylamide Following the procedure of the preceding examples 5-(R)-[N-(3,5-dimethylbenzoyl)-N-methyl-amino]-2-(R)-[(3-

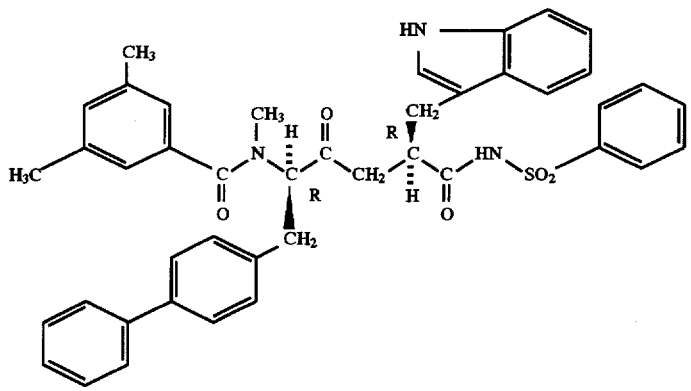

The starting material can be obtained, for example, as follows:

5-(R)-[N-(3,5-Dimethylbenzoyl)-N-methyl-amino]-2-(R)-[(3-indolyl)methyl]-4-oxo-6-(biphenyl-4-yl)-hexanoic acid can be synthesized as follows:

A cooled (–70° C.) solution of dimethyl methylphosphonate (800 mg, 6.4 mmol) in dry tetrahydrofuran (15 ml) under nitrogen is treated with a 1.5M solution of buthyllithium in hexane (4.2 ml, 6.3 mmol). Stirring is continued at –70° C. for 30 minutes. A solution of N-(3,5-dimethylbenzoyl)-N-methyl-(D)-3-(biphenyl-4-yl)-alanine methyl ester (1.04 g, 2.6 mmol) in dry tetrahydrofuran (5 ml) is added dropwise. The colorless reaction mixture is stirred at –70° C. for another 2 hours. The reaction is quenched by addition of 1 ml acetic acid, diluted with ethyl acetate (400 ml) and washed with three portions of water (300 ml). The organic layer is dried over magnesium sulfate, filtered and concentrated in vacuo. The crude material is chromatographed on silica with ethyl acetate to give dimethyl 3-(R)-[N-(3,5-dimethylbenzoyl)-N-methylamino]-2-oxo-4-(biphenyl-4-yl)-1-butylphosphonate as a colorless oil.

To a cooled (0° C.) suspension of sodium hydride (20 mg 60% in oil, 0.5 mmol) in dry tetrahydrofuran (1 ml) under nitrogen atmosphere a solution of dim ethyl 3-(R)-[N-(3,5-dimethylbenzoyl)-N-methyl-amino]-2-oxo-4-(biphenyl-4-yl)-1-butylphosphonate (250 mg, 0.5 mmol) in dry tetrahydrofuran (0.5 ml) is added dropwise. Stirring is continued for 30 minutes. A solution of benzyl indole-3-pyruvate (140 mg, 0.5 mmol; prepared from commercially available indole-3-pyruvic acid and benzyl bromide) in 0.5 mi dry tetrahydrofuran is added dropwise. The reaction mixture is slowly warmed to room temperature and stirring continued overnight. The yellow reaction mixture is diluted with ethyl acetate (100 ml) and washed with three portions of water (70 ml). The organic layer is dried over magnesium sulfate, filtered and concentrated in vacuo. The crude material is chromatographed on silica with ethyl acetate to give a E/Z mixture of products.

The resulting material is hydrogenolized at 5 atm hydrogen pressure in ethanol at 50°–60° C. in the presence of Wilkinson's catalyst [tris(triphenylphosphin)-rhodium(I) chloride]. Chromatography on silica with ethyl acetate/hexane 1:2 gives benzyl 5-(R)-[N-(3,5-dimethylbenzoyl)-N-methyl-amino]-2-(R,S)-[(3-indolyl)methyl]-4-oxo-6-(biphenyl-4-yl)hexanoate as a 2:3 mixture of diastereomers. Separatation of the diastereomers by preparative HPLC (silica, hexane/isopropanol 30:1) followed by hydrogenolytic removal (Pd/C, 1 atm hydrogen) of the benzylester moiety gives 5-(R)-[N-(3,5-dimethylbenzoyl)-N-methylamino]-2-(R)-[(3-indolyl)methyl]-4-oxo-6-(biphenyl-4-yl)hexanoic acid and 5-(R)-[N-(3,5-dimethylbenzoyl)-N-methyl-amino]-2-(S)-[(3-indoly)methyl-4-oxo-6-(biphenyl-4-yl)-hexanoic acid.

Example 6

N-benzenesulfonyl-[N-(3,5-dimethylbenzoyl)-3-[4-(5-isoxazolyl)-phenyl]-(D)-alanyl]-(D,L)-tryptophanamide Under nitrogen atmosphere a solution of [N-(3,5-dimethylbenzoyl)-N-methyl-3-[4-(5-isoxazolyl)-phenyl]-(D)-alanyl]-(L)-tryptophane (340 mg) in ethyl acetate (3.5 ml) is treated with triethylamine (0.096 ml) and isopropylchloroformate (0.077 ml), for 1 hour at room temperature. The solution is filtered under nitrogen and the filtrate added to a solution of potassium benzenesulfonylamide (153 mg) in dimethylsulfoxide (7 ml). After stirring at room temperature for 6 hours the mixture is extracted with ethyl acetate and water, the organic phase washed with brine, dried, and concentrated. Preparative thin layer chromatography on silica gel (hexane/ethyl acetate 1:2+0.1% acetic acid) gives pure N-benzenesulfonyl-[N-(3,5-dimethylbenzoyl)-3-[4-(5-isoxazolyl)-phenyl]-(D)-alanyl]-(D,L)-tryptophanamide; FAB-MS m/e 702 (M–H)⁻.

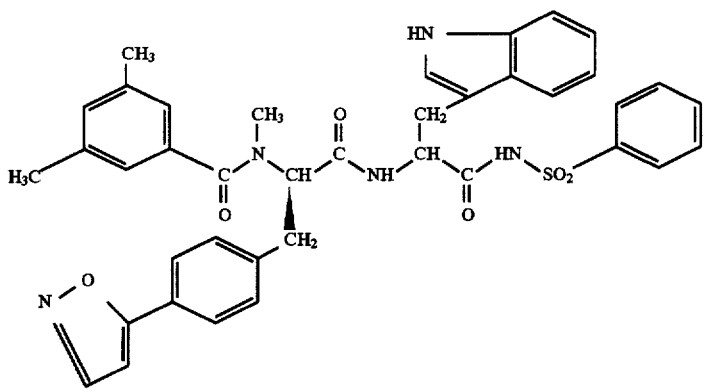

The starting material can be prepared, for example, as follows:

4-Methylacetophenone (100 g) and N,N-dimethylformamide (200 ml) diethylacetal are heated on reflux under nitrogen atmosphere for 20 hours to give, after evaporation, crude 3-dimethylamino-1-p-tolylprop-2-ene-1-one. J. Org. Chem., 45, 4857–60 (1980)

At 0° C. a solution of hydroxylamine-O-sulfonic acid (93 g) in dry methanol (700 ml) is added over 2 min to a solution of crude 3-dimethylamino-1-p-tolylprop-2-en-1-one (148 g) in dry methanol (1 l). The mixture is stirred at ambient temperature for 20 min, then carefully poured into a solution of sodium bicarbonate (150 g) in water (1 l). After standing at room temperature over night (for convenience) the precipitate is collected and dried to give crude 5-(4-methylphenyl)-isoxazole. In order to obtain purer product, the material can be purified by flash cromatography on silica gel, using hexane/ethyl acetate (4:1) as eluent.

To a solution of 5-(4-methylphenyl)-isoxazole (17 g) and N-bromosuccinimide (19 g) in tetrachloromethane (500 ml) under nitrogen, bisbenzoyl peroxide (0.43 g) is added, and the mixture heated on reflux over night. The solvent is evaporated, and the residue purified by flash chromatography (silica gel, hexane/ethyl acetate 4:1) to give pure 5-(4-bromomethylphenyl)-isoxazole.

5-(4-bromomethylphenyl)-isoxazole (700 mg) is dissolved in dichloromethane (20 ml) and stirred vigorously with a solution of tetrabutylammonium hydrogen-sulfate in 2.5 molar aqueous sodium hydroxide, at room temperature, over night. The organic layer is then separated off and concentrated. The residue is partitioned between ether and water, the etherphase washed with water and brine, dried over magnesium sulfate and evaporated to give crude N-diphenylmethylene-3-[4-(5-isoxazolyl)-phenyl]-alanine ethyl ester.

Crude (±)-N-diphenylmethylene-3-[4-(5-isoxazolyl)-phenyl]-alanine ethyl ester (280 mg) was treated with p-toluenesulfonic acid monohydrate (100 mg) in acetonitrile (35 ml) and water (3.5 ml) at ambient temperature for 3.5 hours. After concentration the residue is extracted with ether and 1N sodium hydroxide, washed with brine, dried, and concentrated to give crude 3-[4-(5-isoxazolyl)-phenyl]-alanine ethyl ester.

Crude 3-[4-(5-isoxazolyl)-phenyl]-alanine ethyl ester (660 mg) is dissolved in chloroform (6.6 ml), stirred vigorously with 2N aqueous sodium carbonate (1.4 ml), and after cooling to 10° C., 3,5-dimethylbenzoylchloride (0.7 ml) is added. Stirring is continued for 1 hour at 10° C. and for 2 hours at ambient temperature. Then extraction with dichloromethane/water, washing with 10% aqueous citric acid, and with brine, followed by evaporation gives the crude product. Flash chromatography on silica gel, hexane/ethyl acetate (4:1), gives pure N-(3,5-dimethylbenzoyl)-3-[4-(5-isoxazolyl)-phenyl]-alanine ethyl ester.

A solution of N-(3,5-dimethylbenzoyl)-3-[4-(5-isoxazolyl)-phenyl]-alanine ethyl ester (3.8 g) and methyliodide (1.8 ml) in dry N,N-dimethylformamide (40 ml) is cooled in an ice bath and sodium hydride (60% in oil, 390 mg) is added in portions. The mixture is allowed to warm to room temperature during 5 hours, then poured into water, extracted with ethyl acetate, the organic phase washed with water, and with brine, dried and evaporated. Flash chromatography of the residue on silica gel (hexane/ethyl acetate 3:1) gives pure N-(3,5-dimethylbenzoyl)-N-methyl-3-[4-5-isoxazolyl)-phenyl]-alanine ethyl ester.

N-(3,5-dimethylbenzoyl)-N-methyl-3-[4-(5-isoxazolyl)-phenyl]- alanine ethyl ester (44 mg) is treated with lithium hydroxide monohydrate (5 mg) in methanol (0.5 ml), tetrahydrofurane (0.25 ml), and water (0.25 ml) for 3 hours at room temperature. The mixture is then partitioned between water and ether, the water phase acidified with 1N hydrochloric acid, and subsequently extracted with ethyl acetate. The ethyl acetate phase is washed with brine, dried, and evaporated to give N-(3,5-dimethylbenzoyl)-N-methyl-3-[4-(5-isoxazolyl)-phenyl]-alanine.

At 0° C., N-(3,5-dimethylbenzoyl)-N-methyl-3-[4-(5-isoxazolyl)-phenyl]-alanine (445 mg) is stirred in N,N-dimethylformamide (24 ml) together with (L)-tryptophane methyl ester hydrochloride (400 mg), hydroxybenztriazol (330 mg), and 1-(3-dimethylaminopropyl)-3-ethylcarbodiimide (0.32 ml) for 1 hour and at ambient temperature over night. After extraction with ethyl acetate and 10% aqueous citric acid the organic phase is washed with 4% aqueous sodium bicarbonate, and with brine, dried and evaporated. Flash chromatography on silica gel (hexane/ethyl acetate 2:1) gives the product as a mixture of diastereoisomer. Separation by medium pressure chromatography on a silica gel column, using ether/dichloromethane (1:1) as solvent gives both [N-(3,5-dimethylbenzoyl)-N-methyl-3-[4-(5-isoxazolyl)-phenyl]-(D)-alanyl]-(L)-tryptophane methyl ester, and [N-(3,5-dimethylbenzoyl)-N-methyl-3-[4-(5-isoxazolyl)-phenyl]-(L)-alanyl]-(L)-tryptophane methyl ester.

[N-(3,5-dimethylbenzoyl)-N-methyl-3-[4-(5-isoxazolyl)-phenyl]-(D)-alanyl]-(L)-tryptophane methyl ester (50 mg) is treated with lithiumhydroxide monohydrate (3.8 mg) in methanol (1 ml), tetrahydrofurane (0.5 ml), and water (0.5 ml), at 0° C. for 1 hour, and at room temperature for 2 hours. The mixture is then partitioned between water and ether, the water phase acidified with 1N hydrochloric acid, and subsequently extracted with ethyl acetate. The ethyl acetate phase is washed with brine, dried, and evaporated to give [N-(3,5-dimethylbenzoyl)-N-methyl-3-[4-(5-isoxazolyl)-phenyl]-(D)-alanyl]-(L)-tryptophane.

Example 7

In a manner analogous to that described hereinbefore it is also possible to manufacture the following compounds:

(1) N-benzenesulfonyl-[N-(3,5-dimethylbenzoyl)-N-methyl-3-(biphenyl-4-yl)-(D)-alanyl]-(D,L)-tryptophanamide; FAB-MS m/e 711 (M−H)⁻;

(2) N-propanesulfonyl-[N-(3,5-dimethylbenzoyl)-N-methyl-3-(biphenyl-4-yl)-(D)-alanyl]-(D,L)-tryptophanamide; FAB-MS m/e 677 (M−H)⁻;

(3) N-benzylsulfonyl-[N-(3,5-dimethylbenzoyl)-N-methyl-3-(biphenyl-4-yl)-(D)-alanyl]-(D,L)-tryptophanamide; FAB-MS m/e 725 (M−H)⁻;

(4) N-i-propanesulfonyl-[N-(3,5-dimethylbenzoyl)-N-methyl-3-(biphenyl-4-yl)-(D)-alanyl]-(D,L)-tryptophanamide; FAB-MS m/e 677 (M−H)⁻;

(5) N-(4-methylphenyl)sulfonyl-[N-(3,5-dimethylbenzoyl)-N-methyl-3-(biphenyl-4-yl)-(D)-alanyl]-(D,L)-tryptophanamide; FAB-MS m/e 725 (M−H)⁻;

(6) N-methanesulfonyl-[N-(3,5-dimethylbenzoyl)-N-methyl-(D)-3-(biphenyl-4-yl)-alanyl]-(D,L)-tryptophanamide; FAB-MS role 649 (M−H)⁻;

(7) N-(4-chlorophenyl)sulfonyl-[N-(3,5-dimethylbenzoyl)-N-methyl-(D)-3-(biphenyl-4-yl)-alanyl]-(D,L)-tryptophanamide; FAB-MS role 745 (M−H)⁻;

(8) N-benzenesulfonyl-[N-(3,5-dimethylbenzoyl)-N-methyl-3-phenyl-(D)alanyl]-(D,L)-tryptophanamide; FAB-MS m/e 635 (M−H)⁻;

(9) N-benzenesulfonyl-[N-(3,5-dimethylbenzoyl)-N-methyl-3-(4-hydroxyphenyl)-(D)-alanyl]-(D,L)-tryptophanamide; FAB-MS m/e 653 (M−H)⁻;

(10) N-benzenesulfonyl-[N-(3,5-dimethylbenzoyl)-N-methyl-3-(2-chlorophenyl)-(D)-alanyl]-(D,L)-tryptophanamide; FAB-MS m/e 669 (M−H)⁻;

(11) N-methanesulfonyl-[N-(3,5-dimethylbenzoyl)-N-methyl-3-phenyl-(D)-alanyl]-(D,L)-tryptophanamide; FAB-MS m/e 573 (M−H)⁻;

(12) N-(2-thienyl)sulfonyl-[N-(3,5-dimethylbenzoyl)-N-methyl-3-[4-(3-thienyl)phenyl]-(D)-alanyl]-(D,L)-tryptophanamide; FAB-MS m/e 723 (M−H)⁻;

(13) N-propanesulfonyl-[N-(3,5-dimethylbenzoyl)-N-methyl-3-[4-(3-thienyl)phenyl]-(D)-alanyl]-(D,L)-tryptophanamide; FAB-MS m/e 683 (M−H)⁻;

(14) N-benzenesulfonyl-[N-(3,5-dimethylbenzoyl)-N-methyl-3-[4-(3-thienyl)phenyl]-(D)-alanyl]-(D,L)-tryptophanamide; FAB-MS m/e 717 (M−H)⁻;

(15) N-butanesulfonyl-[N-(3,5-dimethylbenzoyl)-N-methyl-3-[4-(3-thienyl)phenyl]-(D)-alanyl]-(D,L)-tryptophanamide; FAB-MS m/e 697 (M−H)⁻;

(16) N-(2-methylphenyl)sulfonyl-[N-(3,5-dimethylbenzoyl)-N-methyl-3-[4-(3-thienyl)-phenyl]-(D)-alanyl]-(D,L)-tryptophanamide; FAB-MS m/e 731 (M−H)⁻;

(17) N-ethylsulfonyl-[N-(3,5-dimethylbenzoyl)-N-methyl-3-[4-(3-thienyl)phenyl]-(D)-alanyl]-(D,L)-tryptophanamide; FAB-MS m/e 669 (M−H)⁻;

(18) N-(2-ethoxy-ethane)sulfonyl-[N-(3,5-dimethylbenzoyl)-N-methyl-3-[4-(3-thienyl)-phenyl]-(D,L)-alanyl]-(D,L)-tryptophanamide; FAB-MS m/e 713 (M−H)⁻;

(19) N-(2-trifluoro-ethane)sulfonyl-[N-(3,5-dimethylbenzoyl)-N-methyl-3-[4-(3-thienyl)-phenyl]-(D)-alanyl]-(D,L)-tryptophanamide; FAB-MS m/e 723 (M−H)⁻;

(20) N-(4-methoxyphenyl)sulfonyl-[N-(3,5-dimethylbenzoyl)-N-methyl-3-[4-(3-thienyl)-phenyl]-(D)-alanyl]-(D,L)-tryptophanamide; FAB-MS m/e 747 (M−H)⁻;

(21) N-(4-carboxyphenyl)sulfonyl-[N-(3,5-dimethylbenzoyl)-N-methyl-3-[4-(3-thienyl)-phenyl]-(D)-alanyl]-(D,L)-tryptophanamide; FAB-MS m/e 761 (M−H)⁻;

(22) N-(4-ethoxycarbonylphenyl)sulfonyl-[N-(3,5-dimethylbenzoyl)-N-methyl-3-[4-(3-thienyl)phenyl]-(D)-alanyl]-(D,L)-tryptophanamide; FAB-MS m/e 789 (M−H)⁻;

(23) N-(4-fluorophenyl)sulfonyl-[N-(3,5-dimethylbenzoyl)-N-methyl-3-[4-(3-thienyl)-phenyl]-(D)-alanyl]-(D,L)-tryptophanamide; FAB-MS m/e 735 (M−H)⁻;

(24) N-benzenesulfonyl-[N-(3,5-dimethylbenzoyl)-N-methyl-3-[4-(5-isoxazolyl)phenyl]-(D)-alanyl-(D,L)-tryptophanamide; FAB-MS m/e 702 (M−H)⁻;

(25) N-(4-H-1,2,4-triazol-3-sulfonyl)-[N-(3,5-dimethylbenzoyl)-N-methyl-3-[4-(3-thienyl)-phenyl]-(D)- alanyl]-(D,L)-tryptophanamide;

(26) N-benzenesulfonyl-[N-(3,5-dimethylbenzoyl)-N-methyl-3-(4-nitrophenyl)-(D)-alanyl]-(D,L)-tryptophanamide;

(27) N-benzenesulfonyl-[N-(3,5-dimethylbenzoyl)-N-methyl-3-[4-phenoxyphenyl]-(D)-alanyl]-(D,L)-tryptophanamide;

(28) N-benzenesulfonyl-[N-(3,5-dimethylbenzoyl)-N-methyl-3-[4-(3-pyridyl)-phenyl]-(D)-alanyl]-(D,L)-tryptophanamide;

(29) N-(2-hydroxyethanesulfonyl)-[N-(3,5-dimethylbenzoyl)-N-methyl-3-[4-(5-isoxazolyl)-phenyl]-(D)-alanyl]-(D,L)-tryptophanamide;

(30) N-(2-benzyloxyethanesulfonyl)-[N-(3,5-dimethylbenzoyl)-N-methyl-3-[4-(5-isoxazolyl)-phenyl]-(D)-alanyl]-(D,L)-tryptophanamide;

(31) N-(2-pyridinesulfonyl)-[N-(3,5-dimethylbenzoyl)-N-methyl-3-[4-(5-isoxazolyl)-phenyl]-(D)-alanyl]-(D,L)-tryptophanamide;

(32) N-benzenesulfonyl-[N-(3,5-dimethylbenzoyl)-N-methyl-3-[4-(3-imidazolyl)-phenyl]-(D)-alanyl]-(D,L)-tryptophanamide;

(33) N-benzenesulfonyl-N-(3,5-dimethylbenzoyl)-N-methyl-3,4-(1,2,3-thiadiazol-4-yl)-phenyl]-(D)-alanyl]-(D,L)-tryptophanamide;

(34) N-(3-carboxybenzenesulfonyl)-[N-(3,5-dimethylbenzoyl)-N-methyl-3-[4-(5-isoxazolyl)-phenyl]-(D )-alanyl]-(D,L)-tryptophanamide;

(35) N-(3-ethoxycarbonylbenzenesulfonyl)-[N-(3,5-dimethylbenzoyl)- N-methyl-3-[4-(5-isoxazolyl) -phenyl]-(D)-alanyl]-(D,L)-tryptophanamide;

(36) N-(2-carboxybenzenesulfonyl)-[N-(3,5-dimethylbenzoyl)-N-methyl-3-[4-(5-isoxazolyl)-phenyl]-(D)-alanyl]-(D,L)-tryptophanamide;

(37) N-(2-ethoxycarbonylbenzenesulfonyl)-[N-(3,5-dimethylbenzoyl)-N-methyl-3-[4-(5-isoxazolyl)-phenyl]-(D)-alanyl]-(D,L)-tryptophanamide;

(38) N-(2,6-dimethylbenzenesulfonyl)-[N-(3,5-dimethylbenzoyl)-N-methyl-3-[4-(5-isoxazolyl)-phenyl]-(D)-alanyl]-(D,L)-tryptophanamide;

(39) N-(2,6-diethylbenzenesulfonyl)-[N-(3,5-dimethylbenzoyl)-N-methyl-3-[4-(5-isoxazolyl)-phenyl]-(D)-alanyl]-(D,L)-tryptophanamide;

(40) N-(2,6-diisopropylbenzenesulfonyl)-[N-(3,5-dimethylbenzoyl)-N-methyl-3-[4-(5-isoxazolyl)-phenyl]-(D)-alanyl]-(D,L)-tryptophanamide;

(41) N-(3-carboxy-3-aminopropanesulfonyl)-[N-(3,5-dimethylbenzoyl )-N-methyl-3-[4-(5-isoxazolyl)-phenyl]-(D)-alanyl]-(D,L)-tryptophanamide;

(42) N-(2-carboxy-2-aminoethanesulfonyl)-[N-(3,5-dimethylbenzoyl)-N-methyl-3-[4-(5-isoxazolyl)-phenyl]-(D)-alanyl]-(D,L)-tryptophanamide;

(43) N-benzenesulfonyl-[N-(3,5-dimethylbenzoyl)-N-methyl-3-[4-(1,2,4-oxadiazol-3-yl)-phenyl]-(D)-alanyl]-(D,L)-tryptophanamide;

(44) N-benzenesulfonyl-[N-(3,5-dimethylbenzoyl)-N-methyl-3-[4-(3-isoxazoyl)-phenyl]-(D)-alanyl]-(D,L)-tryptophanamide;

(45) N-benzenesulfonyl-[N-(3,5-dimethylbenzoyl)-N-methyl-3-[4-(5-tetrazolyl)-phenyl]-(D)-alanyl]-(D,L)-tryptophanamide;

(46) N-benzenesulfonyl-[N-(3,5-dimethylbenzoyl)-N-methyl-3-[4-(1-H-pyrrol-3-yl)-phenyl]-(D)-alanyl]-(D,L)-tryptophanamide;

(47) N-benzenesulfonyl-[N-(3,5-dimethylbenzoyl)-N-methyl-3-[4-(3-furanyl)-phenyl]-(D)-alanyl]-(D,L)-tryptophanamide;

(48) N'-(4-carboxy-5-trifluoromethylpyrimid-2-yl)-[N-(3,5-dimethylbenzoyl)-N-methyl-(D)-3-[4-(3-thienyl)phenyl]-alanyl]-(L)-tryptophanhydrazide;

(49) N'-(4-methoxycarbonyl-5-trifluoromethylpyrimid-2-yl)-[N-(3,5-dimethylbenzoyl)-N-methyl-(D)-3-[4-(3-thienyl)phenyl]-alanyl]-(L)-tryptophanhydrazide;

(50) N'-(2-chlor-5-carboxyphenyl)-[N-(3,5-dimethylbenzoyl)-N-methyl-(D)-3-[4-(3-thienyl)phenyl]-alanyl]-(L)-tryptophanhydrazide; ( 51) N'-benzoyl-[N-(3,5-dimethylbenzoyl)-N-methyl-(D)-3-[4-(3-thienyl)phenyl]-alanyl]-(L)-tryptophanhydrazide;

(52) N-benzenesulfonyl-N-methyl-[N-(3,5-dimethylbenzoyl)-N-methyl-3-[4-(3-thienyl)-phenyl]-(D)-alanyl]-(D,L)-tryptophanamide;

(53) N'-benzenesulfonyl-[N-(3,5-dimethylbenzoyl)-N-methyl-(D)-3-[4-(3-thienyl)-phenyl]-alanyl]-(L)-tryptophanhydrazide;

(54) N-benzenesulfonyl-[N-(3,5-dimethylbenzoyl)-N-methyl-3-(4-aminophenyl)-(D)-alanyl]-(D,L)-tryptophanamide;

(55) N-benzenesulfonyl-[N-(3,5-dimethylbenzoyl)-N-methyl-3-(4-cyanophenyl)-(D)-alanyl]-(D,L)-tryptophanamide;

(56) N'-butoxycarbonyl-[N-(3,5-dimethylbenzoyl)-N-methyl-(D)-3-[4-(3-thienyl)-phenyl]-alanyl]-(L)-tryptophanhydrazide;

(57) N'-carboxymethoxycarbonyl-[N-(3,5-dimethylbenzoyl)-N-methyl-(D)-3-[4-(3-thienyl)phenyl]-alanyl]-(L)-tryptophanhydrazide;

(58) N'-carboxyacetyl-[N-(3,5-dimethylbenzoyl)-N-methyl-(D)-3-[4-(3-thienyl)phenyl]-alanyl]-(L)-tryptophanhydrazide;

(59) N-benzenesulfonyl-[N-(3,5-dimethylbenzoyl)-3-[4-(5-isoxazolyl)-phenyl]-(D)-alanyl]-(D,L)-tryptophanamide; FAB-MS m/e 702 (M−H)⁻;

(60) N-benzenesulfonyl-[N-3,5-dimethylbenzoyl)-N-methyl-2-methylalanyl]-(L)-tryptophanamide; FAB-MS m/e 573 (M−H)⁻;

(61) N-benzenesulfonyl-[N-(3,5-dimethylbenzoyl)-N-methyl-3-[4-(2-thienyl)-phenyl]-(D)-alanyl]-(D,L)-tryptophanamide; FAB-MS m/e (M+H)⁺;

(62) N-(1,3,4-thiadiazol-2-sulfonyl)-[N-(3,5-dimethylbenzoyl)-N-methyl-3-[4-(3-thien-yl)-phenyl]-(D)-alanyl]-(D,L)-tryptophanamide; FAB-MS m/e 725 (M−H)⁻;

(63) N'-acetyl-[N-(3,5-dimethylbenzoyl)-N-methyl-(D)-3-[4-(3-thienyl)phenyl]-alanyl]-(L)-tryptophanhydrazide; FAB-MS m/e 636 (M+H)⁺;

(64) N'-ethoxycarbonyl-[N-(3,5-dimethylbenzoyl)-N-methyl-(D)-3-[4-(3-thienyl)-phenyl]-alanyl]-(L)-tryptophanhydrazide; FAB-MS m/e 666 (M+H)⁺;

(65) N'-(2-chloro-5-methoxycarbonylphenyl)-[N-(3,5-dimethylbenzoyl)-N-methyl-(D)-3-[4-(3-thienyl)phenyl]-alanyl]-tryptophanhydrazide; FAB-MS m/e 760 (M−H)⁻.

Example 8

N-Butanesulfonyl-[N-(3,5-dimethylbenzoyl)-N-methyl-3-[4-(5-isoxazolyl))-phenyl]-(D,L)-alanyl]-(L)-tryotophanamide To a solution of N-butanesulfonyl-tryptophanamide hydrochloride (0.56 g, 1.55 mmol) and N-(3,5-dimethylbenzoyl)-N-methyl-3-[4-(5-isoxazolyl)-phenyl]-(D,L)-alanine (prepared according to the procedure described in example 6) (0.63 g, 1.66 mmol) in N,N-dimethylformamide (20 ml) are added 1-hydroxybenzotriazole (0.31 g, 2.29 mmol) and 1-(3-dimethylaminopropyl)-3-ethyl-carbodiimide (0.32 ml, 1.75 mmol) at room temperature under nitrogen atmosphere and the mixture is stirred for 18 hours. The reaction mixture is diluted with 10% citric acid and extracted with ethyl acetate. The organic layer is washed with 4% sodium bicarbonate and brine, dried over magnesium sulfate, and concentrated in vacuo. The crude material is chromatographed on silica gel with ethyl acetate/hexane (2:3) and trace of acetic acid to give N-butanesulfonyl-[N-(3,5-dimethylbenzoyl)-N-methyl-3-[4-(5-isoxazolyl)-phenyl]-(D,L)-alanyl]-(L)-tryotophanamide.

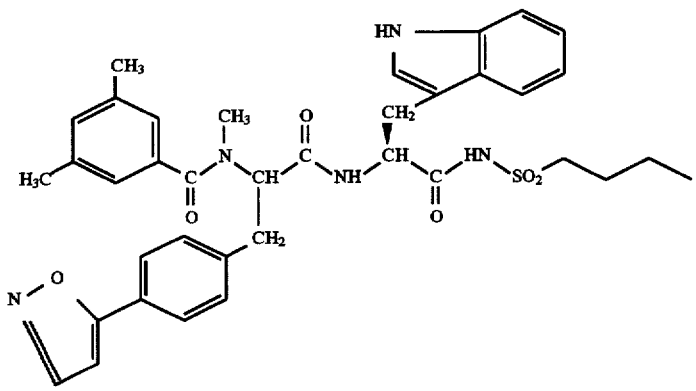

The starting material can be obtained, for example, as follows:

Ammonia gas is bubbled into a solution of 1-butanesulfonyl chloride (2 g, 12.8 mmol) in acetonitrile (20 ml) at room temperature for 30 minutes. The mixture is filtered and the filtrate is concentrated in vacuo. The residue is diluted with water (20 ml) and extracted with ethyl acetate. The organic layer is dried over magnesium sulfate and concentrated in vacuo to give 1-butanesulfonylamide as colorless oil.

A solution of 1-butanesulfonylamide obtained above, triethyl amine (1.84 ml, 13.2 mmol), and chlorotrimethylsilane (1.60 ml, 12.6 mmol) in toluene (30 ml) is refluxed under nitrogen atmosphere for 4 hours. The mixture is filtered and the filtrate is concentrated in vacuo to give N-butanesulfonyl-N-trimethylsilylamide as brown oil.

To a cooled (-15° C.) solution of t-butoxycarbonyltryptophan (1.2 g, 4 mmol) and pyridine (0.35 ml, 4 mmol) in methylene chloride (10 ml) is dropped cyanuric fluoride (0.72 ml, 36 mmol) and the mixture is stirred at -15° C. for 1 hour. The reaction mixture is diluted with methylene chloride and ice, and filtered on Celite. The filtrate is diluted with ice water and extracted with methylene chloride. The organic layer is dried over magnesium sulfate and concentrated in vacuo to give t-butoxycarbonyltryptophan fluoride.

A solution of N-butanesulfonyl-N-trimethylsilylamide (0.75 g, 3.6 mmol), t-butoxycarbonyltryptophan fluoride (0.92 g, 3.01 mmol), and dimethylaminopyridine (37 mg, 0.3 mmol) in tetrahydrofuran (10 ml) is stirred at room temperature for 2 hours. The mixture is diluted with 10% citric acid and extracted with ethyl acetate. The organic layer is washed with water and brine, dried over magnesium sulfate, and concentrated in vacuo. The crude material is chromatographed on silica gel with ethyl acetate/hexane (1:1) and trace of acetic acid to give N-butanesulfonyl-(t-butoxycarbonyl)tryptophanamide.

To a solution of N-butanesulfonyl-(t-butoxycarbonyl)tryptophanamide (0.71 g, 1.68 mmol) and dithiothreitol (47 mg, 0.3 mmol) in 1,4-dioxane (4 ml) is added 4N HCl/1,4-dioxane (20 ml) at more temperature under nitrogen atmosphere and the mixture is stirred for 18 hours. The reaction mixture is concentrated in vacuo and the solid residue is washed with diethyl ether and dried to give N-butanesulfonyl-tryptophanamide hydrochloride.

Example 9

N-(2-Propene)sulfonyl-[N-(3,5-dimethylbenzoyl)-N-methyl-3-[4-(5-isoxazolyl)-phenyl]-(D,L) -alanyl]-(L)-tryptophanamide To a solution of N-(2-propene)sulfonyl-tryptophanamide hydrochloride (103 mg, 0.3 mmol) and N-(3,5-dimethylbenzoyl)-N-methyl-3-[4-(5-isoxazolyl)-phenyl]-(D,L)-alanine (prepared according to the procedure described in example 6) (102 mg, 0.27 mmol) in N,N'-dimethylformamide (10 ml) are added 1-hydroxybenzotriazole (71 mg, 0.524 mmol) and 1-(3-dimethylaminopropyl)-3-ethyl-carbodiimide (58 μl, 0.31 mmol) at more temperature under nitrogen atmosphere and the mixture is stirred for 18 hours. The reaction mixture is diluted with 10% citric acid and extracted with ethyl acetate. The organic layer is washed with 4% sodium bicarbonate and brine, dried over magnesium sulfate, and concentrated in vacuo. The crude material is chromatographed on silica gel with ethyl acetate/hexane (2:3) and trace of acetic acid to give N-(2-propene)sulfonyl-[N-(3,5-dimethylbenzoyl)-N-methyl-3-[4-(5-isoxazolyl)-phenyl]-(D,L)-alanyl]-(L)-tryptophanamide.

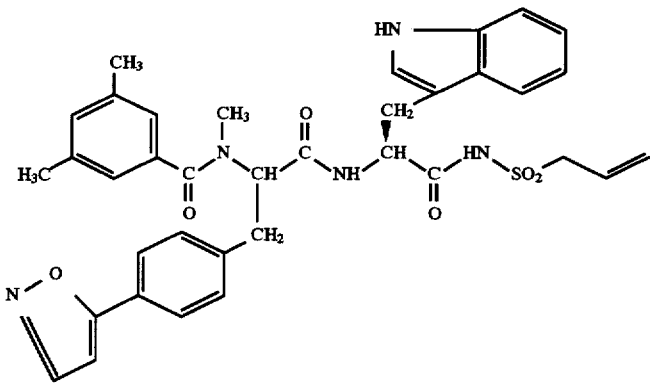

The starting material can be obtained, for example, as follows:

A solution of (2-propene)sulfonylamide (prepared according to the reported procedure: J. F. King, D. R. K. Harding, J. Am. Chem. Soc., 1976, 98, 3312) (1.1 g, 9.1 mmol), chlorotrimethylsilane (1.3 ml, 10.2 mmol), and triethylamine (1.4 ml, 10 mmol) in toluene (50 ml) is refluxed under nitrogen atmosphere for 4 hours. The mixture is filtered and the filtrate is concentrated in vacuo to give N-(2-propene)-N-trimethylsilylamide as brown oil.

A solution of N-(2-propene)-N-trimethylsilylamide (280 mg, 1.39 mmol), t-butoxycarbonyltryptophan fluoride (prepared according to the procedure described in Example 8) (277 mg, 0.904 mmol), and dimethylaminopyridine (45 mg, 0.37 mmol) in tetrahydrofuran (20 ml) is stirred at room temperature for 3 hours. The mixture is diluted with 10% citric acid and extracted with ethyl acetate. The organic layer is washed with water and brine, dried over magnesium sulfate, and concentrated in vacuo. The crude material is chromatographed on silica gel with ethyl acetate/hexane (2:1) and trace of acetic acid to give N-(2-propene)sulfonyl-(t-butoxycarbonyl)tryptophanamide.

To a solution of N-(2-propene)sulfonyl-(t-butoxycarbonyl)tryptophanamide (214 mg, 0.525 mmol) and dithiothreitol (32 mg, 0.21 mmol) in 1,4-dioxane (4 ml) is added 4N HCl/1,4-dioxane (16 ml) at room temperature under nitrogen atmosphere and the mixture is stirred for 4 hours. The reaction mixture is concentrated in vacuo and the solid residue is washed with diethyl ether and dried to give N-(2-propene)sulfonyl-tryptophanamide hydrochloride.

Example 10

N-Butanesulfonyl-[N-(3,5-dimethylbenzoyl)-N-methyl-3-[4-(5-isoxazolyl)-phenyl](D,L)-alanyl]-(L)-isoleucineamide To a solution of N-butanesulfonyl-isoleucineamide hydrochloride (0.124 g, 0.43 mmol) and N-(3,5-dimethylbenzoyl)-N-methyl-3-[4-(5-isoxazolyl)-phenyl]-(D,L)-alanine (prepared according to the procedure in example 6) (0.178 g, 0.47 mmol) in N,N'-dimethylformamide (5 ml) are added 1-hydroxybenzotriazole (90 mg, 0.67 mmol) and 1-(3-dimethylaminopropyl)-3-ethyl-carbodiimide (90 μl, 0.49 mmol) at room temperature under nitrogen atmosphere and the mixture is stirred for 18 hours. The reaction mixture is diluted with 10% citric acid and extracted with ethyl acetate. The organic layer is washed with 4% sodium bicarbonate and brine, dried over magnesium sulfate, and concetrated in vacuo. The crude material is chromatographed on silica gel with ethyl acetate/hexane (1:1) and trace of acetic acid to give N-butanesulfonyl-[N-(3,5-dimethylbenzoyl)-N-methyl-3-[4-(5-isoxazolyl)-phenyl]-(D,L)-alanyl]-(L)-isoleucineamide.

8) (0.64 g, 3.06 mmol), t-butoxycarbonylisoleucine fluoride (0.475 g, 2.04 mmol), and dimethylaminopyridine (110 mg, 0.9 mmol) in tetrahydrofuran (7 ml) is stirred at room temperature for 2 hours. The mixture is diluted with 10% citric acid and extracted with ethyl acetate. The organic layer is washed with water and brine, dried over magnesium sulfate, and concentrated in vacuo. The crude material is chromatographed on silica gel with ethyl acetate/hexane (4:1) to give N-butanesulfonyl-(t-butoxycarbonyl) isoleucineamide.

To a solution of N-butanesulfonyl-(t-butoxycarbonyl) isoleucineamide (0.43 g, 1.23 mmol) and dithiothreitol (47 mg, 0.3 mmol) in 1,4-dioxane (4 ml) is added 4N HCl/1,4-dioxane (20 ml) at room temperature under nitrogen atmosphere and the mixture is stirred for 18 hours. The reaction mixture is concentrated in vacuo and the solid residue is washed with diethyl ether and dried to give N-butanesulfonyl-isoleucineamide hydrochloride.

Example 11

N-Butanesulfonyl-[N-(3,5-dimethylbenzoyl)-N-methyl-3-[4-(5-isoxazolyl)-phenyl]-(D,L)-alanyl]-(L)-valineamide To a solution of N-butanesulfonyl-valineamide hydrochloride (0.52 g, 1.91 mmol) and N-(3,5-dimethylbenzoyl)-N-methyl-3-[4-(5-isoxazolyl)-phenyl]-(D,L)-alanine (prepared according to the procedure in example 6) (0.66 g,

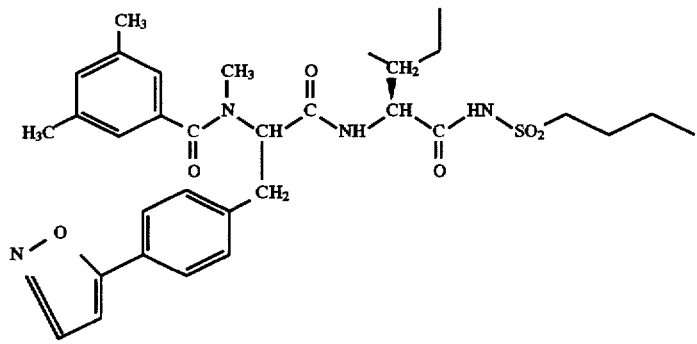

The starting material can be obtained, for example, as follows;

To a cooled (−15° C.) solution of t-butoxycarbonylisoleucine (0.482 g, 2 mmol) and pyridine (0.16 ml) in methylene chloride (5 ml) is dropped cyanuric fluoride (0.9 ml) and the mixture is stirred at −15° C. for 1 hour. The reaction mixture is diluted with methylene chloride and ice, and filtered on Celite. The filtrate is diluted with ice water and extracted with methylene chloride. The organic layer is dried over magnesium sulfate and concentrated in vacuo to give t-butoxycarbonylisoleucine fluoride.

A solution of N-butanesulfonyl-N-trimethylsilylamide (prepared according to the procedure described in Example 1.74 mmol) in N,N'-dimethylformamide (17 ml) are added 1-hydroxybenzotriazole (0.469 g, 3.47 mmol) and 1-(3-dimethylaminopropyl)-3-ethyl-carbodiimide (0.324 g, 2.08 mmol) at room temperature under nitrogen atmosphere and the mixture is stirred for 20 hours. The reaction mixture is diluted with 10% citric acid and extracted with ethyl acetate. The organic layer is washed with 4% sodium bicarbonate and brine, dried over magnesium sulfate, and concentrated in vacuo. The crude material is chromatographed on silica gel with ethyl acetate/hexane (1:1) to give N-butanesulfonyl-[N-(3,5-dimethylbenzoyl)-N-methyl-3-[4-(5-isoxazolyl)-phenyl]-(D,L)-alanyl]-(L)-valineamide.

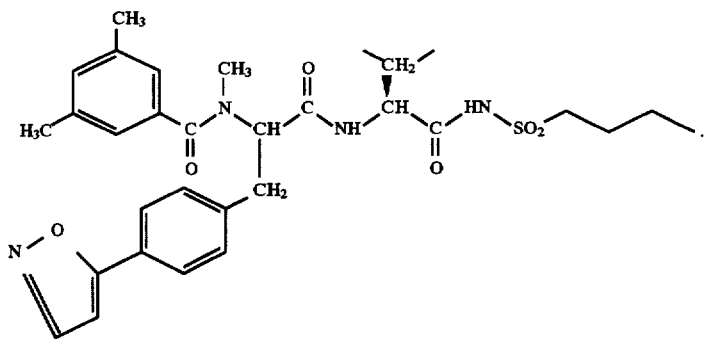

The starting material can be obtained, for example, as follows:

To a cooled (−15° C.) solution of t-butoxycarbonylvaline (1.0 g, 4.6 mmol) and pyridine (0.39 ml) in methylene chloride (11 ml) is dropped cyanuric fluoride (1.87 g, 13.8 mmol) and the mixture is stirred at −15° C. for 1 hour. The reaction mixture is diluted with methylene chloride and ice, and filtered on Celite. The filtrate is diluted with ice water and extracted with methylene chloride. The organic layer is dried over magnesium sulfate and concentrated in vacuo to give t-butoxycarbonylvaline fluoride.

A solution of N-butanesulfonyl-N-trimethylsilylamide (prepared according to the procedure described in Example 8) (1.72 g, 8.28 mmol), t-butoxycarbonylvaline fluoride (1.01 g, 4.6 mmol), and dimethylaminopyridine (220 mg, 1.84 mmol) in tetrahydrofuran (25 ml) is stirred at room temperature for 1 hour. The mixture is diluted with 10% citric acid and extracted with ethyl acetate. The organic layer is washed with water and brine, dried over magnesium sulfate, and concentrated in vacuo. The crude material is chromatographed on silica gel with ethyl acetate/hexane (3:1) to give N-butanesulfonyl-(t-butoxycarbonyl) valineamide.

To a solution of N-butanesulfonyl-t-(butoxycarbonyl) valineamide (0.70 g 2.08 mmol) in 1,4-dioxane (25 ml) is added 4N HCl/1,4-dioxane (30 ml) at room temperature under nitrogen atmosphere and the mixture is stirred for 8 hours. The reaction mixture is concentrated in vacuo and the solid residue is washed with diethyl diethyl ether and dried to give N-butanesulfonyl-isoleucineamide hydrochloride. Tablets, each containing 50 mg of active ingredient, for example, [N-(3,5-dimethylbenzoyl)-N-methyl-3-[4-(5-isoxazolyl)-phenyl]-(D)-alanyl]-(D,L)-tryptophane, can be prepared as follows:

Example 12

N-Butanesulfonyl-[N-(3,5-dimethylbenzoyl)-N-dimethyl-3-[4-(1,2,4-triazol-1-yl)-phenyl]-(D,L)-alanyl]-(L)-tryptophanamide To a stirred solution of N-(3,5-dimethylbenzoyl)-N-methyl-3-[4-(1,2,4-triazol-1-yl)-phenyl]-(D,L)-alanine (60 mg, 0.16 mmol) in N,N'-dimethylformamide under nitrogen atmosphere are added N-butanesulfonyl-tryptophanamide hydrochloride (93 mg, 0.21 mmol) and 1-hydroxybenzotriazole (47 mg, 0.35 mmol). The mixture is cooled to 0° C. and 1-(3-dimethylaminopropyl)-3-carbodiimide (0.047 ml, 0.26 mmol) is added dropwise. After 2 h, the reaction mixture is slowly warmed to room temperature and stirring is continued overnight. The mixture is diluted with ethyl acetate and washed with two portions of water and with brine. The organic layer is dried over sodium sulfate and concentrated in vacuo. The crude material is purified by preparative thin layer chromatography with methylene chloride/methanol/acetic acid (180:20:0.5) to give N-butanesulfonyl-[N-(3,5-dimethylbenzoyl)-N-methyl-3-[4-(1,2,4-triazol-1-yl)-phenyl]-(D,L)-alanyl]-(L)-tryptophanamide

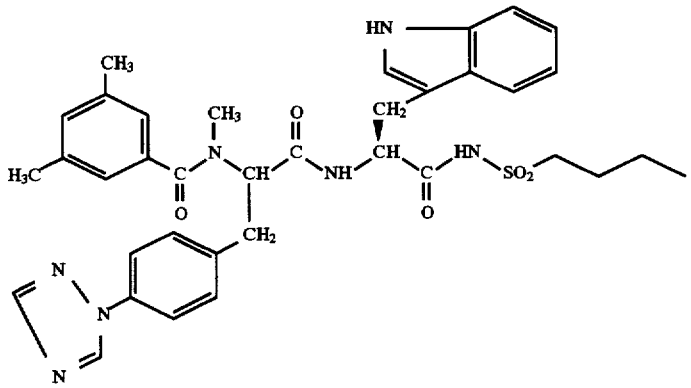

The starting material can be obtained, for example, as follows:

A mixture of 3,5-dimethylbenzamide (22.6 g, 0.15 mol) and glyoxylic acid monohydrate (15.3 g, 0.17 mol) in acetone (120 ml) is heated under nitrogen atmosphere at reflux for 6 h. The solvent is evaporated in vacuo to give 2-hydroxy-N-(3,5-dimethylbenzoyl)glycine. To a solution of 2-hydroxy-N-(3,5-dimethylbenzoyl)glycine in methanol (350 ml) is added concentrated sulfuric acid (4.6 ml) at room temperature. The mixture is stirred for 2 days and then concentrated in vacuo. The residue is diluted with ethyl acetate, washed with two portions of saturated sodium bicarbonate solution and with two portions of brine. The organic layer is dried over magnesium sulfate and concentrated in vacuo to give 2-methoxy-N-(3,5-dimethylbenzoyl) glycine methyl ester.

To a solution of 2-methoxy-N-(3,5-dimethylbenzoyl) glycine methyl ester (16.7 g, 66.5 mmol) in toluene (70 ml) under nitrogen atmosphere is added phosphorus thrichloride (6.0 ml, 68.7 mmol) at room temperature. The reaction mixture is heated at 70° C. for 16 h. Then, trimethyl phosphite (8.1 ml, 68.7 mmol) is added dropwise to the stirred mixture at 70° C. and stirring is continued for further 2 h at 70° C. The solvent is evaporated in vacuo. The residue is diluted with hexane, filtered, and washed with ethyl acetate. The combined filtrate is concentrated in vacuo and the crude material is purified by column chromatography on silica with ethyl acetate to give trimethyl 2-(3,5-dimethylbenzoyl)amino-phosphonoacetate.

A mixture of 1,2,4-triazole (4.06 g, 58.7 mmol), potassium carbonate (9.05 g, 65.5 mmol), 4-fluorobenzaldehyde (6.3 ml, 58.7 mmol), and copper(I) oxide (0.26 g, 1.82 mmol) in pyridine (30 ml) is heated under nitrogen atmosphere at reflux overnight. After pyridine is distilled, the residue is diluted with chloroform, filtered, and washed with chloroform. The combined filtrate is washed with water, dried over magnesium sulfate, and concentrated in vacuo. The crude material is purified by column chromatography on silica with hexane/ethyl acetate (1:2) to give 4-(1,2,4-triazol-1-yl)-benzaldehyde and with ethyl acetate/methanol (19:1) to give 4-(1,3,4-triazol-1-yl)-benzaldehyde.

To a solution of trimethyl 2-(3,5-dimethylbenzoyl)amino-phosphonoacetate (0.51 g, 1.54 mmol) in methylene chloride (3.0 ml) under nitrogen atmosphere is added 1,8-diazabyclo[5.4.0]undec-7-ene (0.24 ml, 1.60 mmol). After 10 min, 4-(1,2,4-triazol-1-yl)benzaldehyde (0.27 g, 1.57 mmol) is added and stirring is continued for 3 h. The reaction mixture is diluted with diethyl ether. The prepicipates are filtered, washed with diethyl ether and water successively, and dried in vacuo to give methyl 2-(3,5-dimethylbenzoyl)amino-3-[4-(1,2,4-triazol-1-yl)phenyl] acrylate. To a cooled (0° C.) solution of methyl 2-(3,5-dimethylbenzoyl)amino-3-[4-(1,2,4-triazol-1-yl)phenyl]-acrylate (0.35 g, 0.94 mmol) and iodomethane (0.20 ml, 3.21 mmol) in N,N'-dimethylformamide (3.0 ml) under nitrogen atmosphere is added sodium hydride (0.045 g, 60% in oil, 1.12 mmol). After 1 h, the mixture is warmed to room temperature and stirred for 1 h. The mixture is diluted with diethyl ether and washed with water and with brine. The organic layer is dried over magnesium sulfate and concentrated in vacuo to give methyl 2-[N-(3,5-dimethylbenzoyl)-N-methyl]amino-3-[4-(1,2,4-triazol-1-yl)-phenyl]acrylate.

A solution of 2-[N-(3,5-dimethylbenzoyl)-N-methyl] amino-3-[4-(1,2,4-triazol-1-yl)-phenyl]acrylate (1.50 g, 4.5 mmol) in methanol (50 ml) is hydrogenated over platinum oxide (1 mg) under 3 atm hydrogen atmosphere overnight. Catalyst is removed by filtration and the filtrate is concentrated in vacuo. The crude material is purified by column chromatography on silica with hexane/ethyl acetate (1:5) to give N-(3,5-dimethylbenzoyl)-N-methyl-3-[4-(1,2,4-triazol-1-yl)-phenyl]-(D,L)-alanine methyl ester.

N-(3,5-dimethylbenzoyl)-N-methyl-3-[4-(1,2,4-triazol-1-yl)-phenyl]-(D,L)-alanine methyl ester (1.24 g, 3.15 mmol) is treated with lithium hydroxide (0.16 g, 3.77 mmol) in methanol/tetrahydrofuran/water (1:1:1) (30 ml) at 0° C. After 2 h, the mixture is slowly warmed to room temperature and stirred overnight. The reaction mixture is acidified with 1N hydrochloric acid (3.8 ml), diluted with water, and extracted with chloroform. The organic layer is dried over sodium sulfate and concentrated in vacuo to give N-(3,5-dimethylbenzoyl)-N-methyl-3-[4-(1,2,4-triazol-1-yl)-phenyl]-(D,L)-alanine.

Example 13

N-Butanesulfonyl-[N-(3,5-dimethylbenzoyl)-N-methyl-3-[4-(1,2,3-triazol-1-yl)-phenyl]-(D,L)-alanyl]-(L)-tryptophanamide To a stirred solution of N-(3,5-dimethylbenzoyl)-N-methyl-3-[4-(1,2,3-triazol-1-yl)-phenyl]-(D,L)-alanine (115 mg, 0.30 mmol) in N,N'-dimethylformamide under nitrogen atmosphere are added N-butanesulfonyl-tryptophanamide hydrochloride (109 mg, 0.30 mmol) and 1-hydroxybenzotriazole (75 mg, 0.56 mmol). The mixture is cooled to 0° C. and 1-(3-dimethylaminopropyl)-3-ethyl-carbodiimide (0.067 ml, 0.37 mmol) is added dropwise. After 2 h, the reaction mixture is slowly warmed to room temperature and stirred overnight. The mixture is diluted with ethyl acetate and washed with water and with brine. The organic layer is dried over magnesium sulfate and concentrated in vacuo. The crude material is purified by preparative thin layer chromatography with methylene chloride/methanol (17:3) to give N-butanesulfonyl-[N-(3,5-dimethylbenzoyl)-N-methyl-3-[4-(1,2,3-triazol-1-yl)-phenyl]-(D,L)-alanyl]-(L)-tryptophanamide

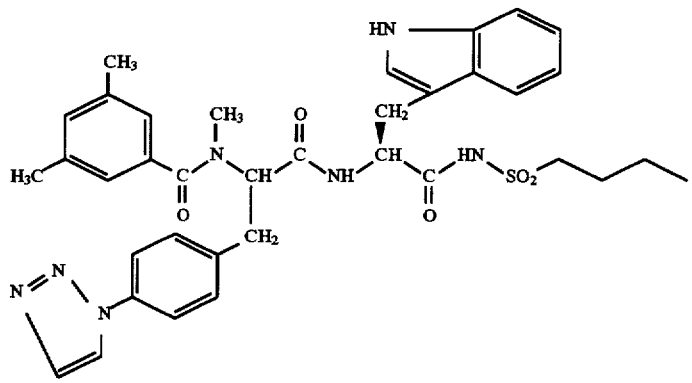

The starting material can be obtained, for example, as follows:

A mixture of 1,2,3-triazole (3.4 ml, 58.7 mmol), potassium carbonate (9.03 g, 65.4 mmol), and 4-fluorobenzaldehyde (6.3 ml, 58.7 mmol) in pyridine (30 ml) is heated under nitrogen atmosphere at reflux overnight. After pyridine is distilled, the mixture is diluted with methylene chloride, filtered and washed with chloroform. The combined filtrate is washed with water, dried over magnesium sulfate, and concentrated in vacuo. The crude material is purified by column chromatography on silica with hexane/ethyl acetate (5:1) to give 4-(1,2,3-triazol-1-yl)-benzaldehyde and with hexane/ethyl acetate (1:2) to give 4-(1,2,3-triazol-1-yl)-benzaldehyde.

To a solution of trimethyl 2-(3,5-dimethylbenzoyl)-amino-phosphonoacetate (prepared according to the procedure described in Example 12 (0.53 g, 1.62 mmol) in methylene chloride (3.0 ml) under nitrogen atmosphere is added 1,8-diazabicyclo[5.4.0]undec-7-ene (0.25 ml, 1.67 mmol). After 10 min, 4-(1,2,3-triazol-1-yl)-benzaldehyde (0.287 g, 1.66 mmol) is added and stirring is continued overnight. The reaction mixture is diluted with methylene chloride, washed with water, dried over magnesium sulfate, and concentrated in vacuo to give methyl 2-(3,5-dimethylbenzoyl)-amino-3-[4-(1,2,3-triazol-1-yl)phenyl]acrylate.

To a cooled (0° C.) solution of methyl 2-(3,5-dimethylbenzoyl)amino-3-[4-(1,2,3-triazol-1-yl)phenyl]acrylate (0.351 g, 0.89 mmol) and iodomethane (0.18 ml, 2.89 mmol) in N,N'-dimethylformamide (3.0 ml) under nitrogen atmosphere is added sodium hydride (0.04 g 60% in oil, 1.0 mmol). The stirring is continued for 1.5 h. The reaction mixture is diluted with diethyl ether, washed with water and with brine. The organic layer is dried over magnesium sulfate, concentrated in vacuo. The residue is purified by column chromatography on silica with hexane/ethyl acetate (1:1) to give methyl 2-[N-(3,5-dimethylbenzoyl)-N-methyl]-amino-3-[4-(1,2,3-triazol-1-yl)phenyl]acrylate.

A solution of methyl 2-[N-(3,5-dimethylbenzoyl)-N-methyl]amino-3-[4-(1,2,3-triazol-1-yl)phenyl]acrylate (0.275 g, 0.704 mmol) and trifluoroacetic acid (1.0 ml) in methanol (30 ml) is hydrogenated over palladium on carbon (10%, 80 mg) under 3 atm hydrogen atmosphere. After 4 days, catalyst is removed by filtration and the filtrate is concentrated in vacuo. The residue is diluted with saturated sodium bicarbonate and extracted with ethyl acetate. The organic layer is washed with water and with brine, dried over magnesium sulfate, and concentrated in vacuo to give N-(3,5-dimethylbenzoyl)-N-methyl-3-[4-(1,2,3-triazol-1-yl)-phenyl]-(D,L)-alanine methyl ester.

N-(3,5-Dimethylbenzoyl)-N-methyl-3-[4-(1,2,3-triazol-1-yl)-phenyl]-(D,L)-alanine methyl ester (0.248 g, 0.632 mmol) is treated with lithium hydroxide (0.037 g, 0.88 mmol) in methanol/tetrahydrofuran/water (2:1:2) (5 ml) at room temperature. After 1.5 h, the reaction mixture is acidified with 1N hydrochloric acid (0.9 ml), diluted with water, and extracted with ethyl acetate. The organic layer is washed with brine, dried over magnesium sulfate, and concentrated in vacuo to give N-(3,5-dimethylbenzoyl)-N-methyl-3-[4-(1,2,3-triazol-1-yl)-phenyl]-(D,L)-alanine.

Example 14

In a manner analogous to that described hereinbefore it is also possible to manufacture the following compounds:

(1) N-methyl-N-benzenesulfonyl-[N-(3,5-dimethylbenzoyl)-N-methyl-3-[4-(5-isoxazolyl)-phenyl]-(D,L)-alanyl]-(D,L)-tryptophanamide;

(2) N-isopropanesulfonyl-[N-(3,5-dimethylbenzoyl)-N-methyl-3-[4-(5-isoxazolyl)-phenyl]-(D,L)-alanyl-(D,L)-tryptophanamide;

(3) N-(4-hydroxy-benzene)-sulfonyl-[N-(3,5-dimethylbenzoyl)-N-methyl-3-[4-(5-isoxazolyl)-phenyl]-(D,L)-alanyl-(D,L)-tryptophanamide; (4) N-(2-ethoxyethane)-sulfonyl-[N-(3,5-dimethylbenzoyl)-N-methyl-3-[4-(5-isoxazolyl)-phenyl]-(D,L)-alanyl]-(L) tryptophanamide;

(5) N-(2-nitro-benzene)-sulfonyl-[N-(3,5-dimethylbenzoyl)-N-methyl-3-[4-(5-isoxazolyl)-phenyl]-(D,L)-alanyl]-(D,L)-tryptophanamide;

(6) N-(3-nitro-benzene)-sulfonyl-[N-(3,5-dimethylbenzoyl)-N-methyl-3-[4-(5-isoxazolyl)-phenyl]-(D,L)-alanyl]-(D,L)-tryptophanamide;

(7) N-benzylsulfonyl-[N-(3,5-dimethylbenzoyl)-N-methyl-3-[4-(5-isoxazolyl)-phenyl]-(L)-alanyl]-(L)-tryptophanamide;

(8) N-n-butanesulfonyl-[N-(3,5-dimethylbenzoyl)-N-methyl-3-[4-(5-isoxazolyl)-phenyl]-(L)-alanyl]-(L)-tryptophanamide;

(9) N-n-butanesulfonyl-[N-(3,5-dimethoxybenzoyl)-N-methyl-3-[4-(5-isoxazolyl)-phenyl]-(D,L)-alanyl]-(L)-tryptophanamide;

(10) N-n-butanesulfonyl-[N-(3,5-dimethylbenzoyl)-N-methyl-3-[4-(5-isothiazolyl)-phenyl]-(D,L)-alanyl]-(L)-tryptophanamide;

(11) N-n-butanesulfonyl-[N-(3-methyl-5-methoxy-benzoyl)-N-methyl-3-[4-(5-isoxazol-yl)-phenyl]-(D,L)-alanyl]-(L)-tryptophanamide;

(12) N-n-butanesulfonyl-[N-(3,5-dimethyl-benzoyl)-N-methyl-3-[4-(5-isoxazolyl)-phenyl]-(D,L)-alanyl]-(L)-3-(2-naphthyl)-alanylamide;

(13) N-n-butanesulfonyl-[N-(3,5-dimethyl-benzoyl)-N-methyl-3-[4-(5-isoxazolyl)-phenyl]-(D,L)-alanyl]-(L)-3-(3-naphthyl)-alanylamide;

(14) N-(2-propene)-sulfonyl-[N-(3,5-dimethyl-benzoyl)-N-methyl-3-[4-(5-isoxazolyl)-phenyl]-(D,L)-alanyl]-(L)-tryptophanamide;

(15) N-vinylsulfonyl-[N-(3,5-dimethyl-benzoyl)-N-methyl-3-[4-(5-isoxazolyl)-phenyl]-(D,L)-alanyl]-(L)-tryptophanamide;

(16) N-(3-phenyl-2-propene)-sulfonyl-[N-(3,5-dimethyl-benzoyl)-N-methyl-3-[4-(5-isoxazolyl)-phenyl]-(D,L)-alanyl]-(L)-tryptophanamide;

(17) N-(3-butene)-sulfonyl-[N-(3,5-dimethyl-benzoyl)-N-methyl-3-[4-(5-isoxazolyl)-phenyl]-(D,L)-alanyl]-(L)-tryptophanamide;

(18) N-(3-nitro-benzene)-sulfonyl-[N-(3,5-dimethylbenzoyl)-N-methyl-3-[4-(5-isoxazol-yl)-phenyl]-(L)-alanyl]-(L)-tryptophanamide;

(19) N-butanesulfonyl-[N-(3,5-dimethylbenzoyl)-N-methyl-3-[4-(5-isoxazolyl)-phenyl]-(D,L)-alanyl]-(L)-leucineamide;

(20) N-butanesulfonyl-[N-(3,5-dimethylbenzoyl)-N-methyl-3-[4-(5-isoxazolyl)-phenyl]-(D,L)-alanyl]-(L)-phenylglycinamide;

(21) N-methallylsulfonyl-[N-(3,5-dimethylbenzoyl)-N-methyl-3-[4-(5-isoxazolyl)-phenyl]-(D,L)-alanyl]-(L)-isoleucineamide;

(22) N-n-butanesulfonyl-[N-(3,5-dimethyl-benzoyl)-N-methyl-3-[4-(5-isoxazolyl)-phenyl]-(D,L)-alanyl]-(D,L)-3-(3,4-methylenedioxy-phenyl)-alanylamide;

(23) N-n-butanesulfonyl-[N-(3,5-dimethyl-benzoyl)-N-methyl-3-λ4-(5-isoxazolyl)-phenyl]-(D,L)-alanyl]-(D,L)-3-(3-thienyl)-alanylamide;

(24) N-n-butanesulfonyl-[N-(3,5-dimethyl-benzoyl)-N-methyl-3-[4-(5-isoxazolyl)-phenyl]-(D,L)-alanyl]-(L)-cyclohexylglycineamide;

(25) N-n-butanesulfonyl-[N-(3,5-dimethyl-benzoyl)-N-methyl-3-[4-(5-isoxazolyl)-phenyl]-(D,L)-alanyl]-(D,L)-(2-amino-5-phenyl)-pent-4-enoic acid amide;

(26) N-n-butanesulfonyl-[N-(3,5-dimethylbenzoyl)-N-methyl-3-[4-(1,2,3-triazol-1-yl)-phenyl]-(D,L)-alanyl]-(L)-tryptophanamide;

(27) N-n-butanesulfonyl-[N-(3,5-dimethylbenzoyl)-N-methyl-3-[4-(1,2,3-triazol-2-yl)-phenyl]-(D,L)-alanyl]-(L)-tryptophanamide;

(28) N-benzenesulfonyl-[N-(3,5-dimethylbenzoyl)-N-methyl-3-[4-(5-isoxazolyl)-phenyl]-(D,L)-alanyl]-(L)-isoleucineamide;

(29) N-n-butanesulfonyl-[N-(3,5-dimethylbenzoyl)-N-methyl-3-[4-(5-isoxazolyl)-phenyl]-(D,L)-alanyl]-(L)-alanylamide;

(30) N-n-butanesulfonyl-[N-(3,5-dimethyl-benzoyl)-N-methyl-3-[4-(5-isoxazolyl)-phenyl]-(D,L)-alanyl-(L)-(2-amino)-pent-4-enoic acid amide;

(31) N-benzoyl-[N-(3,5-dimethyl-benzoyl)-N-methyl-3-[4-(3-thienyl)-phenyl]-(D,L)-alanyl]-(L)-tryptophanamide;

(32) N-butanesulfonyl-[N-(3,4-methylenedioxybenzoyl)-N-methyl-3-[4-(5-isoxazolyl)-phenyl]-(D,L)-alanyl]-(L)-tryptophanamide;

(33) N-n-butanesulfonyl-[N-(3,5-dimethyl-benzoyl)-N-methyl-3-[4-(1-pyrazolyl)-phenyl]-(D,L)-alanyl]-(L)-tryptophanamide.

Example 15

| Composition (for 10,000 tablets) | |
|---|---|
| Active ingredient | 500.0 g |
| Lactose | 500.0 g |
| Potato starch | 352.0 g |
| Gelatin | 8.0 g |
| Talc | 60.0 g |
| Magnesium stearate | 10.0 g |
| Silica (highly disperse) | 20.0 g |
| Ethanol | q.s. |

The active ingredient is mixed with the lactose and 292 g of potato starch, and the mixture is moistened using an alcoholic solution of the gelatin and granulated by means of a sieve. After drying, the remainder of the potato starch, the talc, the magnesium stearate and the highly disperse silica are admixed and the mixture is compressed to give tablets of weight 145.0 mg each and active ingredient content 50.0 mg which, if desired, can be provided with breaking notches for finer adjustment of the dose.

Example 16

Coated tablets, each containing 100 mg of active ingredient, for example, [N-(3,5-di-methylbenzoyl)-N-methyl-3-[4-(5-isoxazolyl)-phenyl]-(D)-alanyl]-(D,L)-tryptophane, can be prepared as follows:

| Composition (for 1000 tablets): | |
|---|---|
| Active ingredient | 100.00 g |
| Lactose | 100.00 g |
| Corn starch | 70.00 g |
| Talc | 8.50 g |
| Calcium stearate | 1.50 g |
| Hydroxypropylmethylcellulose | 2.36 g |
| Shellac | 0.64 g |
| Water | q.s. |
| Dichloromethane | q.s. |

The active ingredient, the lactose and 40 g of the corn starch are mixed and moistened and granulated with a paste prepared from 15 g of corn starch and water (with warming). The granules are dried, and the remainder of the corn starch, the talc and the calcium stearate are added and mixed with the granules. The mixture is compressed to give tablets (weight: 280 mg) and these are coated with a solution of the hydroxypropylmethylcellulose and the shellac in dichloromethane (final weight of the coated tablet: 283 mg).

Example 17

Tablets and coated tablets containing another compound of the formula I or a pharmaceutically acceptable salt of a compound of the formula I, for example as in one of Examples 1 to 14, can also be prepared in an analogous manner to that described in Examples 15 and 16.

Pharmacological Experiments

Endothelin (ET) receptor binding assay

The binding affinity to the ET receptor of the compounds of the present invention is determined according to the method described below (published in Takai et. al (1992) *Biochem. Biophys. Res. Commun.* 184, 953–959). ET-1 and ET-3 were purchased from Peptide Institute Inc. (Osaka, Japan), [$^{125}$I]ET-1 and [$^{125}$I]ET-3 (~74 TBq/mmol each) were purchased from Amersham International (Bucks, U.K.).

The plasma membrane of porcine lung (2 mg of protein) is incubated at 37° C. for 1 hour with 30 pM [$^{125}$I]ET-1 or 10 pM [$^{125}$I]ET-3 in the absence or presence of various amounts of nonlabeled ligands in a total volume of 1 ml of 20 mM HEPES (pH 7.4), containing 145 mM NaCl, 5 mM KCl, 3 mM MgCl$_2$, 1 mM EGTA 1 mg/ml bovine serum albumin, and 0.2 mg/ml bacitracin. After the incubation, unbound [$^{125}$I]ETs were separated by centrifugation at 20,000×g for 20 min at 4° C. followed by aspiration of the supernatant. The radioactivity in the membrane pellet is measured in Wallac-1470 Wizard autogamma counter (Pharmacia). Nonspecific binding is defined as membrane-associated radioactivity in the presence of saturating concentrations of ETs (100 nM). Nonspecific binding is subtracted from the total binding and the difference is defined as specific binding. Total binding is always less than 15% of the total radioactivity added. The binding to the ET$_A$ receptor is determined with [$^{125}$I]ET-1 in the presence of 1 nM nonlabeled ET-3 and the binding to the ET$_B$ receptor with [$^{125}$I]ET-3 alone. By Scatchard analysis, the ET$_A$ receptor showed an apparant dissociation constant (Kd) of 44 pM and maximum binding sites (Bmax) of 342 fmol/mg protein, while the ET$_B$ receptor has a Kd of 8 pM and Bmax of 362 fmol/mg protein. From the inhibition curves for the binding of [$^{125}$I]ETs, the apparant binding affinity constant (Ki) of one of the test compounds is calculated as a parameter of the affinity for the ET$_A$ and ET$_B$ receptors, as shown in the following table.

| Example | Ki for the ET$_A$-Receptor | Ki for the ET$_B$-Receptor |
| --- | --- | --- |
| 1 | 21.0 | 0.9 |
| 2 | 5.3 | 0.3 |
| 6 | 2.3 | 0.34 |
| 7(9) | 51.0 | 2.3 |
| 8 | 2.9 | 0.24 |
| 9 | 0.89 | 0.23 |
| 10(a) | 6.9 | 3.5 |
| 11 | 1.8 | 1.2 |
| 12 | 3.2 | 0.16 |
| 13 | 3.5 | 0.27 |

We claim:

1. A compound of formula (I)

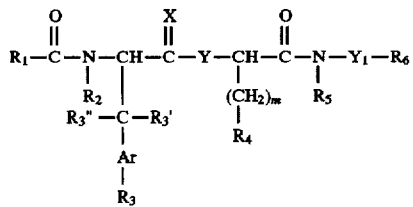

Ar represents a direct bond or arylene;

m is 0, 1, 2, or 3;

R$_1$ is lower alkyl, cycloalkyl-lower alkyl, aryl-lower alkyl, cycloalkyl, aryl, aryl-cycloalkyl, lower alkoxy, or aryloxy;

R$_2$ is hydrogen, lower alkyl, aryl-lower alkyl, cycloalkyl, or cycloalkyl-lower alkyl;

R$_3$ represents hydrogen, hydroxy, amino, nitro, lower alkyl, cycloalkyl, or aryl-lower alkyl, provided that Ar is a direct bond, or represents aryl;

R$_3$' represents hydrogen, lower alkyl, cycloalkyl, aryl-lower alkyl, or aryl; or R$_3$ and R$_3$' together form a ring structure, provided that Ar is a direct bond;

R$_3$" is hydrogen, lower alkyl or aryl; or

R$_2$ and R$_3$" together form the lower alkylene group —(CH$_2$)$_n$— wherein n is an integer of 1, 2 or 3; or R$_2$ and R$_3$" together form a group represented by the formula: —(CH$_2$)$_o$—Ar$_1$— or —Ar$_1$—(CH$_2$)$_o$—, respectively, wherein o is zero or an integer of 1 or 2, and Ar$_1$ is arylene;

C(=X) is C(=O), C(=S), C(=NH), C(=N-lower alkyl); C=NH—OH, or CH$_2$; and Y is a direct bond, —NH—,

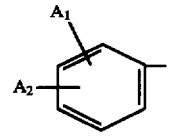

oxygen, or methylene; or

C(=X) is CHOH and Y is a direct bond or methylene;

R$_4$ is lower alkyl, lower alkenyl, cycloalkyl, aryl-lower alkyl, aryl-lower alkenyl, or aryl;

R$_5$ is hydrogen, lower alkyl, aryl-lower alkyl, cycloalkyl, or cycloalkyl-lower alkyl;

R$_6$ represents lower alkyl, halo-lower alkyl, hydroxy-lower alkyl, acyloxy-lower alkyl, lower alkoxy-lower alkyl, aryloxy-lower alkyl, aryl-lower alkyl, lower alkenyl, lower alkenyl which substituted by at least one substituent selected from the group consisting of carboxy, lower alkoxycarbonyl, hydroxy, lower alkoxy, amino, lower alkylamino and di-lower alkylamino, or represents aryl-lower alkenyl, aryl or lower alkyl which is substituted by carboxy or lower alkoxycarbonyl and also by amino, lower alkylamino or di-lower alkylamino; or R$_5$ and R$_6$ together form the lower alkylene group —(CH$_2$)$_p$— wherein p is an integer of 3–5, or together form a group represented by the formulae: —(CH$_2$)$_q$—Ar$_1$— or —Ar$_1$—(CH$_2$)$_q$—, wherein q is zero or an integer of 1 or 2, and Ar$_1$ is arylene; and Y$_1$ represents —SO$_2$—, —O—, —NH—, —NH—CO—, —NH—CO—O— or —NH—SO$_2$—; and wherein "aryl", it being a mono- or bivalent aryl radical or aryl moiety, respectively, represents, in each case, a corresponding carbocyclic or heterocyclic aryl radical or aryl moiety, respectively; or a salt thereof.

2. A compound as claimed in claim 1 of formula (I) wherein

Ar represents a direct bond or phenylene;

R$_1$ is mono- or di-substituted phenyl

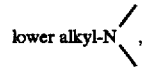

in which one of A$_1$ and A$_2$ is or in which A$_1$ and A$_2$, independently of one another, are halogen, lower alkyl, lower alkoxy, trifluoromethyl, hydroxy, phenyl-lower alkoxy, or nitro; or A$_1$ and A$_2$ together form —O—CH$_2$—O—;

R$_2$ is hydrogen or lower alkyl;

R$_3$ represents hydrogen, hydroxy, amino, nitro, phenyl, thienyl, furanyl, pyrrolyl, pyrazolyl, oxazolyl, isoxazolyl, thiazolyl, isothiazolyl, oxadiazolyl, thiadiazolyl, imidazolyl, triazolyl, or pyridyl, each of which is unsubstituted or substituted by halogen, lower alkyl, lower alkoxy, trifluoromethyl, cyano, amino, hydroxy or nitro;

R$_3$' and R$_3$", independently of one another, represent hydrogen or phenyl which is unsubstituted or substituted by halogen, lower alkyl, lower alkoxy, trifluoromethyl, cyano, amino, hydroxy, or nitro; or R$_3$ and R$_3$' together form fluorenyl, anthryl, or dibenzosuberyl, provided that Ar is a direct bond; or R$_2$ and R$_3$" together form the lower alkylene group —(CH$_2$)$_n$— wherein n is an integer of 1, 2 or 3;

C(=X) is C(=O), C(=NH), C(=N-lower alkyl); and Y is a direct bond, —NH—,

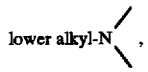

oxygen, or methylene;

R$_4$ represents naphthyl, thienyl, 3,4-methylenedioxyphenyl, indolyl or 1-lower alkyl-indolyl each of which is unsubstituted or substituted by halogen, lower alkyl, lower alkoxy, trifluoromethyl, or hydroxy, and m is 1, 2, or 3; or R$_4$ is lower alkyl, lower alkenyl, C$_3$–C$_8$-cycloalkyl, phenyl-lower alkyl, phenyl-lower alkenyl, or phenyl, and m is 0;

R$_5$ is hydrogen or lower alkyl; and

R$_6$ represents lower alkyl, halo-lower alkyl, hydroxy-lower alkyl, lower alkoxy-lower alkyl, phenyl-lower alkyl in which phenyl is unsubstituted or substituted by halogen, lower alkyl, lower alkoxy, trifluoromethyl, or hydroxy; lower alkenyl, lower alkenyl which substituted by at least one substituent selected from the group consisting of carboxy, lower alkoxycarbonyl, hydroxy, lower alkoxy, amino, lower alkylamino and di-lower alkylamino, or represents phenyl-lower alkenyl, phenyl, thienyl, furyl, thiadiazolyl, pyrimidyl or pyridyl, each of which is unsubstituted or substituted by halogen, lower alkyl, lower alkoxy, trifluoromethyl, hydroxy, nitro, carboxy, or lower alkoxycarbonyl; or R$_5$ and R$_6$ together form the lower alkylene group of —(CH$_2$)$_p$— wherein p is an integer of 3–5; and Y$_1$ is —SO$_2$—, —O—, —NH—, —NH—CO—, —NH—CO—O—, or —NH—SO$_2$—;

or a salt thereof, especially a pharmaceutically acceptable salt thereof.

3. A compound as claimed in claim 1 of formula (I) wherein

Ar represents a direct bond or phenylene;

R$_1$ is mono- or di-substituted phenyl

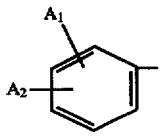

in which one of A$_1$ and A$_2$ is or in which A$_1$ and A$_2$, independently of one another, are halogen, lower alkyl, lower alkoxy, trifluoromethyl, hydroxy, phenyl-lower alkoxy, or nitro;

R$_2$ is hydrogen or lower alkyl;

R$_3$ represents phenyl, thienyl, furanyl, pyrrolyl, isoxazolyl, oxadiazolyl, thiadiazolyl, imidazolyl, or pyridyl, each of which is unsubstituted or substituted by halogen, lower alkyl, lower alkoxy, trifluoromethyl, cyano, amino, hydroxy or nitro;

R$_3$' and R$_3$", independently of one another, represent hydrogen or phenyl which is unsubstituted or substituted by halogen, lower alkyl, lower alkoxy, trifluoromethyl, cyano, amino, hydroxy, or nitro; or R$_3$ and R$_3$' together form fluorenyl, anthryl, or dibenzosuberyl, provided that Ar is a direct bond; or R$_2$ and R$_3$" together form the lower alkylene group —(CH$_2$)$_n$— wherein n is an integer of 1, 2 or 3;

C(=X) is C(=O), C(=NH), C(=N-lower alkyl); and Y is a direct bond, —NH—,

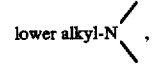

oxygen, or methylene;

R$_4$ represents indolyl or 1-lower alkyl-indolyl each of which is unsubstituted or substituted by halogen, lower alkyl, lower alkoxy, trifluoromethyl, or hydroxy, and m is 1, 2, or 3;

R$_5$ is hydrogen or lower alkyl; and

R$_6$ represents lower alkyl, halo-lower alkyl, hydroxy-lower alkyl, lower alkoxy-lower alkyl, phenyl-lower alkyl in which phenyl is unsubstituted or substituted by halogen, lower alkyl, lower alkoxy, trifluoromethyl, or hydroxy; phenyl, thienyl, furyl, thiadiazolyl, pyrimidyl or pyridyl, each of which is unsubstituted or substituted by halogen, lower alkyl, lower alkoxy, trifluoromethyl, hydroxy, carboxy, or lower alkoxycarbonyl; or R$_5$ and R$_6$ together form the lower alkylene group of —(CH$_2$)$_p$— wherein p is an integer of 3–5; and Y$_1$ is —SO$_2$—, —O—, —NH—, —NH—CO—, —NH—CO—O—, or —NH—SO$_2$—;

or a salt thereof, especially a pharmaceutically acceptable salt thereof.

4. A compound as claimed in claim 1 of formula (I) wherein

Ar represents a direct bond or phenylene;

R$_1$ is di-substituted phenyl

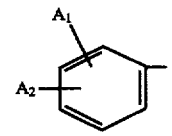

in which A$_1$ and A$_2$, independently of one another, are halogen, lower alkyl, lower alkoxy, trifluoromethyl, hydroxy, phenyl-lower alkoxy, or nitro; or A$_1$ and A$_2$ together form —O—CH$_2$—O—;

R$_2$ is lower alkyl;

R$_3$ represents hydrogen, hydroxy, amino, nitro, phenyl, thienyl, pyridyl, pyrazolyl, isoxazolyl, oxadiazolyl, isothiazolyl, triazolyl, or thiadiazolyl, each of which is unsubstituted or substituted by halogen, lower alkyl, lower alkoxy, trifluoromethyl, cyano, amino, hydroxy, or nitro;

R$_3$' and R$_3$", independently of one another, represent hydrogen or phenyl which is unsubstituted or substituted by halogen, lower alkyl, lower alkoxy, trifluoromethyl, cyano, amino, hydroxy, or nitro;

C(=X) is C(=O), C(=NH), C(=N-lower alkyl); and Y is a direct bond, —NH—,

oxygen, or methylene;

R₄ represents naphthyl, thienyl, 3,4-methylenedioxyphenyl, indolyl or 1-lower alkyl-indolyl each of which is unsubstituted or substituted by halogen, lower alkyl, trifluoromethyl, lower alkoxy, or hydroxy, and m is 1 or 2; or R₄ is lower alkyl, lower alkenyl, phenyl-lower alkyl, $C_5$–$C_6$-cycloalkyl, or phenyl and m is zero;

R₅ is hydrogen; and

R₆ represents lower alkyl, lower alkenyl, halo-lower alkyl, lower alkoxy-lower alkyl, phenyl-lower alkyl or phenyl-lower alkenyl in which phenyl is unsubstituted or substituted by halogen, lower alkyl, trifluoromethyl, lower alkoxy, or hydroxy; lower alkenyl, phenyl or thienyl, each of which is unsubstituted or substituted by halogen, lower alkyl, lower alkoxy, trifluoromethyl, hydroxy, nitro, carboxy, or lower alkoxycarbonyl; and $Y_1$ is —SO₂, —O—, —NH—, —NH—CO—, or —NH—CO—O—;

or a salt thereof, especially a pharmaceutically acceptable salt thereof.

5. A compound as claimed in claim 1 of formula (Ia)

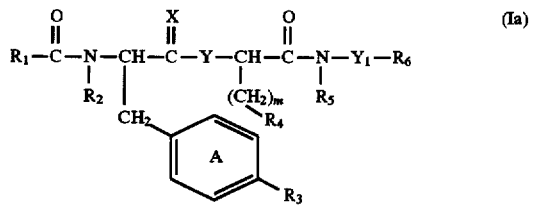

wherein
ring A is unsubstituted or substituted by halogen, lower alkyl, lower alkoxy, trifluoromethyl, or hydroxy;
$R_1$ is di-substituted phenyl

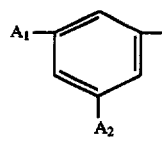

in which $A_1$ and $A_2$, independently of one another, are lower alkyl, trifluoromethyl, lower alkoxy, hydroxy, phenyl-lower alkoxy, or halogen;

$R_2$ is lower alkyl;

$R_3$ represents (i) hydrogen, hydroxy, amino or nitro or (ii) phenyl, thienyl, pyridyl, pyrazolyl, triazolyl, isoxazolyl, or isothiazolyl each of which is unsubstituted or substituted by halogen, lower alkyl, lower alkoxy, trifluoromethyl, cyano, amino, hydroxy, or nitro;

C(=X) is C(=O) or C(=NH), and Y is —NH— or methylene;

R₄ represents naphthyl, thienyl, 3,4-methylenedioxyphenyl, or indolyl each of which is unsubstituted or substituted by halogen, lower alkyl, lower alkoxy, trifluoromethyl, or hydroxy, and m is 1 or 2; or R₄ is lower alkyl, lower alkenyl, phenyl-lower alkenyl, $C_5$–$C_6$-cycloalkyl, or phenyl, and m is zero;

$R_5$ is hydrogen or lower alkyl;

$R_6$ represents lower alkyl, halo-lower alkyl, lower alkoxy-lower alkyl, lower alkenyl, or phenyl-lower alkenyl, or represents phenyl, or thienyl each of which is unsubstituted or substituted by halogen, lower alkyl, lower alkoxy, trifluoromethyl, hydroxy, nitro, carboxy or lower alkoxycarbonyl; and $Y_1$ is —SO₂—, —O—, —NH—, or —NH—CO—;

or a salt thereof, especially a pharmaceutically acceptable salt thereof.

6. A compound as claimed in claim 5 of formula (Ia), wherein ring A is unsubstituted or substituted by halogen, lower alkyl, lower alkoxy, trifluoromethyl, or hydroxy;

$R_1$ is di-substituted phenyl

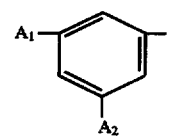

in which $A_1$ and $A_2$, independently of one another, are lower alkyl, trifluoromethyl, lower alkoxy, hydroxy, phenyl-lower alkoxy, or halogen;

$R_2$ is lower alkyl;

$R_3$ represents phenyl, thienyl, or isoxazolyl, each of which is unsubstituted or substituted by halogen, lower alkyl, lower alkoxy, trifluoromethyl, cyano, amino, hydroxy, or nitro;

C(=X) is C(=O) or C(=NH), and Y is —NH— or methylene;

$R_4$ represents indolyl which is unsubstituted or substituted by halogen, lower alkyl, lower alkoxy, trifluoromethyl, or hydroxy, and m is 1 or 2; or $R_5$ is hydrogen or lower alkyl;

$R_6$ represents lower alkyl, halo-lower alkyl or lower alkoxy-lower alkyl, or represents phenyl or thienyl each of which is unsubstituted or substituted by halogen, lower alkyl, lower alkoxy, trifluoromethyl, hydroxy, carboxy or lower alkoxycarbonyl; and $Y_1$ is —SO₂—, —O— or —NH—;

or a salt thereof, especially a pharmaceutically acceptable salt thereof.

7. A compound as claimed in claim 5 of formula (Ia), wherein ring A is unsubstituted;

$R_1$ is 3,5-di-lower alkyl-phenyl, preferably 3,5-dimethylphenyl;

$R_2$ is $C_1$–$C_4$-alkyl;

$R_3$ represents phenyl, isoxazolyl, preferably 5-isoxazolyl, or thienyl, preferably 3-thienyl, furthermore hydrogen or hydroxy;

C(=X) is C(=O); and Y is —NH—;

$R_4$ represents indolyl, preferably 3-indolyl, and m is 1; or $R_4$ represents $C_1$–$C_4$-alkyl, preferably methyl, 2-propyl, 2-methyl-1-propyl, or 2-butyl, or $C_2$–$C_4$-alkenyl, preferably, allyl or methallyl, and m is 0;

$R_5$ is hydrogen;

$R_6$ represents $C_1$–$C_4$-alkyl, halo-$C_1$–$C_4$-alkyl, $C_1$–$C_4$-alkoxy-$C_1$–$C_4$-alkyl, phenyl-$C_1$–$C_4$-alkyl, or phenyl or thienyl, preferably 2-thienyl each of which is unsubstituted or substituted by halogen, trifluoromethyl, $C_1$-$C_4$-alkyl, $C_1$-$C_4$-alkoxy, hydroxy, carboxy or $C_2$-$C_5$-alkoxycarbonyl, or represents $C_3$-$C_5$-alkenyl, preferably allyl;

$Y_1$ is —$SO_2$—;

or a salt thereof, especially a pharmaceutically acceptable salt thereof.

8. A compound as claimed in claim 5 of formula (Ia), wherein ring A is unsubstituted or substituted by halogen, $C_1$-$C_4$-alkyl, $C_1$-$C_4$-alkoxy, trifluoromethyl, or hydroxy; m is 1;

$R_1$ is 3,5-di-lower alkyl-phenyl, preferably 3,5-dimethyl-phenyl;

$R_2$ is $C_1$-$C_4$-alkyl;

$R_3$ represents phenyl, isoxazolyl, preferably 5-isoxazolyl, or thienyl, preferably 3-thienyl;

C(=X) is C(=O); and Y is —NH— or methylene;

$R_4$ represents indolyl, preferably 3-indolyl;

$R_5$ is hydrogen;

$R_6$ represents $C_1$-$C_4$-alkyl, $C_1$-$C_4$-alkoxy-$C_1$-$C_4$-alkyl, or phenyl or thienyl, preferably 2-thienyl each of which is unsubstituted or substituted by halogen, trifluoromethyl, $C_1$-$C_4$-alkyl, $C_1$-$C_4$-alkoxy, hydroxy, carboxy or $C_2$-$C_5$-alkoxycarbonyl; and $Y_1$ is —$SO_2$—;

or a salt thereof, especially a pharmaceutically acceptable salt thereof.

9. A compound as claimed in claim 5 of formula (Ia), wherein ring A is unsubstituted;

$R_1$ is 3,5-dimethyl-phenyl;

$R_2$ is $C_1$-$C_4$-alkyl such as methyl or ethyl;

$R_3$ represents 5-isoxazolyl, 3-thienyl or phenyl;

C(=X) is C(=O); and Y is —NH—;

$R_4$ represents 3-indolyl and m is 1; or $R_4$ represents $C_1$-$C_4$-alkyl, especially 2-propyl or 2-butyl, or $C_2$-$C_4$-alkenyl, preferably, allyl or methallyl, and m is 0;

$R_5$ is hydrogen;

$R_6$ represents $C_1$-$C_4$-alkyl, phenyl or 2-thienyl each of which is unsubstituted or substituted by $C_1$-$C_4$-alkyl, or represents $C_3$-$C_5$alkenyl, especially allyl; and $Y_1$ is —$SO_2$;

or a salt thereof, especially a pharmaceutically acceptable salt thereof.

10. A compound as claimed in claim 5 of formula (Ia), wherein ring A is unsubstituted or substituted by halogen, $C_1$-$C_4$-alkyl, $C_1$-$C_4$-alkoxy, trifluoromethyl, or hydroxy; m is 1;

$R_1$ is 3,5-dimethyl-phenyl;

$R_2$ is $C_1$-$C_4$-alkyl such as methyl or ethyl;

$R_3$ represents 5-isoxazolyl, 3-thienyl or phenyl;

C(=X) is C(=O); and Y is —NH—;

$R_4$ represents 3-indolyl;

$R_5$ is hydrogen;

$R_6$ represents $C_1$-$C_4$-alkyl, $C_1$-$C_4$-alkoxy-$C_1$-$C_4$-alkyl, or phenyl or 2-thienyl each of which is unsubstituted or substituted by $C_1$-$C_4$-alkyl; and $Y_1$ is —$SO_2$—;

or a salt thereof, especially a pharmaceutically acceptable salt thereof.

11. A compound as claimed in claim 5 of formula (Ia), wherein ring A is unsubstituted;

$R_1$ is 3,5-dimethyl-phenyl;

$R_2$ is methyl;

$R_3$ represents 5-isoxazolyl or 3-thienyl;

C(=X) is C(=O); and Y is —NH—;

$R_4$ represents 3-indolyl and m is 1;

$R_5$ is hydrogen;

$R_6$ represents n-propyl, n-butyl, allyl, phenyl or 2-thienyl; and $Y_1$ is —$SO_2$—;

or a salt thereof, especially a pharmaceutically acceptable salt thereof.

12. A compound according to claim 1 of formula (I') or (Ia'), respectively, having following formula

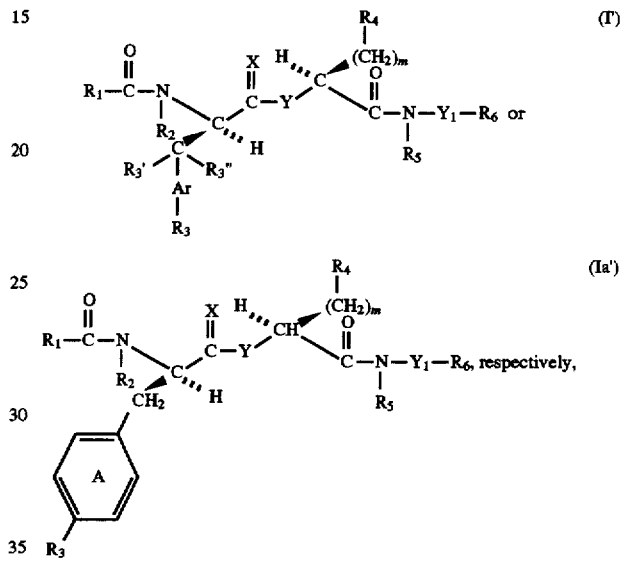

wherein the stereochemistry is R/S, if Y is different from —$CH_2$—; or is R/R, if Y is —$CH_2$—.

13. A compound according to claim 1, selected from the group consisting of:

N-benzenesulfonyl-[N-(3,5-dimethylbenzoyl)-N-methyl-3-(biphenyl-4-yl)-(D)-alanyl]-(L)-tryptophanamide;

N-(2-thienyl)sulfonyl-[N-(3,5-dimethylbenzoyl)-N-methyl-(D)-3-[4-(3-thienyl)phenyl]-alanyl]-(L)-tryptophanamide;

N-phenoxy-[N-(3,5-dimethylbenzoyl)-N-methyl-(D)-3-[4-(3-thienyl)phenyl]-alanyl]-(L)-tryptophanamide;

N-phenyl'-[N-(3,5-dimethylbenzoyl)-N-methyl-(D)-3-[4-(3-thienyl)phenyl]-alanyl]-(L)-tryptophanhydrazide;

N-benzenesulfonyl-(R)-5-[N-(3,5-dimethylbenzoyl)-N-methyl-amino]-2-(R)-[(3-indolyl)-methyl]-4-oxo-6-(biphenyl-4-yl)-hexanoylamide;

N-benzenesulfonyl-[N-(3,5-dimethylbenzoyl)-3-[4-(5-isoxazolyl)-phenyl]-(D)-alanyl]-(L)-tryptophanamide;

N-benzenesulfonyl-[N-(3,5-dimethylbenzoyl)-N-methyl-3-(biphenyl-4-yl)-(D)-alanyl]-(L)-tryptophanamide;

N-propanesulfonyl-[N-(3,5-dimethylbenzoyl)-N-methyl-3-(biphenyl-4-yl)-(D)-alanyl]-(L)-tryptophanamide;

N-benzylsulfonyl-[N-(3,5-dimethylbenzoyl)-N-methyl-3-(biphenyl-4-yl)-(D)-alanyl]-(L)-tryptophanamide;

N-i-propanesulfonyl-[N-(3,5-dimethylbenzoyl)-N-methyl-3-(biphenyl-4-yl)-(D)-alanyl]-(L)-tryptophanamide;

N-(4-methylphenyl)sulfonyl-[N-(3,5-dimethylbenzoyl)-N-methyl-3-(biphenyl-4-yl)-(D)-alanyl]-(L)-tryptophanamide;

N-methanesulfonyl-[N-(3,5-dimethylbenzoyl)-N-methyl-(D)-3-(biphenyl-4-yl)-alanyl]-(L)-tryptophanamide;

N-(4-chlorophenyl)sulfonyl-[N-(3,5-dimethylbenzoyl)-N-methyl-(D)-3-(biphenyl-4yl)-alanyl]-(L)-tryptophanamide;

N-benzenesulfonyl-[N-(3,5-dimethylbenzoyl)-N-methyl-3-phenyl-(D)alanyl]-(L)-tryptophanamide;

N-benzenesulfonyl-[N-(3,5-dimethylbenzoyl)-N-methyl-3-(4-hydroxyphenyl)-(D)-alanyl]-(L)-tryptophanamide;

N-benzenesulfonyl-[N-(b 3,5-dimethylbenzoyl)-N-methyl-3-(2-chlorophenyl)-(D)-alanyl]-(L)-tryptophanamide;

N-methanesulfonyl-[N-(3,5-dimethylbenzoyl)-N-methyl-3-phenyl-(D)-alanyl]-(L)-tryptophanamide;

N-(2-thienyl)sulfonyl-[N-(3,5-dimethylbenzoyl)-N-methyl-3-[4-(3-thienyl)phenyl]-(D)-alanyl]-(L)-tryptophanamide;

N-propanesulfonyl-[N-(3,5-dimethylbenzoyl)-N-methyl-3-[4-(3-thienyl)phenyl]-(D)-alanyl]-(L)-tryptophanamide;

N-benzenesulfonyl-[N-(3,5-dimethylbenzoyl)-N-methyl-3-[4-(3-thienyl)phenyl]-(D)-alanyl]-(L)-tryptophanamide;

N-butanesulfonyl-[N-(3,5-dimethylbenzoyl)-N-methyl-3-[4-(3-thienyl)phenyl]-(D)-alanyl]-(L)-tryptophanamide;

N-(2-methylphenyl)sulfonyl-[N-(3,5-dimethylbenzoyl)-N-methyl-3-[4-(3-thienyl)-phenyl]-(D)-alanyl]-(L)-tryptophanamide;

N-ethanesulfonyl-[N-(3,5-dimethylbenzoyl)-N-methyl-3-[4-(3-thienyl)phenyl]-(D)-alanyl]-(L)-tryptophanamide;

N-(2-ethoxy-ethane)sulfonyl-[N-(3,5-dimethylbenzoyl)-N-methyl-3-[4-(3-thienyl)-phenyl]-(D)-alanyl]-(L)-tryptophanamide;

N-(2-trifluoro-ethane)sulfonyl-[N-(3,5-dimethylbenzoyl)-N-methyl-3-[4-(3-thienyl)-phenyl]-(D)-alanyl]-(L)-tryptophanamide;

N-(4-methoxyphenyl)sulfonyl-[N-(3,5-dimethylbenzoyl)-N-methyl-3-[4-(3-thienyl)-phenyl]-(D)-alanyl]-(L)-tryptophanamide;

N-(4-carboxyphenyl)sulfonyl-[N-(3,5-dimethylbenzoyl)-N-methyl-3-[4-(3-thienyl)-phenyl]-(D)-alanyl]-(L)-tryptophanamide;

N-(4-ethoxycarbonylphenyl)sulfonyl-[N-(3,5-dimethylbenzoyl)-N-methyl-3-[4-(3-thienyl)phenyl]-(D)-alanyl]-(L)-tryptophanamide;

N-(4-fluorophenyl)sulfonyl-[N-(3,5-dimethylbenzoyl)-N-methyl-3-[4-(3-thienyl)-phenyl]-(D)-alanyl]-(L)-tryptophanamide;

N-benzenesulfonyl-[N-(3,5-dimethylbenzoyl)-N-methyl-3-[4-(5-isoxazolyl)phenyl]-(D)-alanyl]-(L)-tryptophanamide;

N-(4-H-1,2,4-triazol-3-sulfonyl)-[N-(3,5-dimethylbenzoyl)-N-methyl-3-[4-(3-thienyl)-phenyl]-(D)- alanyl]-(L)-tryptophanamide;

N-benzenesulfonyl-[N-(3,5-dimethylbenzoyl)-N-methyl-3-(4-nitrophenyl)-(D)-alanyl]-(L)-tryptophanamide;

N-benzenesulfonyl-[N-(3,5-dimethylbenzoyl)-N-methyl-3-[4-phenoxyphenyl]-(D)-alanyl]-(L)-tryptophanamide;

N-benzenesulfonyl-[N-(3,5-dimethylbenzoyl)-N-methyl-3-[4-(3-pyridyl)-phenyl]-(D)-alanyl]-(L)-tryptophanamide;

N-(2-hydroxyethanesulfonyl)-[N-(3,5-dimethylbenzoyl)-N-methyl-3-[4-(5-isoxazolyl)-phenyl]-(D)-alanyl]-(L)-tryptophanamide;

N-(2-benzyloxyethanesulfonyl)-[N-(3,5-dimethylbenzoyl)-N-methyl-3-[4-(5-isoxazolyl)-phenyl]-(D)-alanyl]-(L)-tryptophanamide;

N-(2-pyridinesulfonyl)-[N-(3,5-dimethylbenzoyl)-N-methyl-3-[4-(5-isoxazolyl)-phenyl]-(D)-alanyl]-(L)-tryptophanamide;

N-benzenesulfonyl-[N-(3,5-dimethylbenzoyl)-N-methyl-3-[4-(3-imidazolyl)-phenyl]-(D)-alanyl]-(L)-tryptophanamide;

N-benzenesulfonyl-[N-(3,5-dimethylbenzoyl)-N-methyl-3-[4-(1,2,3-thiadiazol-4-yl)-phenyl]-(D)-alanyl]-(L)-tryptophanamide;

N-(3-carboxybenzenesulfonyl)-[N-(3,5-dimethylbenzoyl)-N-methyl-3-[4-(5-isoxazolyl)-phenyl]-(D)-alanyl]-(L)-tryptophanamide;

N-(3-ethoxycarbonylbenzenesulfonyl)-[N-(3,5-dimethylbenzoyl)- N-methyl-3-[4-(5-isoxazolyl)-phenyl]-(D)-alanyl]-(L)-tryptophanamide;

N-(2-carboxybenzenesulfonyl)-[N-(3,5-dimethylbenzoyl)-N-methyl-3-[4-(5-isoxazolyl)-phenyl]-(D)-alanyl]-(L)-tryptophanamide;

N-(2-ethoxycarbonylbenzenesulfonyl)-[N-(3,5-dimethylbenzoyl)-N-methyl-3-[4-(5-isoxazolyl)-phenyl]-(D)-alanyl]-(L)-tryptophanamide;

N-(2,6-dimethylbenzenesulfonyl)-[N-(3,5-dimethylbenzoyl)-N-methyl-3-[4-(5-isoxazolyl)-phenyl]-(D)-alanyl]-(L)-tryptophanamide;

N-(2,6-diethylbenzenesulfonyl)-[N-(3,5-dimethylbenzoyl)-N-methyl-3-[4-(5-isoxazolyl)-phenyl]-(D)-alanyl]-(L)-tryptophanamide;

N-(2,6-diisopropylbenzenesulfonyl)-[N-(3,5-dimethylbenzoyl)-N-methyl-[4-(5-isoxazolyl)-phenyl]-(D)-alanyl]-(L)-tryptophanamide;

N-(3-carboxy-3-aminopropanesulfonyl)-[N-(3,5-dimethylbenzolyl)-N-methyl-3-[4-(5-isoxazolyl)-phenyl]-(D)-alanyl]-(L)-tryptophanamide;

N-(2-carboxy-2-aminoethanesulfonyl)-[N-(3,5-dimethylbenzoyl)-N-methyl-3-[4-(5-isoxazolyl)-phenyl]-(D)-alanyl]-(L)-tryptophanamide;

N-benzenesulfonyl-[N-(3,5-dimethylbenzoyl)-N-methyl-3-[4-(1,2,4-oxadiazol-3-yl)-phenyl]-(D)-alanyl]-(L)-tryptophanamide;

N-benzenesulfonyl-[N-(3,5-dimethylbenzoyl)-N-methyl-3-[4-(3-isoxazolyl)-phenyl]-(D)-alanyl]-(L)-tryptophanamide;

N-benzenesulfonyl-[N-(3,5-dimethylbenzoyl)-N-methyl-3-[4-(5-tetrazolyl)-phenyl]-(D)-alanyl]-(L)-tryptophanamide;

N-benzenesulfonyl-[N-(3,5-dimethylbenzoyl)-N-methyl-3-[4-(1-H-pyrrol-3-yl)-phenyl]-(D)-alanyl]-(L)-tryptophanamide;

N-benzenesulfonyl-[N-(3,5-dimethylbenzoyl)-N-methyl-3-[4-(3-furanyl)-phenyl]-(D)-alanyl]-(L)-tryptophanamide;

N'-(4-carboxy-5-trifluoromethylpyrimid-2-yl)-[N-(3,5-dimethylbenzoyl)-N-methyl-(D)-3-[4-(3-thienyl)phenyl]-alanyl]-(L)-tryptophanhydrazide;

N'-(4-methoxycarbonyl-5-trifluoromethylpyrimid-2-yl)-[N-(3,5-dimethylbenzoyl)-N-methyl-(D)-3-[4-(3-thienyl)phenyl]-alanyl]-(L)-tryptophanhydrazide;

N'-(2-chlor-5-carboxyphenyl)-[N-(3,5-dimethylbenzoyl)-N-methyl-(D)-3-[4-(3-thienyl)-phenyl]-alanyl]-(L)-tryptophanhydrazide;

N'-benzoyl-[N-(3,5-dimethylbenzoyl)-N-methyl-(D)-3-[4-(3-thienyl)phenyl]-alanyl]-(L)-tryptophanhydrazide;

N-benzenesulfonyl-N-methyl-[N-(3,5-dimethylbenzoyl)-N-methyl-3-[4-(3-thienyl)-phenyl]-(D)-alanyl]-(L)-tryptophanamide;

N'-benzenesulfonyl-[N-(3,5-dimethylbenzoyl)-N-methyl-(D)-3-[4-(3-thienyl)phenyl]-alanyl]-(L)-tryptophanhydrazide;

N-benzenesulfonyl-[N-(3,5-dimethylbenzoyl)-N-methyl-3-(4-aminophenyl)-(D)-alanyl]-(L)-tryptophanamide;

N-benzenesulfonyl-[N-(3,5-dimethylbenzoyl)-N-methyl-3-(4-cyanophenyl)-(D)-alanyl]-(L)-tryptophanamide;

N'-butoxycarbonyl-[N-(3,5-dimethylbenzoyl)-N-methyl-(D)-3-[4-(3-thienyl)phenyl]-alanyl]-(L)-tryptophanhydrazide;

(57) N'-carboxymethoxycarbonyl-[N-(3,5-dimethylbenzoyl)-N-methyl-(D)-3-[4-(3-thienyl)phenyl]-alanyl]-(L)-tryptophanhydrazide;

N'-carboxyacetyl-[N-(3,5-dimethylbenzoyl)-N-methyl-(D)-3-[4-(3-thienyl)phenyl]-alanyl]-(L)-tryptophanhydrazide;

N-benzenesulfonyl-[N-(3,5-dimethylbenzoyl)-3-[4-(5-isoxazolyl)-phenyl]-(D)-alanyl]-(L)-tryptophanamide;

N-benzenesulfonyl-[N-3,5-dimethylbenzoyl)-N-methyl-2-methylalanyl]-(L)-tryptophanamide;

N-benzenesulfonyl-[N-(3,5-dimethylbenzoyl)-N-methyl-3-[4-(2-thienyl)-phenyl]-(D)-alanyl]-(L)-tryptophanamide;

N-(1,3,4-thiadiazol-2-sulfonyl)-[N-(3,5-dimethylbenzoyl)-N-methyl-3-[4-(3-thienyl)-phenyl]-(D)-alanyl]-(L)-tryptophanamide;

N'-acetyl-lN-(3,5-dimethylbenzoyl)-N-methyl-(D)-3-[4-(3-thienyl)phenyl]-alanyl]-(L)-tryptophanhydrazide;

N'-ethoxycarbonyl-[N-(3,5-dimethylbenzoyl)-N-methyl-(D)-3-[4-(3-thienyl)phenyl]-alanyl]-(L)-tryptophanhydrazide; and N'-(2-chloro-5-methoxycarbonylphenyl)-[N-(3,5-dimethylbenzoyl)-N-methyl-(D)-3-[4-(3-thienyl)phenyl]-alanyl]-tryptophanhydrazide.

14. A compound according to claim 1, selected from the group consisting of:

N-butanesulfonyl-[N-(3,5-dimethylbenzoyl)-N-methyl-3-[4-(5-isoxazolyl))-phenyl]-(D,L)-alanyl]-(L)-tryptophanamide;

N-(2-propene)sulfonyl-[N-(3,5-dimethylbenzoyl)-N-methyl-3-[4-(5-isoxazolyl)-phenyl]-(D,L)-alanyl]-(L)-tryptophanamide;

N-butanesulfonyl-[N-(3,5-dimethylbenzoyl)-N-methyl-3-[4-(5-isoxazolyl)-phenyl]-(D,L)-alanyl]-(L)-isoleucineamide;

N-butanesulfonyl-[N-(3,5-dimethylbenzoyl)-N-methyl-3-[4-(5-isoxazolyl)-phenyl]-(D,L)-alanyl]-(L)-valineamide;

N-Butanesulfonyl-[N-(3,5-dimethylbenzoyl)-N-dimethyl-3-[4-(1,2,4-triazol-1-yl)-phenyl]-(D,L)-alanyl]-(L)-tryptophanamide; and N-butanesulfonyl-lN-(3,5-dimethylbenzoyl)-N-methyl-3-[4-(1,2,3-triazol-1-yl)-phenyl]-(D,L)-alanyl]-(L)-tryptophanamide.

15. A compound according to claim 1, selected from the group consisting of:

N-methyl-N-benzenesulfonyl-[N-(3,5-dimethylbenzoyl)-N-methyl-3-[4-(5-isoxazolyl)-phenyl]-(D,L)-alanyl]-(D,L)-tryptophanamide;

N-isopropanesulfonyl-[N-(3,5-dimethylbenzoyl)-N-methyl-3-[4-(5-isoxazolyl)-phenyl]-(D,L)-alanyl]-(D,L)-tryptophanamide;

N-(4-hydroxy-benzene)-sulfonyl-[N-(3,5-dimethylbenzoyl)-N-methyl-3-[4-(5-isoxazolyl)-phenyl]-(D,L)-alanyl]-(D,L)-tryptophanamide;

N-(2-ethoxylethane)-sulfonyl-[N-(3,5-dimethylbenzoyl)-N-methyl-3-[4-(5-isoxazolyl)-phenyl]-(D,L)-alanyl]-(L)-tryptophanamide;

N-(2-nitrobenzene)-sulfonyl-[N-(3,5-dimethylbenzoyl)-N-methyl-3-[4-(5-isoxazolyl)-phenyl]-(D,L)-alanyl]-(D,L)-tryptophanamide;

N-(3-nitro-benzene)-sulfonyl-[N-(3,5-dimethylbenzoyl)-N-methyl-3-[4-(5-isoxazolyl)-phenyl]-(D,L)-alanyl]-(D,L)-tryptophanamide;

N-benzylsulfonyl-[N-(3,5-dimethylbenzoyl)-N-methyl-3-[4-(5-isoxazolyl)-phenyl]-(L)-alanyl]-(L)-tryptophanamide;

N-n-butanesulfonyl-[N-(3,5-dimethylbenzoyl)-N-methyl-3-[4-(5-isoxazolyl)-phenyl]-(L)-alanyl]-(L)-tryptophanamide;

N-n-butanesulfonyl-[N-(3,5-dimethoxybenzoyl)-N-methyl-3-[4-(5-isoxazolyl)-phenyl]-(D,L)-alanyl]-(L)-tryptophanamide;

N-n-butanesulfonyl[N-(3,5-dimethylbenzolyl)-N-methyl-3-[4-(5-isothiazolyl)-phenyl]-(D,L)-alanyl]-(L)-tryptophanamide;

N-n-butanesulfonyl-[N-(3-methyl-5methoxy-benzoyl)-N-methyl-3-[4-(5-isoxazolyl)-phenyl]-(D,L)- alanyl]-(L)-tryptophanamide;

N-n-butanesulfonyl-[N-(3,5-dimethyl-benzoyl)-N-methyl-3-[4-(5-isoxazolyl)-phenyl]-(D,L)-alanyl]-(L)-3-(2-naphthyl)-alanylamide;

N-n-butanesulfonyl-[N-(3,5-dimethyl-benzoyl)-N-methyl-3-[4-(5-isoxazolyl)-phenyl]-(D,L)-alanyl]-(L)-3-(3-naphthyl)-alanylamide;

N-(2-propene)-sulfonyl-[N-(3,5-dimethyl-benzoyl)-N-methyl-3-[4-(5-isoxazolyl)-phenyl]-(D,L)-alanyl]-(L)-tryptophanamide;

N-vinylsulfonyl-[N-(3,5-dimethyl-benzoyl)-N-methyl-3-[4-(5-isoxazolyl)-phenyl]-(D,L)-alanyl]-(L)-tryptophanamide;

N-(3-phenyl-2-propene)-sulfonyl-[N-(3,5-dimethylbenzoyl)-N-methyl-3-[4-(5-isoxazolyl)-phenyl]-(D,L)-alanyl]-(L)-tryptophanamide;

N-(3-butene)-sulfonyl-[N-(3,5-dimethyl-benzoyl)-N-methyl-3-[4-(5-isoxazolyl)-phenyl]-(D,L)-alanyl]-(L)-tryptophanamide;

N-(3-nitro-benzene)-sulfonyl-[N-(3,5-dimethylbenzoyl)-N-methyl-3-[4-(5-isoxazolyl)-phenyl]-(L)-alanyl]-(L)-tryptophanamide;

N-butanesulfonyl-[N-(3,5-dimethyl-benzoyl)-N-methyl-3-[4-(5-isoxazolyl)-phenyl]-(DL)-alanyl]-(L)-leucineamide;

N-butanesulfonyl-[N-(3,5-dimethylbenzoyl)-N-methyl-3-[4-(5-isoxazolyl)-phenyl]-(DL)-alanyl]-(L)-phenylglycinamide;

N-methallylsulfonyl-[N-(3,5-dimethylbenzoyl)-N-methyl-3-[4-(5-isoxazolyl)-phenyl]-(D,L)-alanyl]-(L)-isoleucineamide;

N-n-butanesulfonyl-[N-(3,5-dimethyl-benzoyl)-N-methyl-3-[4-(5-isoxazolyl)-phenyl]-(D,L)-alanyl]-(D,L)-3-(3,4-methylenedioxy-phenyl)-alanylamide;

N-n-butanesulfonyl-[N-(3,5-dimethyl-benzoyl)-N-methyl-3-[4-(5-isoxazolyl)-phenyl]-(D,L) -alanyl]-(D,L)-3-(3-thienyl)-alanylamide;

N-n-butanesulfonyl-[N-(3,5-dimethyl-benzoyl)-N-methyl-3-[4-(5-isoxazolyl)-phenyl]-(D,L)-alanyl]-(L)-cyclohexylglycineamide;

N-n-butanesulfonyl-[N-(3,5-dimethyl-benzoyl)-N-methyl-3-[4-(5-isoxazolyl)-phenyl]-(D,L)-alanyl]-(D,L)-(2-amino-5-phenyl)-pent-4-enoic acid amide;

N-n-butanesulfonyl-[N-(3,5-dimethylbenzoyl)-N-methyl-3-[4-(1,2,3-triazol-1-yl)-phenyl]-(D,L)-alanyl]-(L)-tryptophaneamide;

N-n-butanesulfonyl-[N-(3,5-dimethylbenzoyl)-N-methyl-3-[4-(1,2,3-triazol-2-yl)-phenyl]-(D,L)-alanyl]-(L)-tryptophanamide;

N-benzenesulfonyl-[N-(3,5-dimethylbenzoyl)-N-methyl-3-[4-(5-isoxazolyl)-phenyl]-(D,L)-alanyl]-(L)-isoleucineamide;

N-n-butanesulfonyl-[N-(3,5-dimethyl-benzoyl)-N-methyl-3-[4-(5-isoxazolyl)-phenyl]-(D,L)-alanyl]-(L)-alanylamide;

N-n-butanesulfonyl-[N-(3,5-dimethyl-benzoyl)-N-methyl-3-[4-(5-isoxazolyl)-phenyl]-(D,L)-alanyl]-(L)-(2-amino)-pent-4-enoic acid amide;

N-benzoyl-[N-(3,5-dimethyl-benzoyl)-N-methyl-3-[4-(3-thienyl)-phenyl]-(D,L)-alanyl]-(L)-tryptophanamide;

N-butanesulfonyl-[N-(3,4-methylenedioxybenzoyl)-N-methyl-3-[4-(5-isoxazolyl)-phenyl]-(D,L)-alanyl]-(L)-tryptophanamide; and N-n-butanesulfonyl-[N-(3,5-dimethyl-benzoyl)-N-methyl-3-[4-(1-pyrazolyl)-phenyl]-(D,L)-alanyl]-(L)-tryptophanamide.

16. A pharmaceutical preparation comprising an effective amount of a compound according to claim 1, in free form or in form of a pharmaceutically acceptable salt, in addition to customary pharmaceutical adjuncts.

17. A method of treating cerebral and coronary vasospasm, cerebral and coronary ischemia, subarachnoidal haemorrhage, various types of hypertension, pulmonary hypertention, cardiac failure, Raynand-syndrome, diabetes, benign prostatic hyperplasia, atherosclerosis or restenosis due to denudation following angioplasty, asthma, renal failure, dialysis, glomerular injury, hepatic failure, stomach and duodenal ulcer, ulcus cruris, various brain dysfunctions, migraine, occular diseases, glaucoma, endotoxin shock, or disseminated intravascular coagulation in a subject in need of such treatment, which method comprises administering to such subject a therapeutically effective amount of a compound according to claim 1, in the free form or in form of a pharmaceutically acceptable salt.

18. A process for the manufacture of a compound of formula I according to claim 1 which comprises a) reacting a compound of formula

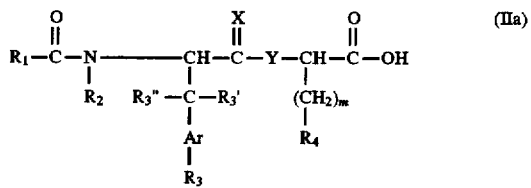

or a salt or a activated ester, reactive anhydride, or reactive cyclic amide thereof with a compound of formula $HN(R_5)-Y_1-R_6$ (IIb) or a salt thereof; or b) reacting a compound of formula

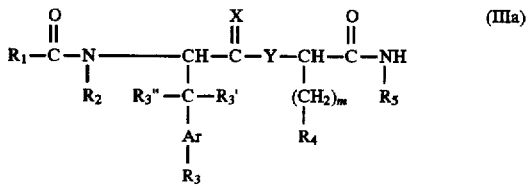

with a compound of formula $Z_1-Y_1-R_6$ (IIIb) in which $Z_1$ represents reactive esterified hydroxy; or, c) for the manufacture of a compound of formula I in which C(=X) is different from methylene or CHOH and in which Y is different from a direct bond or methylene, reacting a compound of formula

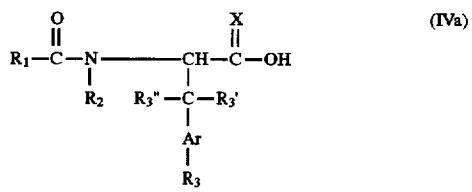

or a salt or a activated ester, reactive anhydride, or reactive cyclic amide thereof with a compound of formula

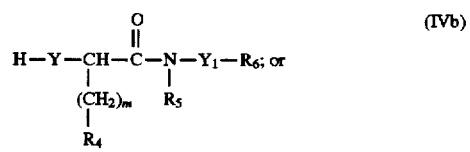

d) reacting a compound of formula $R_1$—COOH (Va) or a salt or a activated ester, reactive anhydride, or reactive cyclic amide thereof with a compound of formula (Vb)

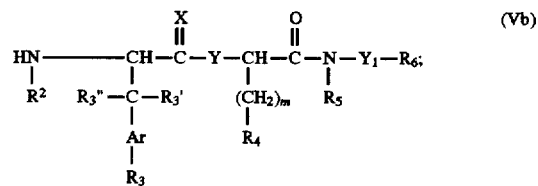

and, optionally, free functional groups in starting material of each variant, with the exception of those participating in the reaction, being optionally in protected form, and any protecting groups present are removed;

and, optionally, converting a compound I obtainable according to the process or in another manner, in free form or in salt form, into another compound I, separating a mixture of isomers obtainable according to the process and isolating the desired isomer and/or converting a free compound I obtainable according to the process into a salt or converting a salt of a compound I obtainable according to the process into the free compound I or into another salt.

* * * * *